US008956407B2

(12) United States Patent
Macoviak et al.

(10) Patent No.: US 8,956,407 B2
(45) Date of Patent: Feb. 17, 2015

(54) METHODS FOR RESHAPING A HEART VALVE ANNULUS USING A TENSIONING IMPLANT

(75) Inventors: John A. Macoviak, La Jolla, CA (US); Robert T. Chang, Belmont, CA (US); David A. Rahdert, San Francisco, CA (US); Timothy R. Machold, Moss Beach, CA (US)

(73) Assignee: MVRx, Inc., Moss Beach, CA (US)

( * ) Notice: Subject to any disclaimer, the term of this patent is extended or adjusted under 35 U.S.C. 154(b) by 1575 days.

(21) Appl. No.: 10/894,433

(22) Filed: Jul. 19, 2004

(65) Prior Publication Data

US 2005/0055089 A1    Mar. 10, 2005

Related U.S. Application Data

(63) Continuation-in-part of application No. 10/846,850, filed on May 14, 2004, now Pat. No. 8,784,482, which is a continuation-in-part of application No. 10/677,104, filed on Oct. 1, 2003, now abandoned, (Continued)

(51) Int. Cl.
*A61F 2/24* (2006.01)
*A61B 17/04* (2006.01)
*A61B 17/00* (2006.01)

(52) U.S. Cl.
CPC ............ *A61F 2/2466* (2013.01); *A61F 2/2445* (2013.01); *A61F 2/2451* (2013.01); *A61F 2/2487* (2013.01); *A61B 17/0469* (2013.01); *A61B 2017/00876* (2013.01); *A61F 2210/009* (2013.01); *A61F 2250/0012* (2013.01); *Y10S 623/904* (2013.01)
USPC ......................................... 623/2.37; 623/904

(58) Field of Classification Search
CPC ..... A61F 2/2451; A61F 2/2466; A61F 2/2487; A61B 17/0469
USPC ................. 623/2.36, 2.37, 903, 904; 606/151
See application file for complete search history.

(56) References Cited

U.S. PATENT DOCUMENTS

| | | | |
|---|---|---|---|
| 4,056,854 | A | 11/1977 | Boretos et al. |
| 4,275,469 | A | 6/1981 | Gabbay |
| 4,994,069 | A | 2/1991 | Ritchart et al. |
| 5,360,444 | A | 11/1994 | Kusuhara |

(Continued)

FOREIGN PATENT DOCUMENTS

| | | |
|---|---|---|
| WO | WO03/055417 | 7/2003 |
| WO | WO2004/045463 | 6/2004 |

OTHER PUBLICATIONS

Templeton III, et al. "Experimental Reconstruction of Cardiac Valves by Venous and Pericardial Grafts." Annals of Surgery vol. 129, No. 2, Feb. 1949, 161-176.

(Continued)

*Primary Examiner* — Brian Pellegrino
(74) *Attorney, Agent, or Firm* — Ryan Kromholz & Manion, S.C.

(57) ABSTRACT

Implants or systems of implants apply a selected force vector or a selected combination of force vectors within or across the left atrium, which allow mitral valve leaflets to better coapt. The implants or systems of implants make possible rapid deployment, facile endovascular delivery, and full intra-atrial retrievability. The implants or systems of implants also make use of strong fluoroscopic landmarks.

8 Claims, 28 Drawing Sheets

Related U.S. Application Data which is a continuation-in-part of application No. 09/666,617, filed on Sep. 20, 2000, now Pat. No. 6,893,459, application No. 10/894,433, which is a continuation-in-part of application No. 10/695,433, filed on Oct. 28, 2003, now Pat. No. 7,291,168, which is a continuation of application No. PCT/US02/31376, filed on Oct. 1, 2002, and a continuation-in-part of application No. 10/676,729, filed on Oct. 1, 2003, now Pat. No. 7,527,646, and a continuation-in-part of application No. 10/676,815, filed on Oct. 1, 2003, now Pat. No. 7,381,220.

(60) Provisional application No. 60/429,444, filed on Nov. 26, 2002, provisional application No. 60/326,590, filed on Oct. 1, 2001, provisional application No. 60/429,462, filed on Nov. 26, 2002, provisional application No. 60/429,709, filed on Nov. 26, 2002.

(56) References Cited

U.S. PATENT DOCUMENTS

| | | | |
|---|---|---|---|
| 5,370,685 A | 12/1994 | Stevens | |
| 5,545,241 A | 8/1996 | Vanderauwera et al. | |
| 5,716,397 A | 2/1998 | Myers | |
| 5,776,189 A | 7/1998 | Khalid | |
| 5,792,155 A | 8/1998 | Van Cleef | |
| 5,830,224 A | 11/1998 | Cohn et al. | |
| 5,851,185 A | 12/1998 | Berns | |
| 5,855,601 A | 1/1999 | Bessler et al. | |
| 5,961,440 A | 10/1999 | Schweich, Jr. et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,099,542 A | 8/2000 | Cohn et al. | |
| 6,102,932 A | 8/2000 | Kurz | |
| 6,162,168 A | 12/2000 | Schweich, Jr. et al. | |
| 6,165,119 A | 12/2000 | Schweich, Jr. et al. | |
| 6,183,411 B1 | 2/2001 | Mortier et al. | |
| 6,210,432 B1 | 4/2001 | Solem et al. | |
| 6,231,587 B1 | 5/2001 | Makower | |
| 6,260,552 B1 | 7/2001 | Mortier et al. | |
| 6,261,222 B1 | 7/2001 | Schweich, Jr. et al. | |
| 6,287,339 B1 | 9/2001 | Vazquez et al. | |
| 6,299,637 B1 | 10/2001 | Shaolian et al. | |
| 6,312,464 B1 | 11/2001 | Navia | |
| 6,312,465 B1 | 11/2001 | Griffin et al. | |
| 6,332,864 B1 | 12/2001 | Schweich, Jr. et al. | |
| 6,332,893 B1 | 12/2001 | Mortier et al. | |
| 6,338,470 B1 | 1/2002 | Steely et al. | |
| 6,338,735 B1 | 1/2002 | Stevens | |
| 6,338,740 B1 | 1/2002 | Carpentier | |
| 6,402,781 B1 | 6/2002 | Langberg et al. | |
| 6,419,695 B1 | 7/2002 | Gabbay | |
| 6,419,696 B1 | 7/2002 | Ortiz et al. | |
| 6,440,164 B1 | 8/2002 | DiMatteo et al. | |
| 6,454,799 B1 | 9/2002 | Schreck | |
| 6,458,153 B1 | 10/2002 | Bailey et al. | |
| 6,503,272 B2 | 1/2003 | Duerig et al. | |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,629,534 B1 | 10/2003 | St. Goar et al. | |
| 6,656,221 B2 | 12/2003 | Taylor et al. | |
| 6,669,709 B1 | 12/2003 | Cohn et al. | |
| 6,676,699 B2 | 1/2004 | Shiu | |
| 6,685,739 B2 | 2/2004 | DiMatteo et al. | |
| 6,702,826 B2 | 3/2004 | Liddicoat et al. | |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 6,805,711 B2 | 10/2004 | Quijano et al. | |
| 6,893,459 B1 | 5/2005 | Macoviak | |
| 6,913,608 B2 | 7/2005 | Liddicoat et al. | |
| 6,945,978 B1 | 9/2005 | Hyde | |
| 7,004,176 B2 | 2/2006 | Lau | |
| 7,077,862 B2 | 7/2006 | Vidlund et al. | |
| 7,166,126 B2 | 1/2007 | Spence et al. | |
| 7,967,808 B2 | 6/2011 | Fitzgerald et al. | |
| 2001/0010017 A1 | 7/2001 | Letac et al. | |
| 2001/0021872 A1 | 9/2001 | Bailey et al. | |
| 2001/0051824 A1 | 12/2001 | Hopkins et al. | |
| 2002/0032481 A1 | 3/2002 | Gabbay | |
| 2002/0065554 A1 | 5/2002 | Streeter | |
| 2002/0094573 A1 | 7/2002 | Bell | |
| 2002/0123802 A1 | 9/2002 | Snyders | |
| 2002/0129820 A1 | 9/2002 | Ryan et al. | |
| 2002/0138138 A1 | 9/2002 | Yang | |
| 2002/0183841 A1 | 12/2002 | Cohn et al. | |
| 2003/0014104 A1 | 1/2003 | Cribier | |
| 2003/0040792 A1 | 2/2003 | Gabbay | |
| 2003/0069593 A1 | 4/2003 | Tremulis et al. | |
| 2003/0078465 A1 | 4/2003 | Pai et al. | |
| 2003/0120340 A1 | 6/2003 | Liska et al. | |
| 2003/0181928 A1 | 9/2003 | Vidlund et al. | |
| 2003/0199974 A1 | 10/2003 | Lee et al. | |
| 2003/0233022 A1 | 12/2003 | Vidlund et al. | |
| 2004/0148019 A1 | 7/2004 | Vidlund et al. | |
| 2004/0162610 A1 | 8/2004 | Liska et al. | |
| 2004/0260317 A1* | 12/2004 | Bloom et al. | 606/151 |
| 2005/0010277 A1 | 1/2005 | Chuter | |
| 2005/0075723 A1 | 4/2005 | Schroeder et al. | |
| 2005/0267571 A1 | 12/2005 | Spence et al. | |
| 2006/0241745 A1 | 10/2006 | Solem | |
| 2006/0282161 A1 | 12/2006 | Huynh et al. | |

OTHER PUBLICATIONS

Moore et al. "Unsuitability of Transventricular Autogenous Slings for Diminishing Valvular Insufficiency." Surgery, vol. 33, No. 2, Feb. 1953, 173-182.

Murray et al. "Reconstruction of the Valves of the Heart." The Canadian Medical Association Journal, vol. 38, No. 4, Apr. 1938, 317-319.

Bolling et al. "Early Outcome of Mitral Valve Reconstruction in Patients With End-Stage Cardiomyopathy." J Thorac Cardiovasc Surg 1995; 109:676-683.

Kameda et al. "Annuloplasty for Severe Mitral Regurgitation Due to Dilated Cardiomyopathy." Ann Thorac Surg 1996; 61:1829-1832.

Bolling et al. "Intermediate-Term Outcome of Mitral Reconstruction in Cardiomyopathy." Journal of Thoracic Cardiovascular Surgery, vol. 115, No. 2, Feb. 1998, 381-388.

Harlan et al. Manual of Cardiac Surgery, vol. 2, 1981 Figs. 16.3-16.4.

Edmunds, Jr. et al. "Septal Defect." Atlas of Cardiothoracic Surgery 1990.

Koniaris, MD et al. "Dynamic Retention: A Technique for Closure of the Complex Abdomen in Critically Ill Patients." Archives of Surgery, vol. 136, No. 12, Dec. 2001, 1359-1362.

Fucci et al. "Improved Results With Mitral Valve Repair Using New Surgical Techniques." European Journal of Cardio-Thoracic Surgery, vol. 9, 1995, 621-626.

Davila et al. "Circumferential Suture of the Mitral Ring: A Method for the Surgical Correction of Mitral Insufficiency." Journal of Thoracic Surgery Nov. 1955; 30(5): 531-60.

Kuykendall et al. "Surgical Correction of Chronic Mitral Insufficiency in Dogs." Surgery. Oct. 1958; 44(4):718-25.

Harken et al. "The Surgical Correction of Mitral Insufficiency." Surgical Forum 4:4-7 1953.

Davila et al. "A Method for the Surgical Correction of Mitral Insufficiency." Surgery, Gynecology and Obstetrics Apr. 1954; 98(4):407-12.

Davila et al. "The Clinical and Physiologic Criteria for Surgical Correction of Mitral Insufficiency." Journal of Thoracic Surgery Feb. 1958; 35(2):206-31.

Glover et al. "The Treatment of Mitral Insufficiency by the Purse-String Technique." Journal of Thoracic Surgery Jan. 1957; 33(1): 75-101.

(56) References Cited

OTHER PUBLICATIONS

Rankin et al. "A Clinical Comparison of Mitral Valve Repair Versus Valve Replacement in Ischemic Mitral Regurgitation." J Thorac Cardiovasc Surg. Feb. 1988; 95(2):165-77.
Barnard et al. "A Surgical Approach to Mitral Insufficiency." Br J Surg. May 1961; 48:655-62.
McKenzie et al. "Current Concepts in Surgical Correction of Acquired Mitral Insufficiency." Circulation. Oct. 1963; 28:603-16.
Saab et al. "Left Ventricular Aneurysm: A New Surgical Approach." Thorac Cardiovasc Surg. Feb. 1989; 37(1):11-9.
Cicek et al. "Left Ventricular Endoaneurysmorrhaphy: Effect on Left Ventricular Size, Shape and Function." Cardiology. Jul.-Aug. 1997; 88(4):340-5.
Liedtke et al. "Functional Reductions in Left Ventricular Volume." J Thorac Cardiovasc Surg. Feb. 1976; 71(2):195-206.
Sosa et al. "Recurrent Ventricular Tachycardia Associated With Postinfarction Aneurysm. Results of Left Ventricular Reconstruction." J Thorac Cardiovasc Surg. May 1992; 103(5); 855-60.
Cooley, "Repair of Postinfarction Ventricular Septal Defect." J Card Surg. Jul. 1994; 9(4):427-9.
Jatene, "Left Ventricular Aneurysmectomy. Resection or Reconstruction." J Thorqc Cardiovasc Surg 1985; 89:321-31.
de Silva et al. "Postinfarction Ventricular Septal Defect. An Efficacious Technique for Early Surgical Repair." J Throac Cardiovasc Surg. Jan. 1989; 97(1):86-9.
Tashiro et al. "Extended Endocardial Repair of Postinfarction Ventricular Septal Rupture: New Operative Technique-Modification of the Komeda-David Operation." J Card Surg. Mar. 1994; 9(2):97-102.
Daggett, "Surgical Technique for Early Repair of Posterior Ventricular Septal Rupture." J Thorac Cardiovasc Surg. Aug. 1982;84(2):306-12.
Daggett et al. "Surgery for Post-Myorcardial Infarct Ventricular Septal Defect." Ann Surg. Sep. 1977;186(3):260-71.
Dor, "Left Ventricular Aneurysms: the Endoventricular Circular Patch Plasty." Semin Thorac Cardiovasc Surg. Apr. 1997;9(2):123-30.
Antunes, "Submitral Left Ventricular Aneurysms. Correction by a New Transatrial Approach." J Thorac Cardiovasc Surg. Aug. 1987;94(2):241-5.
Alvarez et al. "Technical Improvements in the Repair of Acute Postinfarction Ventricular Septal Rupture." J Card Surg. Sep. 1992;7(3):198-202.
Cox, "Surgical Management of Left Ventricular Aneurysms: A Clarification of the Similarities and Differences Between the Jatene and Dor Techniques." Semin Thorqc Cardiovasc Surg. Apr. 1997;9(2):131-8.
Skillington et al. "Surgical Treatment for Infarct-Related Ventricular Septal Defects. Improved Early Results Combined with Analysis of Late Functional Status." J thorac Cardiovasc Surg. May 1990;99(5):798-808.
Salati et al. "Severe Diastolic Dysfunction After Endoventriculoplasty." J Thorac Cardiovasc Surg. Apr. 1995;109(4):694-701.
Yacoub et al. "Anatomic Correction of the Syndrome of Prolapsing Right Coronary Aortic Cusp, Dilatation of the Sinus of Valsalva, and Ventricular Septal Defect." J thorac Cardiovasc Surg. Feb. 1997;113(2):253-60.
Wilson, W.C., "Studies in Experimental Mitral Obstruction in Relation to the Surgical Treatment of Mitral Stenosis." The British Journal of Surgery, vol. XVIII, No. 70 ;259-74.
Bailey, et al. "Surgical Repair of Mitral Insufficiency." Diseases of the Chest, vol. XIX , No. 2, Feb. 1951, 125-137.
Henderson, et al., "The Surgical Treatment of Mitral Insufficiency." Experimental Use of Transplanted Pericardium in Dogs. Surgery 33(6):858-868; 1953.
Sakakibara, "A Surgical Approach to the Correction of Mitral Insufficiency." Annals of Surgery. vol. 142, No. 2, Aug. 1955, 196-203.
Harken et al. "The Surgical Correction of Mitral Insufficiency." The Journal of Thoracic Surgery. 28(6):604-627., 1954.
Bailey et al. "The Surgical Correction of Mitral Insufficiency by the Use of Pericardial Grafts." The Journal of Thoracic Surgery, vol. 28, No. 6, Dec. 1954, 551-603.
Kay et al. "Surgical Treatment of Mitral Insufficiency." Surgery. vol. 37, No. 5. May 1955, 697-706.

\* cited by examiner

METHODS FOR RESHAPING A HEART VALVE ANNULUS USING A TENSIONING IMPLANT

RELATED APPLICATIONS

This application is a continuation-in-part of U.S. patent application Ser. No. 10/846,850, filed May 14, 2004, entitled "Devices, Systems, and Methods for Reshaping a Heart Valve Annulus, which is continuation-in-part of U.S. patent application Ser. No. 10/677,104, filed Oct. 1, 2003, now abandoned and entitled "Devices, Systems, and Methods for Reshaping a Heart Valve Annulus," which claims the benefit of U.S. Provisional Patent Application Ser. No. 60/429,444, filed Nov. 26, 2002, and entitled "Heart Valve Remodeling Devices," and which is a continuation-in-part of U.S. patent application Ser. No. 09/666,617, filed Sep. 20, 2000 now U.S. Pat. No. 6,893,459, and entitled "Heart Valve Annulus Device and Methods of Using Same," which is incorporated herein by reference. This application is also a continuation-in-part of U.S. patent application Ser. No. 10/695,433, filed Oct. 28, 2003, now U.S. Pat. No. 7,291,168, entitled "Methods and Devices for heart Valve Treatments," which is a continuation of Patent Cooperation Treaty Application Serial No. PCT/US02/31376, filed Oct. 1, 2002 and entitled "Systems and Devices for Heart Valve Treatments," which claimed the benefit of U.S. Provisional Patent Application Ser. No. 60/326,590, filed Oct. 1, 2001, which are incorporated herein by reference. This application is also a continuation-in-part of U.S. patent application Ser. No. 10/676,729, filed Oct. 1, 2003, now U.S. Pat. No. 7,527,646, and entitled "Devices, Systems, and Methods for Retaining a Native heart Valve Leaflet," which claims the benefit of U.S. Provisional Patent Application Ser. No. 60/429,462, filed Nov. 26, 2002, and entitled "Heart Valve Leaflet Retaining Devices," which are incorporated herein by reference. This application is also a continuation-in-part of U.S. patent application Ser. No. 10/676,815, filed Oct. 1, 2003, now U.S. Pat. No. 7,381,220, and entitled "Devices, Systems and Methods for Supplementing, Repairing or Replacing a Native Heart Valve Leaflet," which claims the benefit of U.S. Provisional Patent Application Ser. No. 60/429,709, filed Nov. 26, 2002, and entitled "Neo-Leaflet Medical Devices," which are incorporated herein by reference.

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. The ventricles are the blood-discharging chambers. A wall composed of fibrous and muscular parts, called the interatrial septum separates the right and left atria (see FIGS. 2 to 4). The fibrous interatrial septum is, compared to the more easily shredded muscle tissue of the heart, a more materially strong tissue structure in its own extent in the heart. An anatomic landmark on the interatrial septum is an oval, thumbprint sized depression called the oval fossa, or fossa ovalis (shown in FIGS. 4 and 6), which is a remnant of the oval foramen and its valve in the fetus. It is free of any vital structures such as valve structure, blood vessels and conduction pathways. Together with its inherent fibrous structure and surrounding fibrous ridge which makes it identifiable by angiographic techniques, the fossa ovalis is the favored site for trans-septal diagnostic and therapeutic procedures from the right into the left heart. Before birth, oxygenated blood from the placenta was directed through the oval foramen into the left atrium, and after birth the oval foramen closes.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atria into the corresponding ventricles. Shortly after ventricular systole (i.e., ventricular emptying) begins, the tricuspid and mitral valves close (see FIG. 3)—to prevent back flow from the ventricles into the corresponding atria—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

The mitral and tricuspid valves are defined by fibrous rings of collagen, each called an annulus, which forms a part of the fibrous skeleton of the heart. The annulus provides attachments for the two cusps or leaflets of the mitral valve (called the anterior and posterior cusps) and the three cusps or leaflets of the tricuspid valve. The leaflets receive chordae tendineae from more than one papillary muscle. In a healthy heart, these muscles and their tendinous cords support the mitral and tricuspid valves, allowing the leaflets to resist the high pressure developed during contractions (pumping) of the left and right ventricles. FIGS. 5 and 6 show the chordae tendineae and papillary muscles in the left ventricle that support the mitral valve.

As FIGS. 2 and 3 show, the anterior portion of the mitral valve annulus is intimate with the non-coronary leaflet of the aortic valve. As FIGS. 2 and 3 also show, the mitral valve annulus is also near other critical heart structures, such as the circumflex branch of the left coronary artery (which supplies the left atrium, a variable amount of the left ventricle, and in many people the SA node) and the AV node (which, with the SA node, coordinates the cardiac cycle).

Also in the vicinity of the posterior mitral valve annulus are the coronary sinus and its tributaries. These vessels drain the areas of the heart supplied by the left coronary artery. The coronary sinus and its tributaries receive approximately 85% of coronary venous blood. The coronary sinus empties into the posterior of the right atrium, anterior and inferior to the fossa ovalis (see FIG. 4). A tributary of the coronary sinus is called the great cardiac vein, which courses parallel to the majority of the posterior mitral valve annulus, and is superior to the posterior mitral valve annulus by an average distance of about 9.64±3.15 mm.

II. Characteristics and Causes of Mitral Valve Dysfunction

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (see FIGS. 7 and 8), the dimensions of the mitral valve annulus create an anatomic shape and tension such that the leaflets coapt, forming a tight junction, at peak contraction pressures. Where the leaflets coapt at the opposing medial and lateral sides of the annulus are called the leaflet commissures.

Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease.

Regardless of the cause (see FIG. 9), mitral valve dysfunction can occur when the leaflets do not coapt at peak contraction pressures. As FIG. 9 shows, the coaptation line of the two leaflets is not tight at ventricular systole. As a result, an undesired back flow of blood from the left ventricle into the left atrium can occur.

Mitral regurgitation is a condition where, during contraction of the left ventricle, the mitral valve allows blood to flow backwards from the left ventricle into the left atrium. This has two important consequences.

First, blood flowing back into the atrium may cause high atrial pressure and reduce the flow of blood into the left atrium from the lungs. As blood backs up into the pulmonary system, fluid leaks into the lungs and causes pulmonary edema.

Second, the blood volume going to the atrium reduces volume of blood going forward into the aorta causing low cardiac output. Volume overloads the ventricle, as the excess blood in the atrium over-fills the ventricle during each cardiac cycle.

Mitral regurgitation is measured on a numeric Grade scale of 1+ to 4+ by either contrast ventriculography or by echocardiographic Doppler assessment. Grade 1+ is trivial regurgitation and has little clinical significance. Grade 2+ shows a jet of reversed flow going halfway back into the left atrium. Grade 3 regurgitation shows filling of the left atrium with reversed flow up to the pulmonary veins and a contrast injection that clears in three heart beats or less. Grade 4 regurgitation has flow reversal into the pulmonary veins and a contrast injection that does not clear from the atrium in three or fewer heart beats.

Mitral regurgitation is categorized into two main types, (i) organic or structural and (ii) functional. Organic mitral regurgitation results from a structurally abnormal valve component that causes a valve leaflet to flail upward and leak during systole. Functional mitral regurgitation results from annulus dilation due to primary congestive heart failure, the latter of which is itself generally surgically untreatable, and not due to a reversible cause like severe ischemia or primary valvular heart disease.

Organic mitral regurgitation is seen when a disruption of the seal occurs at the free leading edge of the leaflet due to a ruptured chord or papillary muscle making the leaflet flail; or if the leaflet tissue is redundant, the valves may prolapse the level at which coaptation occurs higher into the atrium with further prolapse opening the valve higher in the atrium during ventricular systole.

Functional mitral regurgitation occurs as a result of dilation of heart and mitral annulus secondary to heart failure, most often as a result of coronary artery disease or idiopathic dilated cardiomyopathy. Comparing a healthy annulus in FIG. 7 to an unhealthy annulus in FIG. 9, the unhealthy annulus is dilated and, in particular, the anterior-to-posterior distance along the minor axis is increased. As a result, the shape and tension defined by the annulus becomes less oval (see FIG. 7) and more round (see FIG. 9). This condition is called dilation. When the annulus is dilated, the shape and tension conducive for coaptation at peak contraction pressures progressively deteriorate.

The fibrous mitral annulus is attached to the anterior mitral leaflet in one-third of its circumference. The muscular mitral annulus constitutes the remainder of the mitral annulus and is attached to by the posterior mitral leaflet. The anterior fibrous mitral annulus is intimate with the central fibrous body, the two ends of which are called the fibrous trigones. Just posterior to each fibrous trigone is the commissure of which there are two, the anterior and the posterior commissure. The commissure is where the anterior leaflet meets the posterior leaflet at the annulus.

As before described, the central fibrous body is also intimate with the non-coronary leaflet of the aortic valve. The central fibrous body is fairly resistant to elongation during the process of mitral annulus dilation. It has been shown that the great majority of mitral annulus dilation occurs in the posterior two-thirds of the annulus known as the muscular annulus. One could deduce thereby that, as the annulus dilates, the percentage that is attached to the anterior mitral leaflet diminishes.

In functional mitral regurgitation, the dilated annulus causes the leaflets to separate anterior from posterior leaflet at their coaptation points in all phases of the cardiac cycle. Onset of mitral regurgitation may be acute, or gradual and chronic in either organic or in functional mitral regurgitation.

In dilated cardiomyopathy of ischemic or of idiopathic origin, the mitral annulus can dilate to the point of causing functional mitral regurgitation. It does so in approximately twenty-five percent of patients with congestive heart failure. If subjected to exercise, echocardiography shows the incidence of functional mitral regurgitation in these patients rises to over fifty percent.

Functional mitral regurgitation is a significantly aggravating problem for the dilated heart, as is reflected in the increased mortality of these patients compared to otherwise comparable patients without functional mitral regurgitation. One mechanism by which functional mitral regurgitation aggravates the situation in these patients is through increased volume overload imposed upon the ventricle. Due directly to the leak, there is increased work the heart is required to perform in each cardiac cycle to eject blood antegrade through the aortic valve and retrograde through the mitral valve. The latter is referred to as the regurgitant fraction of left ventricular ejection. This is added to the forward ejection fraction to yield the total ejection fraction. A normal heart has a forward ejection fraction of seventy percent. With functional mitral regurgitation and dilated cardiomyopathy the ejection fraction is typically less than thirty percent. If the regurgitant fraction is half the ejection fraction in the latter group the forward ejection fraction can be as low as fifteen percent.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

Currently, patient selection criteria for mitral valve surgery are very selective. Patients will ideally have normal ventricular function, general good health, and a predicted lifespan of greater than 3 to 5 years, NYHA Class III or IV symptoms, and at least Grade 3 regurgitation as indications for mitral surgery. Younger patients with less severe symptoms may be indicated for early surgery if mitral repair is anticipated. The most common surgical mitral repair procedure is for organic mitral regurgitation due to a ruptured chord on the middle scallop of the posterior leaflet.

In conventional annuloplasty ring repair, the posterior annulus is reduced along its length with sutures passed through a surgical annuloplasty sewing ring cuff. The goal of such a repair is to bring the posterior mitral leaflet forward toward to the anterior leaflet to better allow coaptation.

Surgical edge-to-edge juncture repairs, which can be performed endovascularly, are also made, in which a mid valve leaflet to mid valve leaflet suture or clip is applied to keep these points of the leaflet held together throughout the cardiac cycle. Edwards Life Sciences Corporation and Evalve Inc. have developed, respectively, a transvascular suture and a clip to grasp and bond the two mitral leaflets in the beating heart.

Grade 3+ or 4+ organic mitral regurgitation may be repaired with such edge-to-edge technologies. This is because, in organic mitral regurgitation, the problem is not the annulus but in the central valve components.

However, functional mitral regurgitation can persist at a high level, even after edge-to-edge repair, particularly in cases of high Grade 3+ and 4+ functional mitral regurgitation.

In another emerging technology, the coronary sinus is mechanically deformed through endovascular means applied and contained to function solely within the coronary sinus. Early clinical reports in humans report the inability of these endovascular coronary sinus technologies to reshape the mitral annulus.

It is reported that twenty-five percent of the six million Americans who will have congestive heart failure will have functional mitral regurgitation to some degree. This constitutes the 1.5 million people with functional mitral regurgitation. Of these, the idiopathic dilated cardiomyopathy accounts for 600,000 people. Of the remaining 900,000 people with ischemic disease, approximately half have functional mitral regurgitation due solely to dilated annulus.

By interrupting the cycle of progressive functional mitral regurgitation, it has been shown in surgical patients that survival is increased and in fact forward ejection fraction increases in many patients. The problem with surgical therapy is the significant insult it imposes on these chronically ill patients with high morbidity and mortality rates associated with surgical repair.

The need remains for simple, cost-effective, and less invasive devices, systems, and methods for treating dysfunction of a heart valve, e.g., in the treatment of organic and functional mitral valve regurgitation.

SUMMARY OF THE INVENTION

The invention comprises various aspects, which are separate and distinct but which can be combined for use, if desired.

One aspect of the invention provides devices, systems, and methods for treating a mitral heart valve using an anchor structure that is located within the great cardiac vein.

In one embodiment, the devices, systems, and methods install the anchor structure within the great cardiac vein adjacent a length comprising at least a portion of a posterior annulus of the mitral valve. The devices, systems, and methods couple a posterior region of an implant to the anchor structure within great cardiac vein and extend the implant across the left atrium, through an interatrial septum, and into a right atrium. The devices, systems, and methods tension the implant and anchor an anterior region of the implant to tissue in or near the right atrium to maintain the tension. The tension applied by the implant can improve septal-to-lateral dimensions of the valve and thereby lead to improved leaflet coaption to ameliorate functional mitral valve regurgitation. In the case of organic mitral valve regurgitation, the tension applied by the implant can serve the stabilize the posterior annulus in the manner of an annuloplasty ring, to resist change in annulus size during the cardiac cycle.

In one embodiment, the anchor structure can also serve to consolidate the great cardiac vein into a unified physical structure along its length. In this arrangement, the tension applied to the implant is uniformly distributed as a force vector to atrial tissue adjacent the posterior mitral valve annulus through the consolidated great cardiac vein. The consolidation of tissue can enhance the beneficial effects of the implant.

In one embodiment, the devices, systems, and methods conjoin the great cardiac vein to the left ventricle in a tissue region between the consolidated great cardiac vein and the left ventricle. In this arrangement, the implant is configured, when placed into tension, to apply a force vector upon the tissue consolidating anchor structure within the great cardiac vein. The force vector x can be upward, inward, or a combination of both. The force vector is directed by the conjoined tissue region to the left ventricle, to relieve tension on the annulus. As before, the beneficial effects achieved can be thereby further enhanced.

Another aspect of the invention provides devices, systems, and methods for treating a mitral heart valve using an elongated structure sized and configured to be deployed in tension a circumferential path within the great cardiac vein adjacent a posterior annulus of the mitral valve. The structure includes an end anchoring region sized and configured to extent from the coronary sinus into the right atrium. An anchor couples to the end anchoring region on the interatrial septum in the right atrium. The tension applied by the implant can improve septal-to-lateral dimensions of the valve and thereby lead to improved leaflet coaption to ameliorate functional mitral valve regurgitation. In the case of organic mitral valve regurgitation, the tension applied by the implant can serve the stabilize the posterior annulus in the manner of an annuloplasty ring, to resist change in annulus size during the cardiac cycle.

Another aspect of the invention provides devices, systems, and methods for treating a mitral heart valve using an elongated structure sized and configured to be deployed as a loop at least in part within the great cardiac vein. In this arrangement, the elongated structure includes first and second end anchoring regions. The elongated structure also includes an intermediate region coupled to the first and second end anchoring regions. Each end anchoring region is sized and configured, in use, to extend into the right atrium, while the intermediate region is sized and configured to extend outside the right atrium in a circumferential path within the great cardiac vein adjacent a posterior annulus of the mitral valve. An anchor couples to the first and second end anchoring regions in the right atrium or a vena cava to hold the intermediate region in tension within the great cardiac vein. The tension applied by the implant can improve septal-to-lateral dimensions of the valve and thereby lead to improved leaflet coaption to ameliorate functional mitral valve regurgitation. In the case of organic mitral valve regurgitation, the tension applied by the implant can serve the stabilize the posterior annulus in the manner of an annuloplasty ring, to resist change in annulus size during the cardiac cycle.

Another aspect of the invention provides devices, systems, and methods for placing implants within a heart chamber. A first implant is deployed within a heart vessel adjacent to a heart chamber, and a second implant is deployed within the heart chamber. According to this aspect of the invention, a region of the second implant within the heart chamber is magnetically attracting to a region of the first implant within the heart vessel e.g., so that the region of the second implant can be coupled to the region of the first implant within the heart vessel.

Other features and advantages of the invention shall be apparent based upon the accompanying description, drawings, and claims.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

Figure 1:
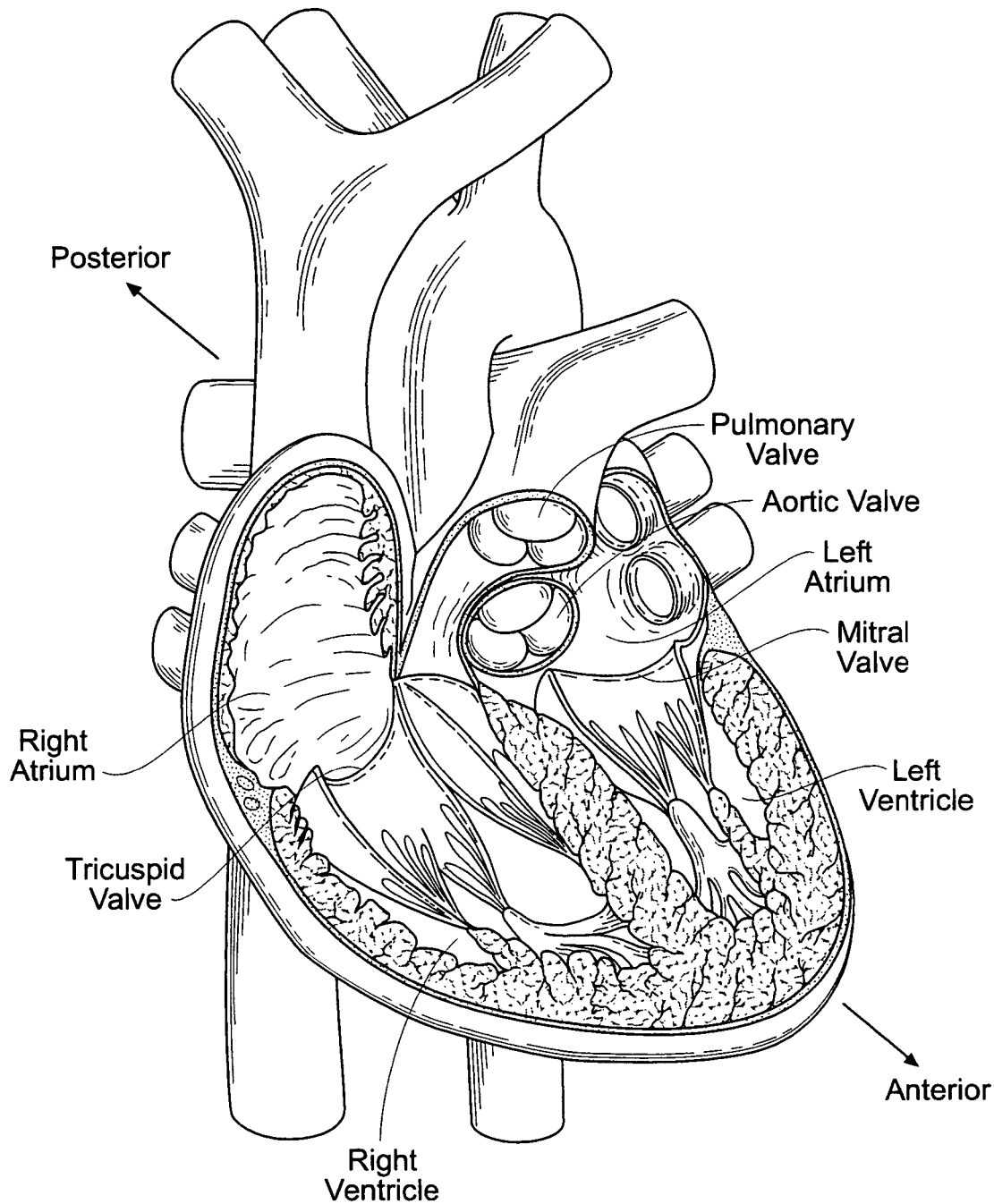
FIG. 1 is an anatomic anterior view of a human heart, with portions broken away and in section to view the interior heart chambers and adjacent structures.
Figure 2:
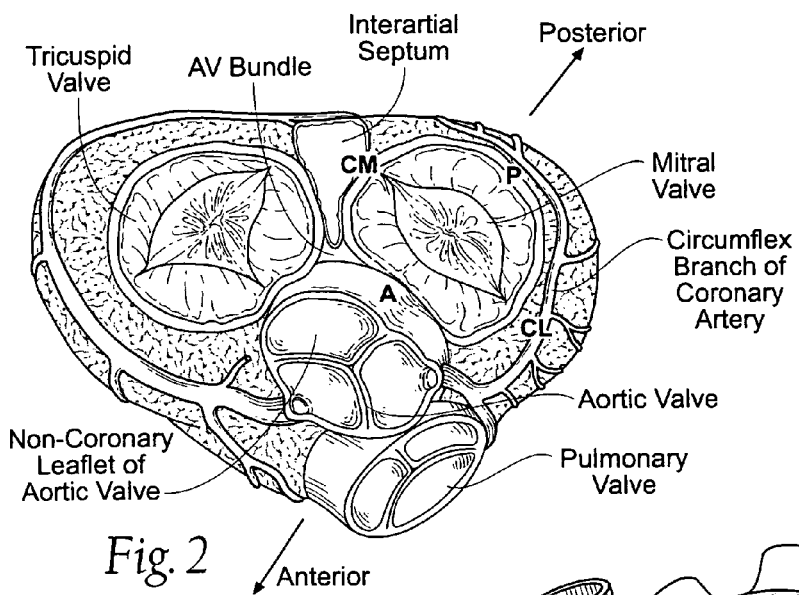
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
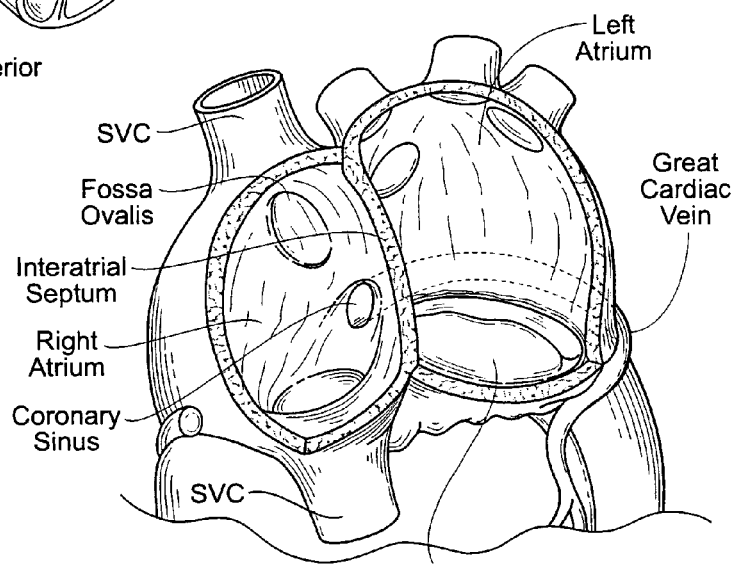
FIG. 4 is an anatomic anterior perspective view of the left and right atriums, with portions broken away and in section to show the interior of the heart chambers and association structures, such as the fossa ovalis, coronary sinus, and the great cardiac vein.
Figure 3:
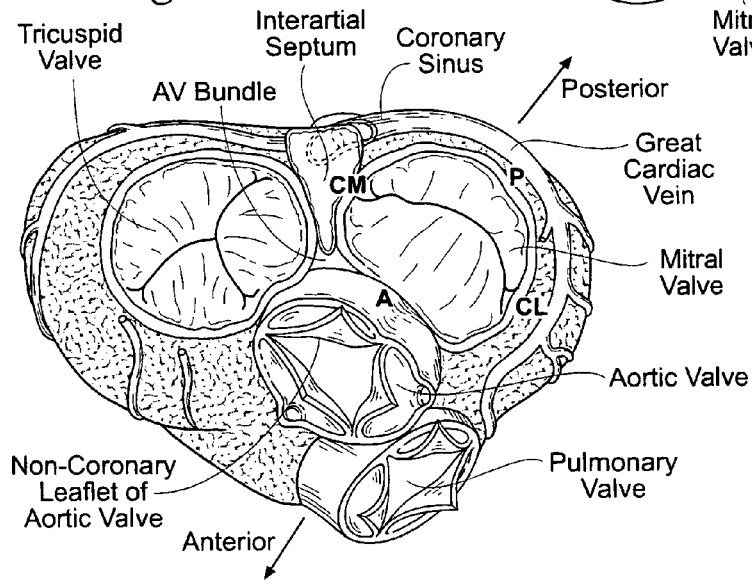
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.
Figure 5:
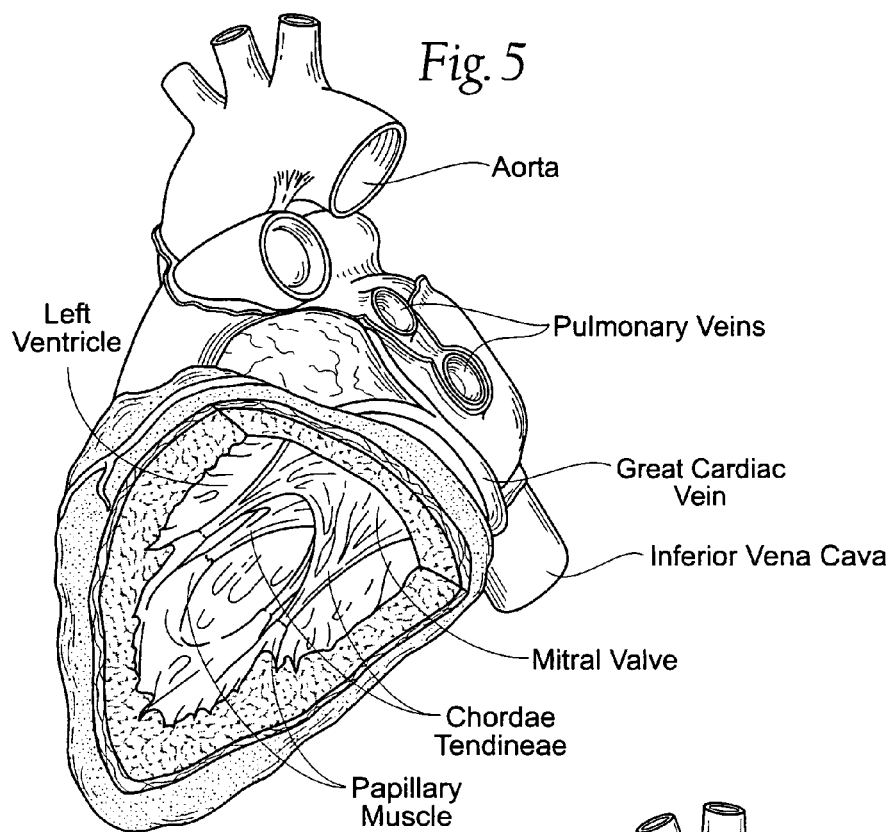
FIG. 5 is an anatomic lateral view of a human heart with portions broken away and in section to show the interior of the left ventricle and associated muscle and chord structures coupled to the mitral valve.
Figure 6:
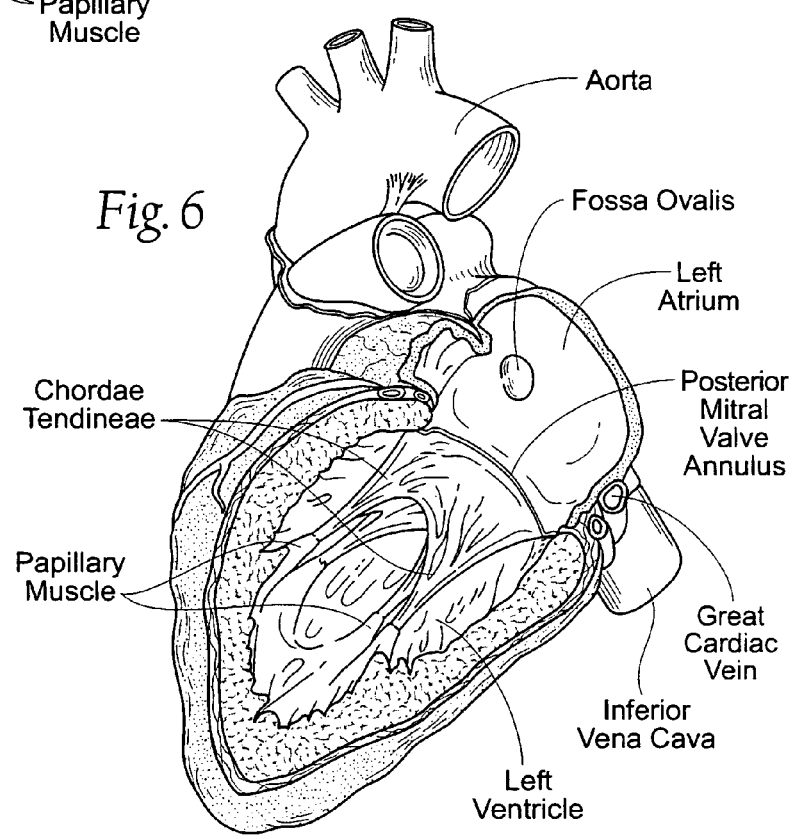
FIG. 6 is an anatomic lateral view of a human heart with portions broken away and in section to show the interior of the left ventricle and left atrium and associated muscle and chord structures coupled to the mitral valve.
Figure 7:
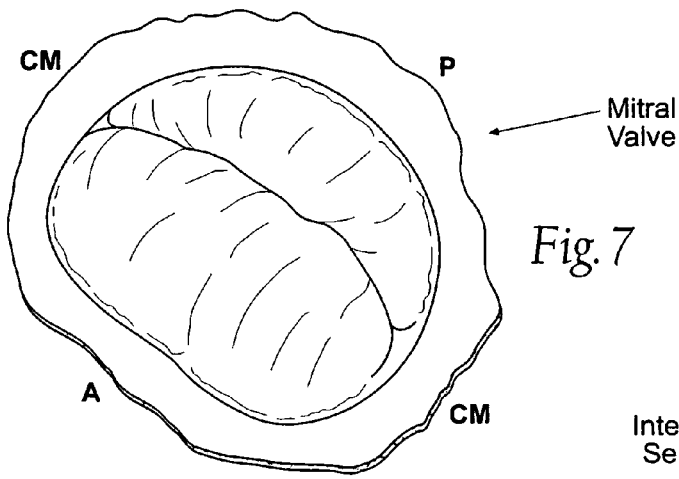
FIG. 7 is a superior view of a healthy mitral valve, with the leaflets closed and coapting at peak contraction pressures during ventricular systole.
Figure 8:
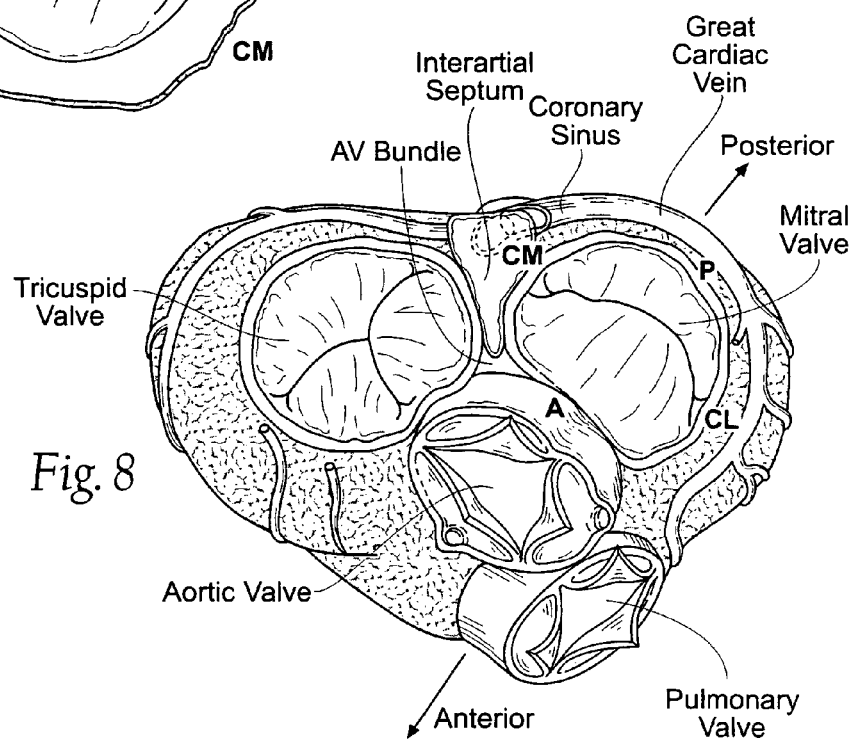
FIG. 8 is an anatomic superior view of a section of the human heart, with the normal mitral valve shown in FIG. 7 closed during ventricular systole (ventricular emptying) of the cardiac cycle.
Figure 9:
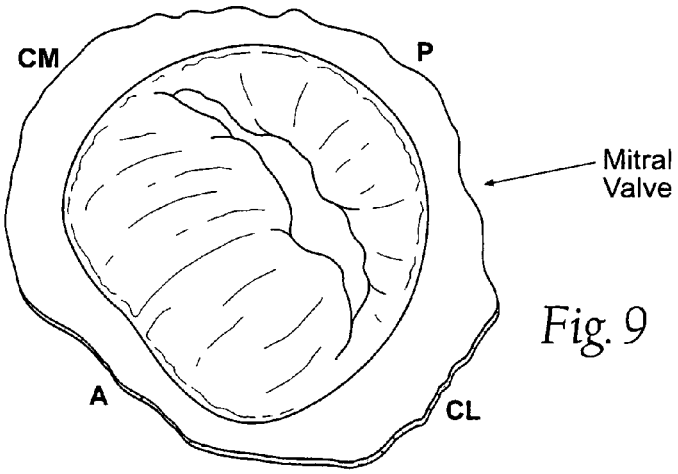
FIG. 9 is a superior view of a dysfunctional mitral valve, with the leaflets failing to coapt during peak contraction pressures during ventricular systole, leading to mitral regurgitation.
Figure 10A:
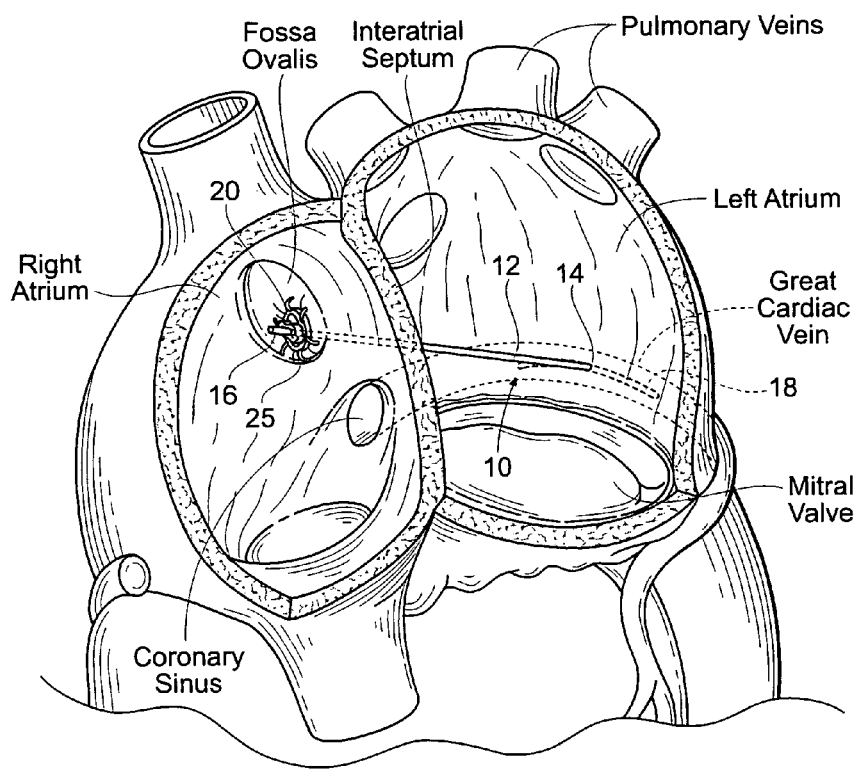
FIGS. 10A and 10B are anatomic anterior perspective views of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in an essentially straight path generally from a mid-region of the annulus.
Figure 10B:
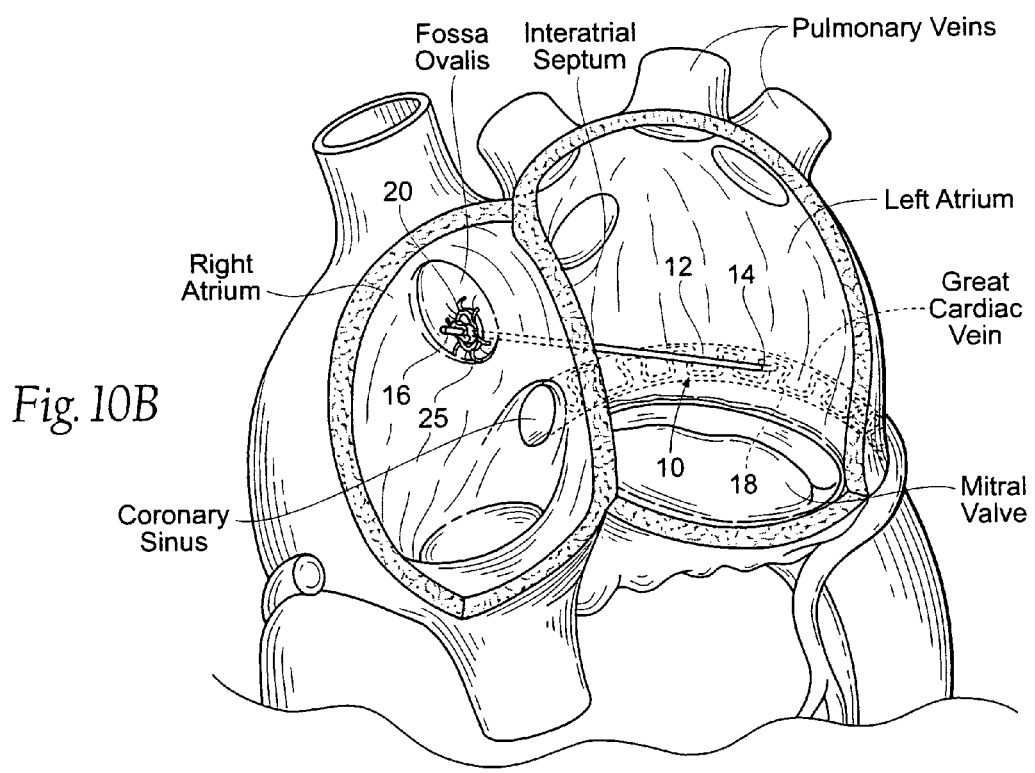

I. Trans-Septal Implants for Direct Shortening of the Minor Axis of a Heart Valve Annulus A. Implant Structure FIGS. 10A and 10B show embodiments of an implant 10 that is sized and configured to extend across the left atrium in generally an anterior-to-posterior direction, spanning the mitral valve annulus. The implant 10 comprises a spanning region or bridging element 12 having a posterior tissue anchoring region 14 and an anterior tissue anchoring region 16.

The posterior anchoring region 14 is sized and configured to be anchored in a region of atrial tissue above the posterior mitral valve annulus. This region is preferred, because it generally presents more tissue mass for obtaining purchase of the posterior anchoring region 14 than in a tissue region at or adjacent to the posterior annulus. Engagement of tissue at this supra-annular location also avoids encroachment of and risk of injury to the circumflex coronary artery.

The anterior anchoring region 16 is sized and configured to be anchored, upon passing into the right atrium through the septum, to tissue in or near the right atrium. For example, as is shown in FIGS. 10A and 10B, the anterior anchoring region 16 may be anchored to a region of fibrous tissue in the interatrial septum. As shown, the anchoring site is desirably superior to the anterior annulus at about the same elevation or higher than the elevation of the posterior tissue anchoring region 14. In the illustrated embodiment, the anterior anchoring region 16 is anchored at or near the inferior rim of the fossa ovalis. As will be described later, the anterior anchoring region 16 can be anchored at a more superior position in the septum, e.g., at or near the superior rim of the fossa ovalis. The anterior anchoring region 16 can also be anchored in a more superior or inferior position in the septum, away from the fossa ovalis, provided that the anchoring site does not harm the tissue region.

As will be described in greater detail later, in an alternative embodiment (see, e.g., FIGS. 33B and 33C), the anterior anchoring region 16, upon passing through the septum into the right atrium, may be anchored within or otherwise tethered to the superior vena cava (SVC) or the inferior vena cava (IVC), instead of to the septum itself.

In use, the spanning region or bridging element 12 can be placed into tension between the two tissue anchoring regions 14 and 16. The implant 10 thereby serves to apply a direct mechanical force generally in posterior to anterior direction across the left atrium. The direct mechanical force can serve to shorten the minor axis of the annulus. In doing so, the implant 10 can also reactively reshape the annulus along its major axis and/or reactively reshape other surrounding anatomic structures. It should be appreciated, however, the presence of the implant 10 can serve to stabilize tissue adjacent the heart valve annulus, without affecting the length of the minor or major axes.

It should be appreciated that, when situated in other valve structures, the axes affected may not be the "major" and "minor" axes, due to the surrounding anatomy. It should also be appreciated that, in order to be therapeutic, the implant 10 may only need to reshape the annulus during a portion of the heart cycle, such as during late diastole and early systole when the heart is most full of blood at the onset of ventricular systolic contraction, when most of the mitral valve leakage occurs. For example, the implant 10 may be sized to produce small or negligible displacement of the annulus to restore or enhance inward movement of the annulus during late ventricular diastolic relaxation, as the annulus dilates and becomes restricted by the implant 10.

The mechanical force applied by the implant 10 across the left atrium can restore to the heart valve annulus and leaflets a more normal anatomic shape and tension. The more normal anatomic shape and tension are conducive to coaptation of the leaflets during late ventricular diastole and early ventricular systole, which, in turn, reduces mitral regurgitation.

In its most basic form, the implant 10 is made from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization.

The implant 10 can be formed by bending, shaping, joining, machining, molding, or extrusion of a metallic or polymer wire form structure, which can have flexible or rigid, or inelastic or elastic mechanical properties, or combinations thereof. Alternatively, the implant 10 can be formed from metallic or polymer thread-like or suture material. Materials from which the implant 10 can be formed include stainless steel, nitinol, titanium, silicone, plated metals, eljiloy, and NP55.

The implant 10 can take various shapes and have various cross-sectional geometries. The implant 10 can have, e.g., a generally curvilinear (i.e., round or oval) cross-section, or a generally rectilinear cross section (i.e., square or rectangular), or combinations thereof.

1. The Posterior Anchoring Region

The posterior tissue anchoring region 14 is sized and configured to engage tissue within the left atrium at a supra-annular position, i.e., engaging tissue in the left atrium wall above the posterior annulus.

In the illustrated embodiment, the posterior anchoring region 14 is shown to engage tissue generally at the level of the great cardiac vein, which travels adjacent to and in parallel to the majority of the posterior mitral valve annulus. This tributary of the coronary sinus can provide a strong and reliable fluoroscopic landmark when a radiopaque device is placed within it or contrast dye is injected into it. As previously described, engagement of tissue at this supra-annular location also lessens the risk of encroachment of and risk of injury to the circumflex coronary artery compared to procedures applied to the mitral annulus directly.

The great cardiac vein also provides a site where relatively thin, non-fibrous atrial tissue can be readily augmented and consolidated. To enhance hold or purchase of the posterior tissue anchoring region 14 in what is essentially non-fibrous heart tissue, the posterior tissue anchoring region 14 can be coupled to a posterior anchor 18 placed within the great cardiac vein. This makes possible the mechanical fixation of the posterior anchoring region 14 in a non-fibrous portion of the heart in a manner that can nevertheless sustain appreciable hold or purchase on that tissue for a substantial period of time, without dehiscence, expressed in a clinically relevant time-frame.

In one embodiment (see FIG. 10A), the posterior anchor 18 comprises an integral part of the implant 10, being integrally joined to the posterior anchoring region 14 in a generally perpendicular relationship, forming a T-shape. In this arrangement, the posterior anchor 18 comprises the cross-arm of the T-shape. The posterior anchor 18 is elongated sufficiently to traverse inside at least a portion of the great cardiac vein in medial and lateral directions from the posterior anchoring region 14.

In this arrangement, the posterior anchor 18 can be inserted in a laid-back, collapsed condition upon the posterior anchoring region 14, through the lumen of a tissue piercing needle from the left atrium through a wall of the great cardiac vein. The posterior anchor 18 can be configured with an elastic memory such that, once free of the needle lumen, it springs open from the collapsed condition into the T-shape, to reside within the great cardiac vein. In this arrangement, the posterior anchor 18 can have a diameter of about 0.5 mm.

In the embodiment shown in FIG. 10B, the posterior anchor 18 comprises a separate structure to which the posterior anchoring region 14 is coupled during implantation. The coronary sinus provides an accessible intravascular site from the right atrium, through which the posterior anchor 18 of this type can be placed.

In the embodiment shown in FIG. 10B, the posterior anchor 18 comprises mechanical stent-like structure. The stent-like structure is desirably relatively large (e.g., at least 10 mm to 20 mm in diameter) to present a large physical and radiopaque target for the posterior anchoring region 14, or any other intra-atrial device attempting to enter or attach to an anchoring structure present within the great cardiac vein. The desired large physical size of the posterior anchor 18 further diminishes the likelihood of trauma to the circumflex coronary artery, in comparison to a situation where a smaller structure were placed in the great cardiac vein. A smaller physical target could be more readily missed, and trauma to surrounding tissues could result. Of course, a smaller structure (e.g., approaching 5 mm in diameter) or a larger structure (e.g., approaching 30 mm in diameter) could be selected for use, depending upon the particular therapeutic objectives that are intended.

It should be appreciated that non-fibrous tissue at, above, or below the level of the great cardiac vein, e.g., in a range of about 5 to about 25 mm above the plane of the posterior mitral valve annulus, can be strengthened and consolidated in other ways. For example, tissue bulking agents or fibrosis caused, e.g., chemically or by heat can be used to strengthen and consolidate regions of atrial tissue above the annulus for purchase or hold by the posterior tissue anchoring region 14.

2. The Anterior Anchoring Region

The anterior anchoring region 16 is sized and configured to engage firmly the fibrous tissue and the surrounding tissues in the right atrium side of the atrial septum. This fibrous tissue region provides a tissue fixation site of better integrity than muscle in terms of devices pulling through. The septum is the most fibrous tissue structure in its own extent in the heart. Surgically handled, it is usually one of the only heart tissues into which sutures actually can be placed and can be expected to hold without pledgetts or deep grasps into muscle tissue, where the latter are required.

As FIG. 10 shows, the anterior tissue anchoring region 16 passes through the septal wall at a supra-annular location above the plane of the anterior mitral valve annulus. The supra-annular distance on the anterior side can be generally at or above the supra-annular distance on the posterior side. As before pointed out, the anterior tissue anchoring region 16 is shown in FIG. 10 at or near the inferior rim of the fossa ovalis, although other more inferior or more superior sites can be used within or outside the fossa ovalis, taking into account the need to prevent harm to the septal tissue and surrounding structures.

By engaging tissue at this supra-annular level within the right atrium, which is fully outside the left atrium and spaced well above the anterior annulus, the implant 10 avoids the impracticalities of endovascular attachment at or adjacent to the anterior annulus, where there is just a very thin rim of annulus tissue that is bounded anteriorly by the anterior leaflet, inferiorly by the aortic outflow tract, and medially by the atrioventricular node of the conduction system. The anterior annulus is where the non-coronary leaflet of the aortic valve attaches to the mitral annulus through the central fibrous body. Anterior fixation of the implant 10 in the supra-annular level within the right atrium (either to the septum or in a vena cava) avoids encroachment of and risk of injury to both the aortic valve and the AV node.

The purchase of the anterior tissue anchoring region 16 in fibrous septal tissue is desirably enhanced by one or more anterior anchors 20. The anterior anchor or anchors 20 mechanically amplify the hold or purchase of the anterior anchoring region 16 in the fibrous tissue site. The anterior anchor or anchors 20 also desirably increase reliance, at least partly, on neighboring anatomic structures of the septum to anchor and fix the position of the implant 10. Anticipating that pinpoint pulling forces will be applied by the anchoring region 16 to the septum, the forces acting on the anchor 20 should be spread over a moderate area, without causing impingement on valve, vessels or conduction tissues. The anchor 20 should also have a low profile configuration and highly washable surfaces to diminish thrombus formation for devices deployed inside the heart. As will be described in greater detail later, a septal brace may be used in combination with the anterior anchor or anchors 20 to distribute forces uniformly along the septum (see FIG. 33A). Alternatively, stents in the IVC or the SVC can be used as anchoring sites (see FIGS. 33B and 33C), instead of anchoring directly to the septum.

Fixation of the posterior and anterior tissue anchoring regions 14 and 16 having radiopaque anchors and well demarcated fluoroscopic landmarks respectively at the supra-annular tissue sites just described, not only provides freedom from key vital structure damage—e.g., to the circumflex artery, AV node, and the left coronary and non-coronary cusps of the aortic valve—but the supra-annular fixation sites are also not reliant on purchase between tissue and direct tension-loaded penetrating/biting/holding tissue attachment mechanisms. Instead, physical structures and force distribution mechanisms like stents can be used, which better accommodate the attachment of mechanical levers and through which potential tissue tearing forces can be better distributed. Further, the fixation sites do not require the operator to use complex imaging. Adjustment of implant position after or during implantation is also facilitated, free of these constraints. The fixation sites also make possible full intra-atrial retrieval of the implant 10 by endovascularly snaring and then cutting the bridging element at either side of the left atrial wall, from which it emerges.

3. Orientation of the Spanning Region

In the embodiment shown in FIG. 10, the implant 10 is shown to span the left atrium beginning at a posterior point of anchorage superior to the approximate mid-point of the mitral valve annulus, and proceeding in an anterior direction in a generally straight path directly to the region of anterior anchorage in the septum. As shown in FIG. 10, the spanning region or bridging element 12 of the implant 10 is preformed or otherwise configured to extend in this essentially straight path above the plane of the valve, without significant deviation in elevation toward or away from the plane of the annulus, other than as dictated by any difference in elevation between the posterior and anterior regions of anchorage.

Lateral or medial deviations and/or superior or inferior deviations in this path can be imparted, if desired, to affect the nature and direction of the force vector or vectors that the implant 10 applies. It should be appreciated that the spanning region or bridging element 12 can be preformed or otherwise configured with various medial/lateral and/or inferior/superior deviations to achieve targeted annulus and/or atrial structure remodeling, which takes into account the particular therapeutic needs and morphology of the patient.

Figure 11:
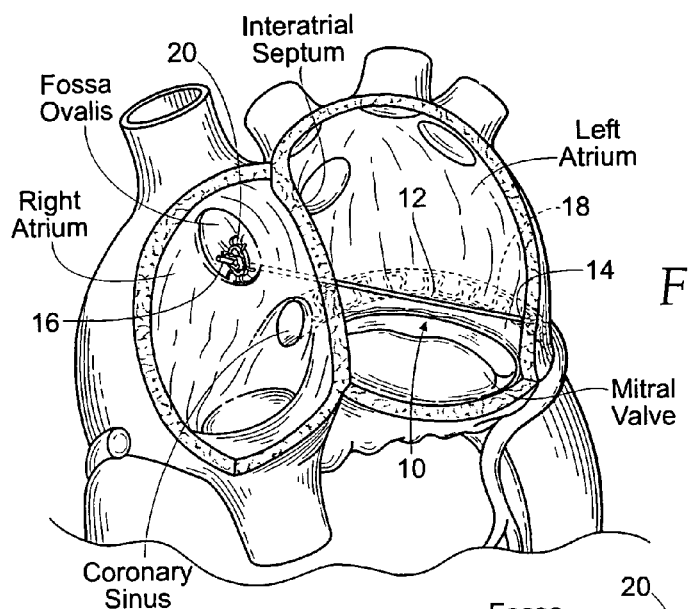
FIG. 11 is an anatomic anterior perspective view of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in an essentially straight path generally from a lateral region of the annulus.

For example, as shown in FIG. 11, the implant 10 is shown to span the left atrium beginning at a posterior region of anchorage that is closer to a lateral trigone of the annulus (i.e., farther from the septum). Alternatively, the posterior region of anchorage can be at a position that is closer to a medial trigone of the annulus (i.e., closer to the septum). From either one of these posterior regions of anchorage, the implant 10 can extend in an anterior direction in a straight path directly to the region of anterior anchorage in the septum. As shown in FIG. 11, like FIG. 10, the spanning region or bridging element 12 of the implant 10 is preformed or otherwise configured to extend in an essentially straight path above the plane of the valve, without significant deviation in elevation toward or away from the plane of the annulus, other than as dictated by the difference in elevation, if any, between the posterior and anterior regions of anchorage.

Figure 12:
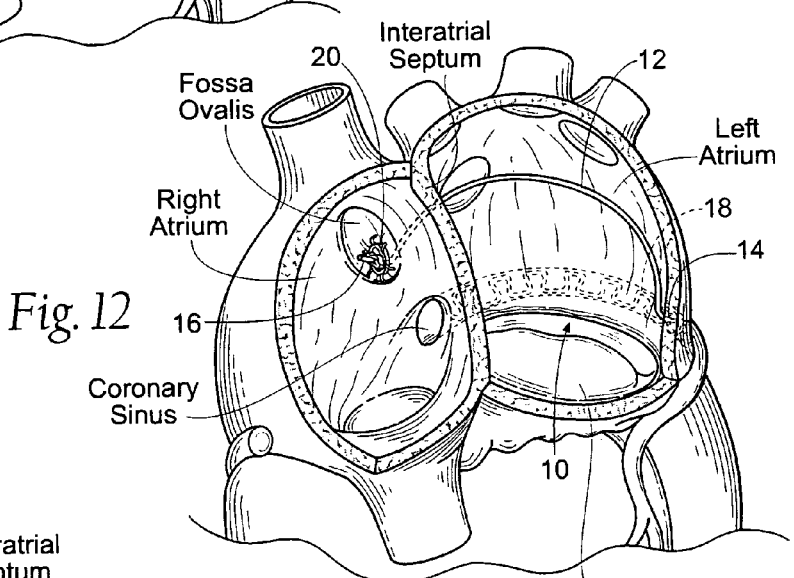
FIG. 12 is an anatomic anterior perspective view of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in an upwardly curved or domed path generally from a lateral region of the annulus.

Regardless of the particular location of the posterior region of anchorage (see FIG. 12), the spanning region or bridging element 12 of the implant 10 can be preformed or otherwise configured to arch upward above the plane of the valve toward the dome of the left atrium Alternatively (see FIG. 13), the spanning region or bridging element 12 of the implant 10 can be preformed or otherwise configured to dip downward toward the plane of the valve toward the annulus, extending close to the plane of the valve, but otherwise avoiding interference with the valve leaflets. Or, still alternatively (see FIG. 14), the spanning region or bridging element 12 of the implant 10 can be preformed or otherwise configured to follow a curvilinear path, bending around a trigone (medial or lateral) of the annulus before passage to the anterior anchorage region.

Figure 15:
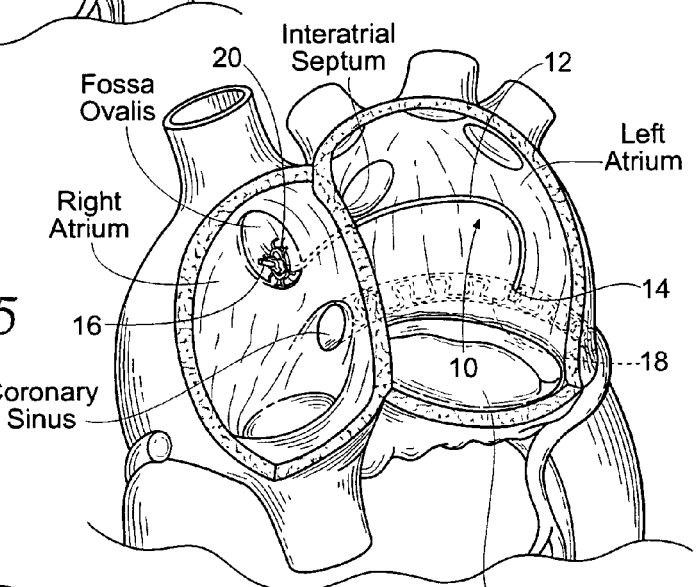
FIG. 15 is an anatomic anterior perspective view of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in a curvilinear path, bending around a trigone of the annulus generally from a mid-region region of the annulus, as well as elevating in an arch toward the dome of the left atrium.
Figure 16:
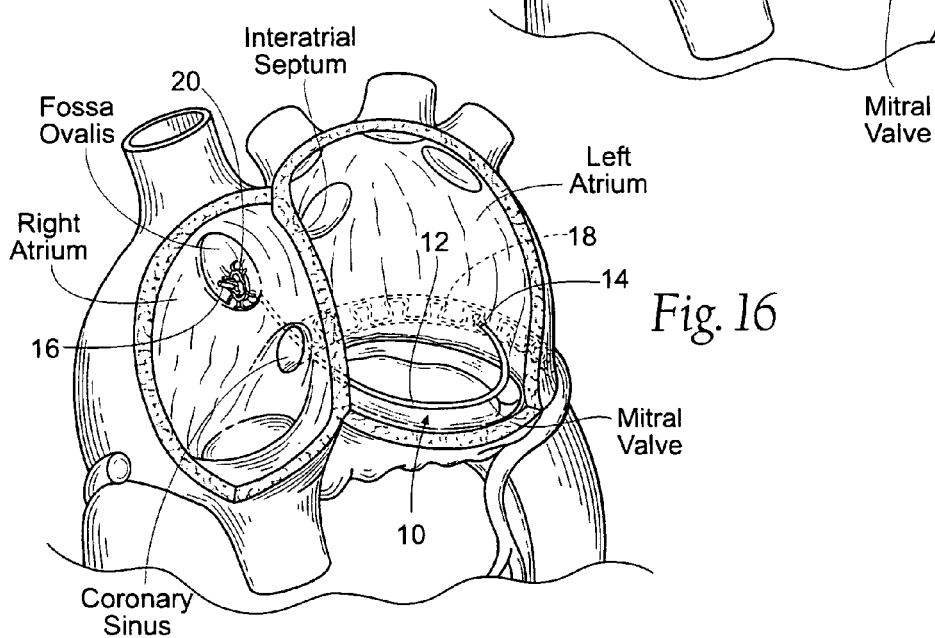
FIG. 16 is an anatomic anterior perspective view of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in a curvilinear path, bending around a trigone of the annulus generally from a mid-region region of the annulus, as well as dipping downward toward the plane of the valve.

Various combinations of lateral/medial deviations and superior/inferior deviations of the spanning region or bridging element 12 of the implant 10 are of course possible. For example, as shown in FIG. 15, the spanning region or bridging element 12 can follow a curvilinear path bending around a trigone (medial or lateral) of the annulus as well as elevate in an arch away from the plane of the valve. Or, as shown in FIG. 16, the spanning region or bridging element 12 can follow a curvilinear path bending around a trigone (medial or lateral) of the annulus as well as dip toward the plane of the valve.

Figure 17:
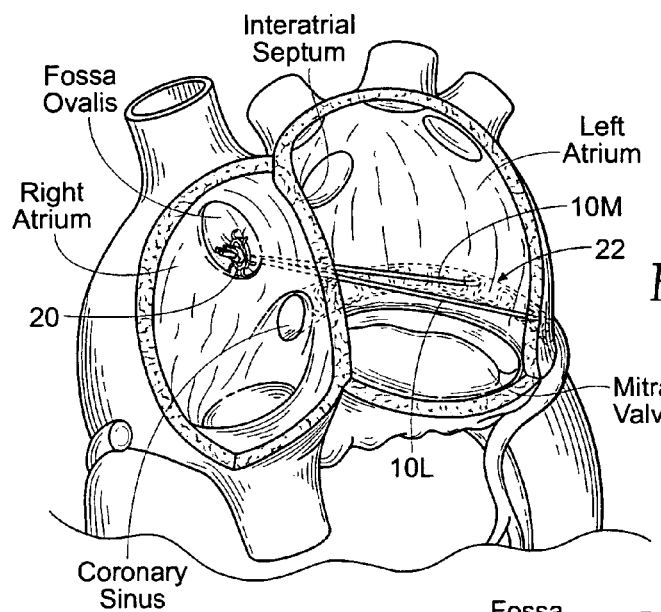
FIG. 17 is an anatomic anterior perspective view of the left and right atriums, with portions broken away and in section to show the presence of an implant system that includes two inter-atrial bridging elements that span the mitral valve annulus, each with a posterior region anchored in the great cardiac vein and an anterior region anchored on the interatrial septum, the inter-atrial bridging elements both extending in generally straight paths from different regions of the annulus.

Regardless of the orientation, more than one implant 10 can be installed to form an implant system 22. For example, FIG. 17 shows a system 22 comprising a lateral implant 10L and a medial implant 10M of the types previously described. FIG. 17 shows the implants 10L and 10M being fixed at a common anterior anchorage region. It should be appreciated that the implants 10L and 10M can include spaced apart anterior anchorage regions.

Figure 13:
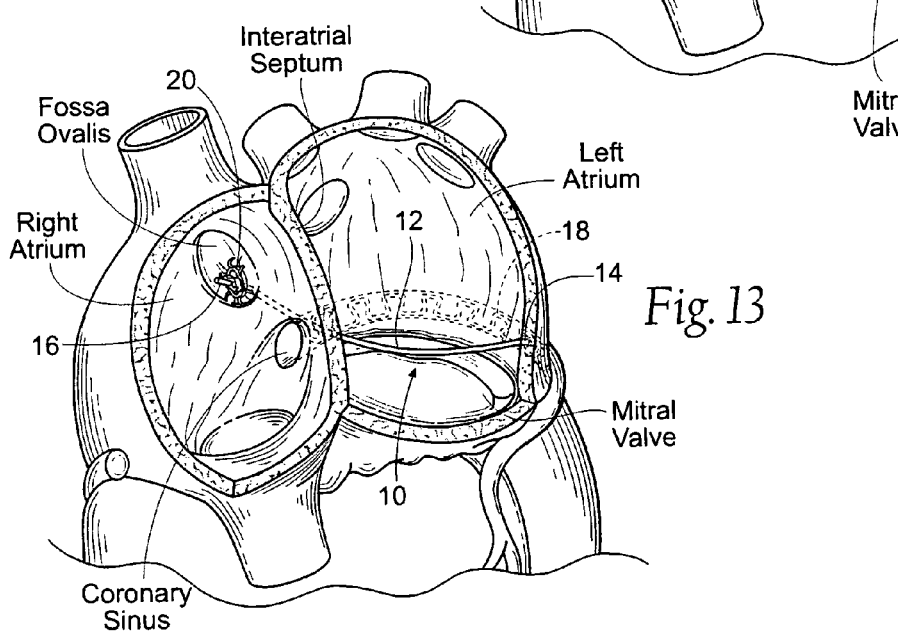
FIG. 13 is an anatomic anterior perspective view of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in a downwardly curved path generally from a lateral region of the annulus.

One or both of the implants 10L and 10M can be straight (as in FIG. 11), or arch upward (as in FIG. 12), or bend downward (as in FIG. 13). A given system 10 can comprise lateral and medial implants 10L and 10M of different configurations. Also, a given system 22 can comprise more than two implants 10.

Figure 14:
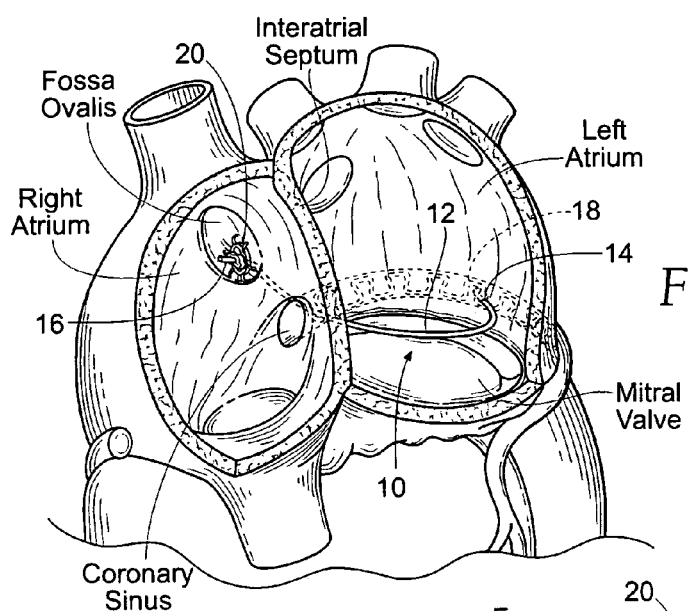
FIG. 14 is an anatomic anterior perspective view of the left and right atriums, with portions broken away and in section to show the presence of an implant system that includes an inter-atrial bridging element that spans the mitral valve annulus, with a posterior region anchored in the great cardiac vein and an anterior region anchored on the interatrial septum, the inter-atrial bridging element extending in a curvilinear path, bending around a trigone of the annulus generally from a mid-region region of the annulus.
Figure 18:
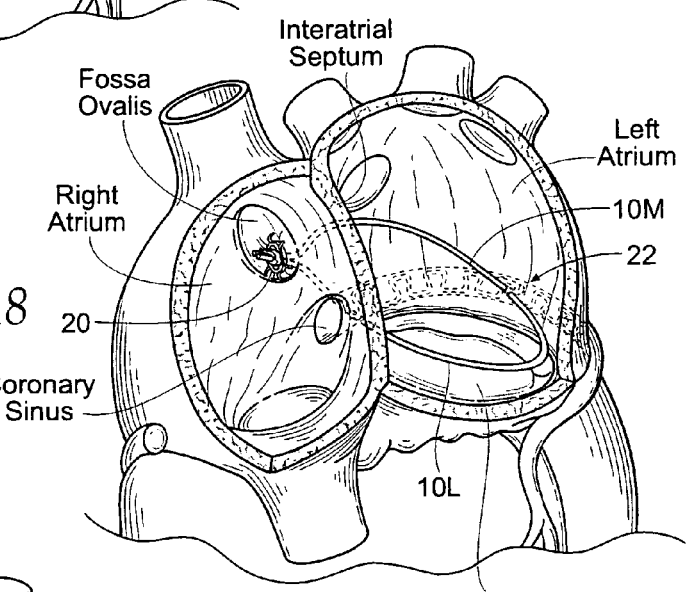
FIG. 18 is an anatomic anterior perspective view of the left and right atriums, with portions broken away and in section to show the presence of an implant system that includes two inter-atrial bridging elements that span the mitral valve annulus, each with a posterior region anchored in the great cardiac vein and an anterior region anchored on the interatrial septum, the inter-atrial bridging elements both extending in generally curvilinear paths from adjacent regions of the annulus.

FIG. 18 shows a system 22 comprising two curvilinear implants 10L and 10M of the type shown in FIG. 14. In FIG.

18, the curvilinear implants 10L and 10M are shown to be anchored at a common posterior anchorage region, but the implants 10 can proceed from spaced apart posterior anchorage regions, as well. One or both of the curvilinear implants 10L and 10M can be parallel with respect to the plane of the valve (as in FIG. 14), or arch upward (as in FIG. 15), or bend downward (as in FIG. 16). A given system 22 can comprise curvilinear implants 10L and 10M of different configurations.

Figure 19:
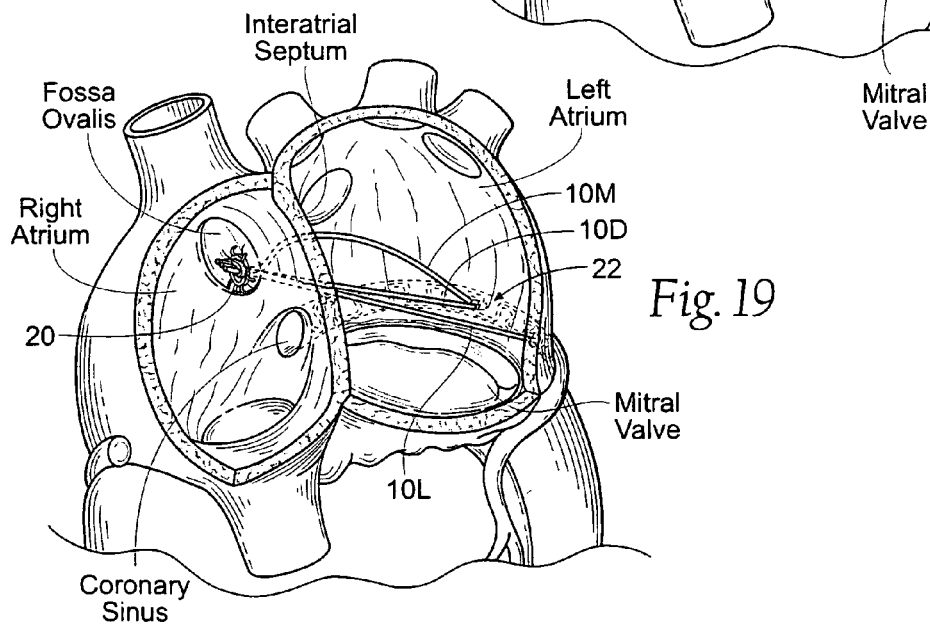
FIG. 19 is an anatomic anterior perspective view of the left and right atriums, with portions broken away and in section to show the presence of an implant system that includes three inter-atrial bridging elements that span the mitral valve annulus, each with a posterior region anchored in the great cardiac vein and an anterior region anchored on the interatrial septum, two of the inter-atrial bridging elements extending in generally straight paths from different regions of the annulus, and the third inter-atrial bridging elements extending in a generally curvilinear path toward a trigone of the annulus.

FIG. 19 shows a system 22 comprising a direct middle implant 10D, a medial curvilinear implant 10M, and a direct lateral implant 10L. One, two, or all of the implants 10 can be parallel to the valve, or arch upward, or bend downward, as previously described.

B. Anchoring Elements

1. Within the Great Cardiac Vein

As before explained, the posterior tissue anchoring region 14 desirably includes one or more posterior anchors 18 placed in the great cardiac vein to enhance its purchase in supra-annular tissue in the left atrium.

The posterior anchor 18 can be variously constructed. The anchor 18 may be rigid, or flexible, or elastic, or malleable, or solid, or porous. The anchor 18 can sized and configured to provide a localized anchoring site, or be elongated and extend medially and laterally from the intended anchoring site to better consolidate atrial tissue at the level of the vein along the length of the vein.

Figure 20:
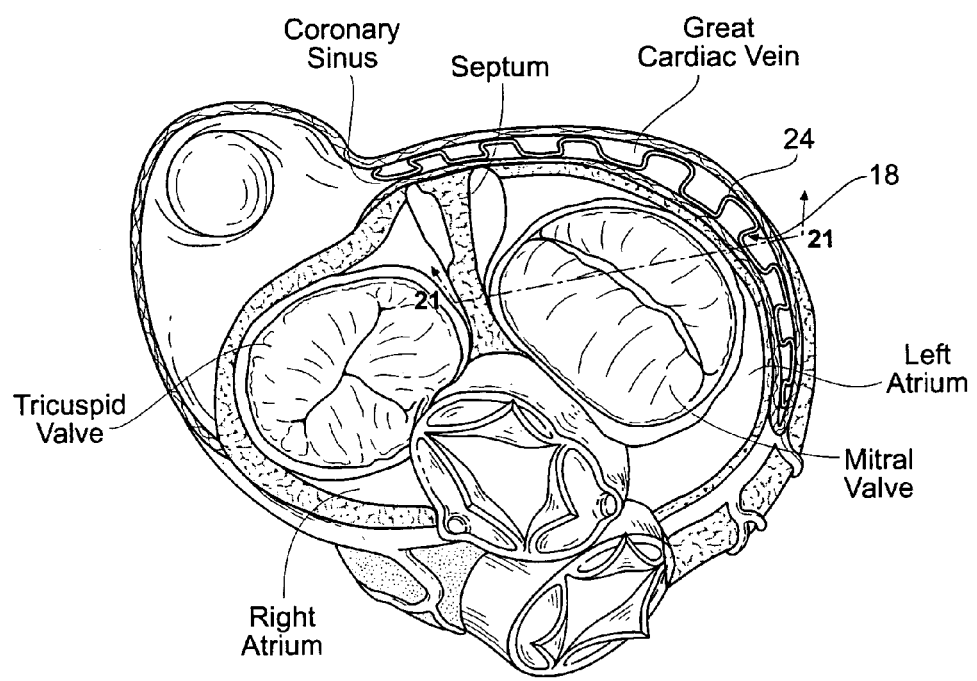
FIG. 20 is an anatomic superior view of a section of the human heart, showing the presence of a posterior anchor structure within the great cardiac vein, to which a posterior region of an implant as shown in FIGS. 10B and 11 to 19 can be attached during use.

As shown in FIG. 20, the anchor 18 can comprise a stent-like structure 24 that is sized and configured to be introduced into the great cardiac vein, e.g., through the coronary sinus os in the right atrium (as will be described in greater detail later). The structure 24 can comprise an expandable scaffold, which can take the form of a self-expanding stent, or a malleable structure that is expanded by means of an interior force, e.g., a balloon. The structure 24 can be flexible, or semi-rigid, or rigid, or have regions of different mechanical characteristics.

Alternatively, the anchor 18 can comprise a preformed, non-expandable hollow tube or solid rod of a pre-determined shape, which is sized and configured to be advanced into the great cardiac vein. Still alternatively, the anchor 18 can comprise an inert biocompatible bulking material injected into the vein, which cures to possess a desired mechanical property. Or, the anchor 18 can include a hollow structure that is at least a partially-filled with an inert biocompatible material, which cures to possess a desired mechanical property.

Regardless of the particular configuration, the anchor 18 is desirably radio-opaque or incorporates radio-opaque features to facilitate fluoroscopic visualization when positioned in a tributary of the coronary sinus.

Figure 21:
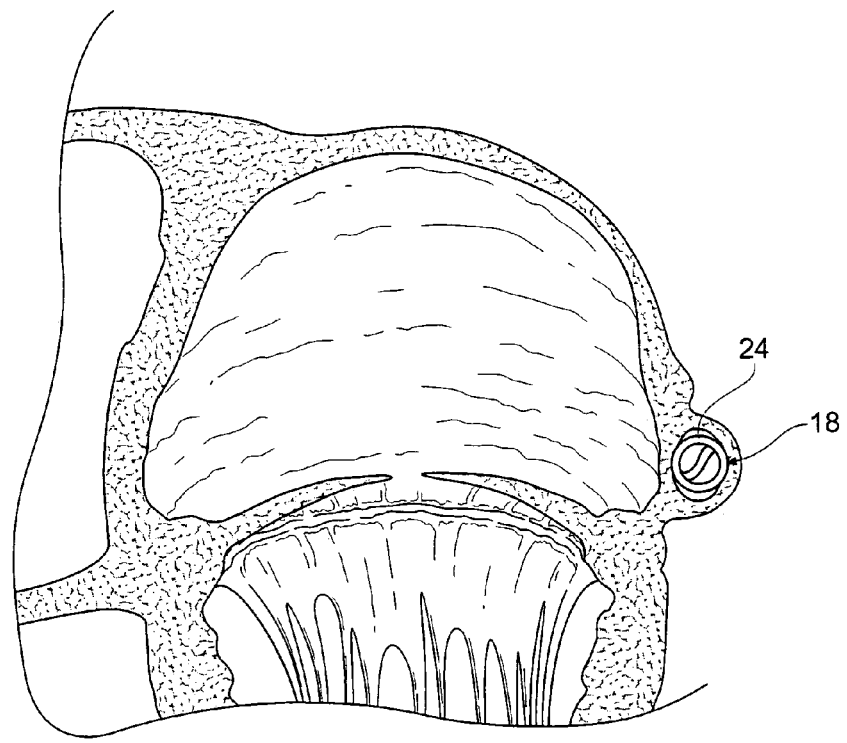
FIG. 21 is an anatomic section view of the posterior anchor structure taken generally along line 21-21 in FIG. 20.
Figure 22:
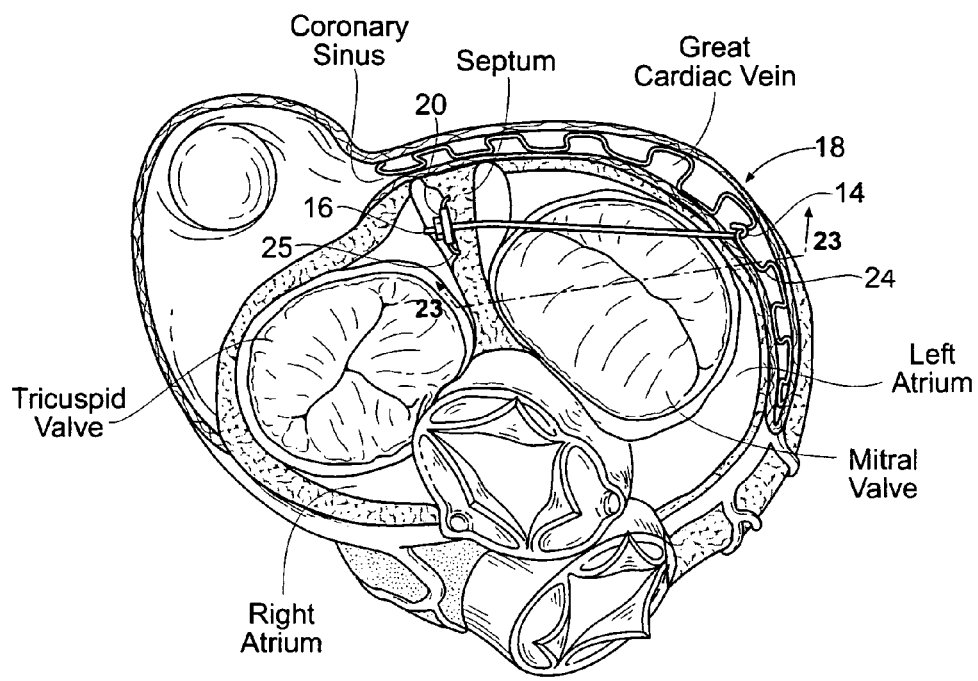
FIG. 22 is an anatomic superior view of a section of the human heart, showing the presence of a posterior anchor structure within the great cardiac vein, to which a posterior region of an implant as shown in FIG. 10B is attached as it would be during use.
Figure 23:
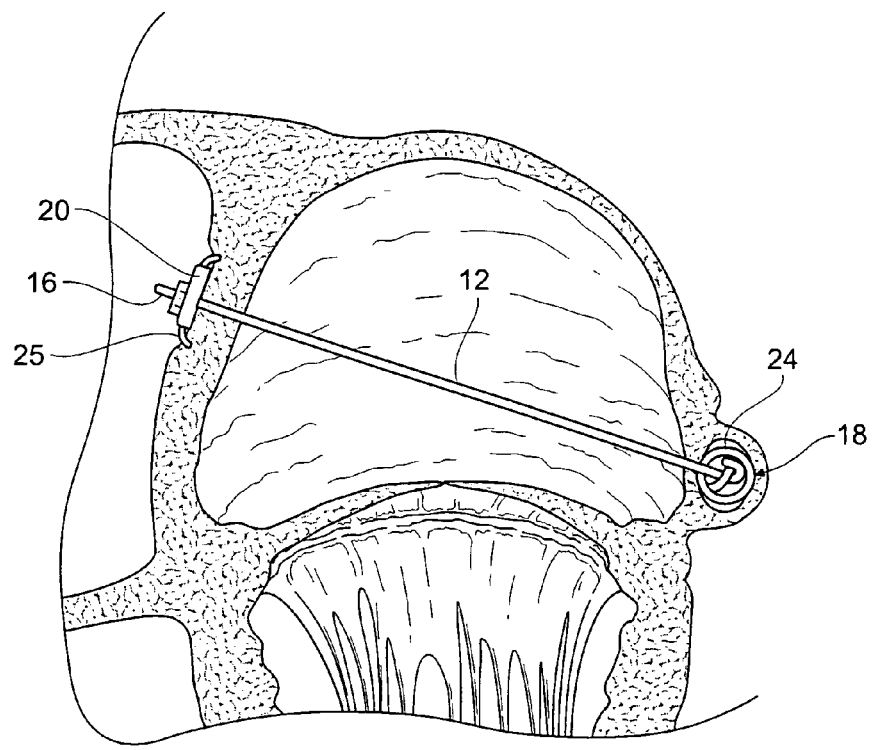
FIG. 23 is an anatomic section view of the posterior anchor structure and implant taken generally along line 21-21 in FIG. 22.

As FIG. 21 shows, the anchor 18 may be held in position within the vein by gripping the surrounding vessel wall, e.g., by barbs, tines, or the like. If desired, the anchor 18 may be further secured by suture, adhesive, or like material within the vein. The anchor 18 can incorporate roughened or porous surfaces and/or be coated with or allow injection of other materials (e.g., polyester fabric, irritative agents, or drug agents) to promote tissue in-growth. To enhance fibrosis and potentially diminish the likelihood of tissue dehiscence in and around the great cardiac vein at the time the anchoring region 14 is used, the anchor 18 may be placed within the great cardiac vein a number of weeks in advance of the anchoring region 14. The number of weeks may vary, but a majority of patients may be expected to have some healing by four weeks as a minimum. In this arrangement (see FIGS. 22 and 23), the posterior anchoring region 14 is sized and configured to be manipulated within the left atrium outside the vein, and to lock into or otherwise gain purchase with the anchor 18 that resides within the vein. For example, the posterior anchoring region 14 can comprise a hook or T-shaped structure that locks from outside the vein into the material or structure of the anchor 18 residing within the vein. Alternatively, as shown in FIG. 10A, if the integrated cross-arm of the T is elongated to the extent that it traverses inside the coronary venous system along a sufficient length of the great cardiac vein, the cross-arm can itself serve as the anchor 18 with a separately deployed structure. Alternatively, the posterior anchoring region 14 (or the entire implant 10, for that matter) can comprise suture material that is threaded from outside the vein through the material or structure of the anchor 18 residing within the vein.

2. Anchoring to Fibrous Septal Tissue

The anterior anchoring region 16 is sized and configured to pass through the septum and project into the right atrium. There, the anterior anchor 20 captures the anterior anchoring region 16 and holds the anchoring region 16 against the fibrous and surrounding muscular tissue of the septum in the right atrium.

The anterior anchor 20 can be variously constructed. In the illustrated embodiment (see, e.g., FIGS. 10, 22, and 23), the anterior anchor 20 takes the form, fit, and function of an anchor button that is secured to the anterior anchoring region. The anchor button 20 includes barbed stays 25 that brace against the septum. The stays 25 can be crimped to the anterior anchoring region 16 to maintain a desired degree of tension on the spanning region or bridging element 12 within the left atrium. An anchor button 22 can be located only on the right atrium side of the septum, or both left and right atrium sides of the septum.

Alternatively, the anterior anchoring region 16 (or the entire implant 10, for that matter) can comprise suture material that is threaded through the fibrous wall of the septum, with or without the use of an anchor button or the like. In the latter case a more proximal vena caval anchor would supplant the need for using the inter-atrial septum as an anchor.

As will be described later, the anchoring site can be within either the SVC or IVC, instead of to the septum.

C. Implantation

The implants 10 or implant systems 22 as just described lend themselves to implantation in a heart valve annulus in various ways. The implants 10 or implant systems 22 can be implanted, e.g., in an open heart surgical procedure. Alternatively, the implants 10 or implant systems 22 can be implanted using catheter-based technology via a peripheral venous access site, such as in the femoral or jugular vein or femoral artery (via the IVC or SVC) under image guidance, or trans-arterial retrograde approaches to the left atrium through the aorta also under image guidance.

Alternatively, the implants 10 or implant systems 22 can be implanted using thoracoscopic means through the chest, or by means of other surgical access through the right atrium, also under image guidance.

Image guidance includes but is not limited to fluoroscopy, ultrasound, magnetic resonance, computed tomography, or combinations thereof.

FIGS. 24 to 30 show a representative embodiment of the deployment of an implant 10 of the type shown in FIG. 10 by a percutaneous, catheter-based procedure, under image guidance.

Figure 24:
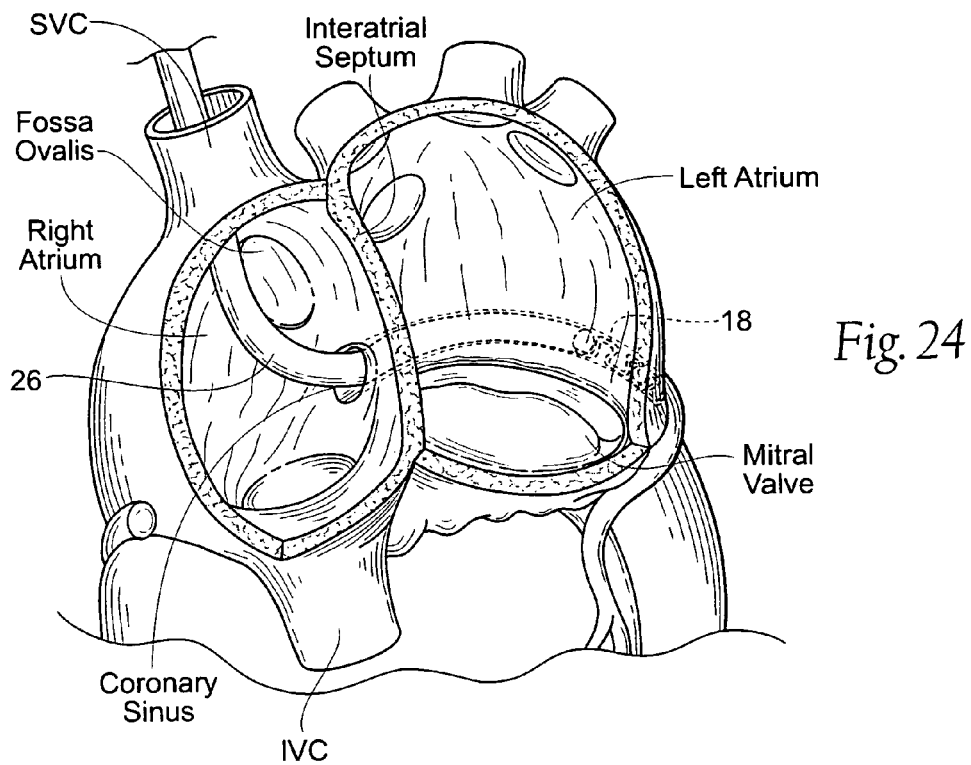
FIGS. 24 to 30 are anatomic views depicting representative catheter-based devices and steps for implanting an implant system of the type shown in FIG. 10B.

Percutaneous vascular access is achieved by conventional methods into the femoral or jugular vein. As FIG. 24 shows, under image guidance, a first catheter 26 is steered through the vasculature into the right atrium. It is the function of the first catheter 26 to deploy the posterior anchor 18 into the great cardiac vein through the coronary sinus. Catheter access to the coronary sinus can be achieved through either a femoral vein to IVC or SVC route (in the latter case, for a caval brace) or an upper extremity or neck vein to SVC or IVC route (in the latter case, for a caval brace). In the case of the SVC, the shortest access is from the upper extremity or neck venous system; however, the IVC can also be access by passing through the SVC and right atrium. Similarly the shortest access to the IVC is through the femoral vein; however the SVC can also be access by passing through the IVC and right atrium. FIGS. 24 to 30 show access through a SVC route for purposes of illustration. In a later described implantation technique (see FIGS. 36 to 39), access though an IVC route is shown for purposes of illustration.

The first catheter 26 advances the anchor 18, e.g., through the coronary sinus os in the right atrium, into the great cardiac vein above and in parallel to the posterior mitral valve annulus. A guide wire (not shown) may be used to guide the advancement. The anchor 18 is extended to a length sufficient to accommodate the desired site of fixation for the posterior anchoring region 14 of the implant 10. The length of the posterior anchor may extend from 20 mm to 200 mm as it lies inside the coronary venous system. The desired position of the posterior anchor 18 can be secured, e.g. by self-expansion or the use of a balloon to cause expansion within the vein, or it may require no conformational change from its shape inside the delivery catheter.

Figure 25:
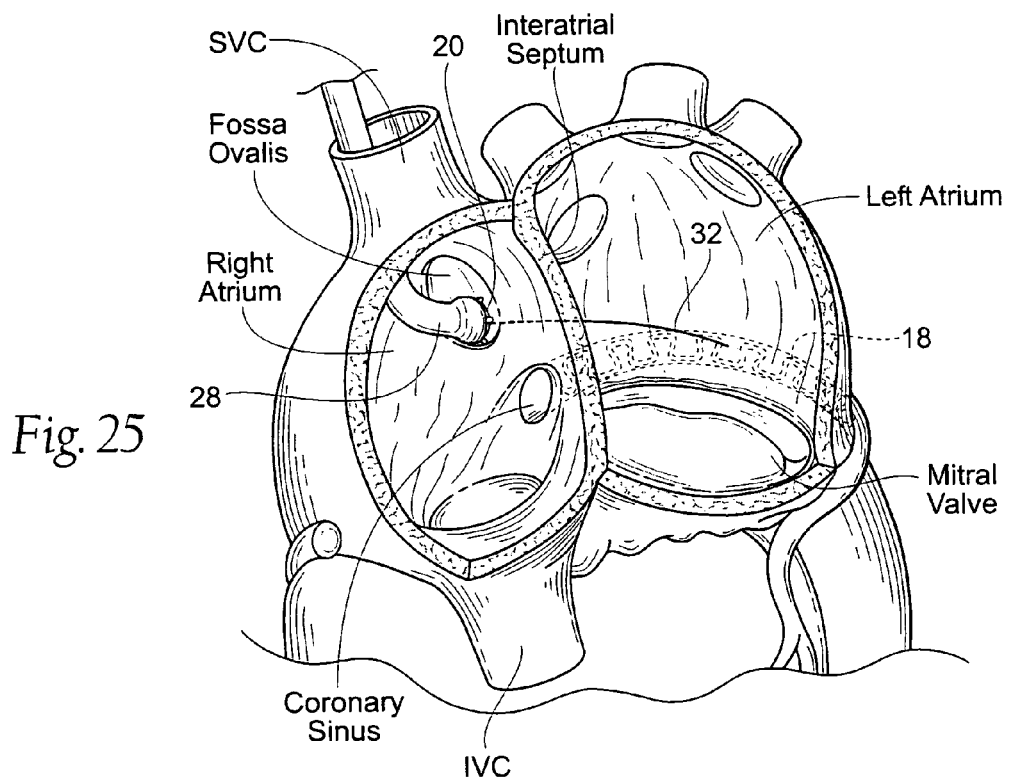

As FIG. 25 shows, upon securing the position of the posterior anchor 18 within the vein, the first catheter 26 is withdrawn (the guide wire, if used, may be left inside the posterior anchor 18 within the coronary vein), and a second catheter 28 is steered through the vasculature into the right atrium. The second catheter 28 carries the anterior anchor 20, which it fixes to the septum. The second catheter 28 also carries a distal needle (not shown), which is deployed to pierce the septum between the right and left atrium. In FIG. 25, the needle pierces the fossa ovalis near its inferior rim. The fossa ovalis is selected because it constitutes a safe structure to traverse and has an anatomic landmark that can be readily accessed by conventional intravascular techniques and pierced for the purpose of gaining access to the left atrium from the right atrium through the septum. Catheter access to the fossa ovalis can be achieved through either a femoral-IVC or internal jugular-SVC route (a femoral-SVC route is shown simply for purposes of illustration). As FIG. 25 shows, once access between the right and left atriums is opened, a guide wire 32 is advanced trans-septally through the needle catheter 28 into the left atrium.

Figure 26A:
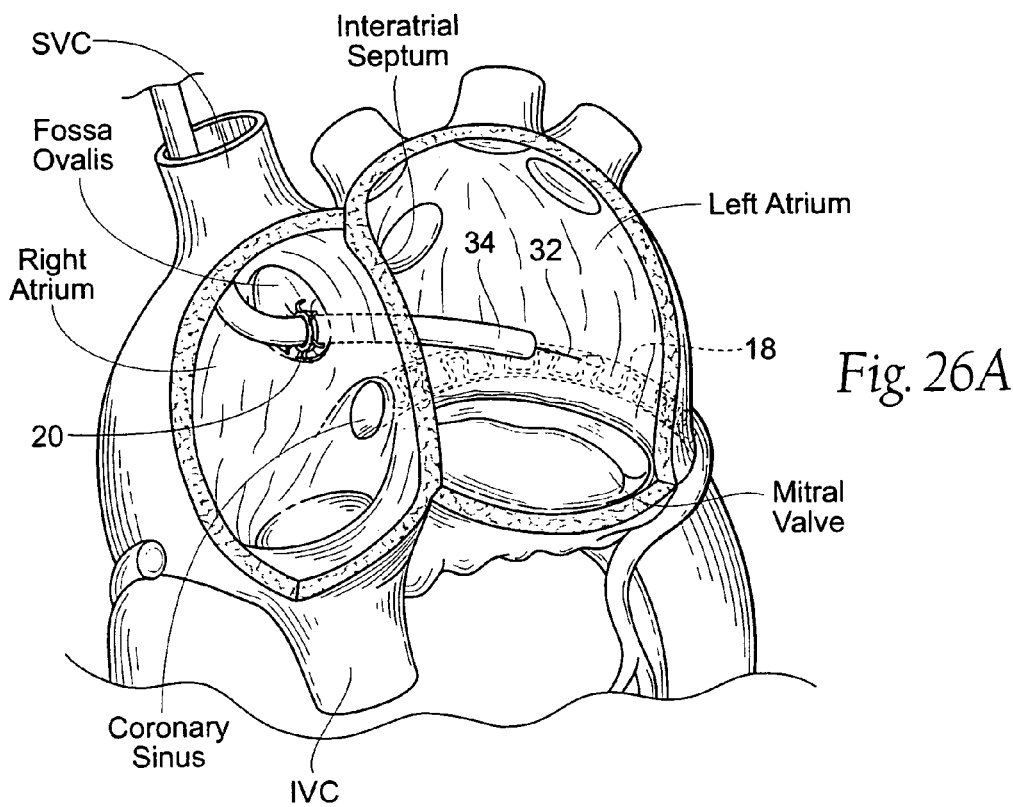
Figure 26B:
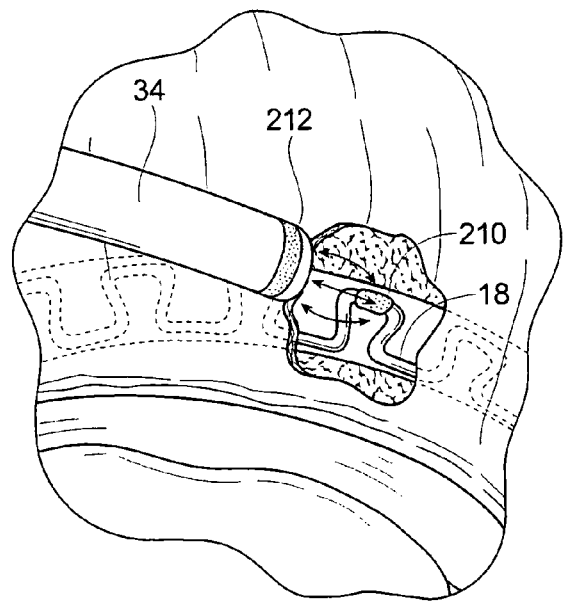

The second catheter 28 is withdrawn (FIG. 26A shows its absence). Under image guidance, an implant delivery catheter 34 is advanced over the guide wire 32 trans-septally through the fossa ovalis puncture (through the already delivered anchor 20, which is attached there) and into the left atrium. Alternatively, the implant delivery catheter 34 can be deployed trans-septally by means of surgical access through the right atrium.

Under image guidance, the implant delivery catheter 34 is directed to a targeted posterior anchoring site at the level where the posterior anchor 18 resides within the great cardiac vein. The implant delivery catheter 34 can include an onboard distal steering mechanism, to direct the catheter 34 to the intended site with image guidance. Alternatively, or in combination (see FIG. 26B), the anchor 18 residing within the great cardiac vein can carry one or more magnetic elements 210 along its length (either as part of the anchor 18 or within a separately delivered catheter that temporarily supplies the magnetic force required), which coincide with the targeted anchoring site(s). In this arrangement, the distal end of the implant delivery catheter 34 can include a magnetic element 212 or soft ferromagnetic material that is magnetically attracted to the magnetic element within the great cardiac vein at the intended anchoring site.

Figure 27A:
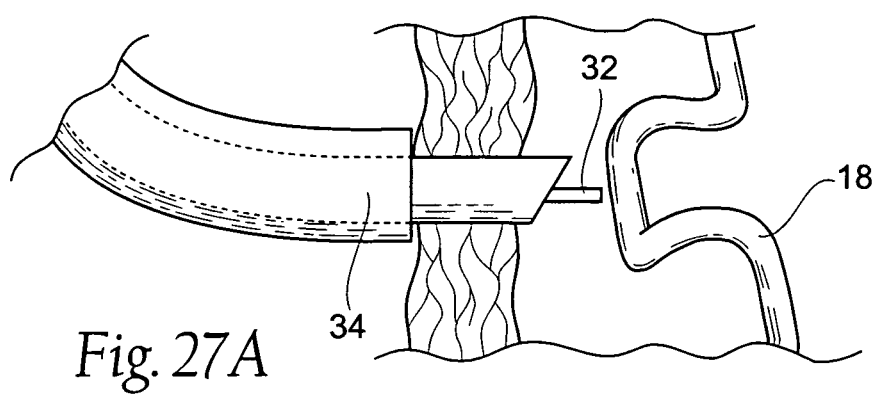
Figure 27B:
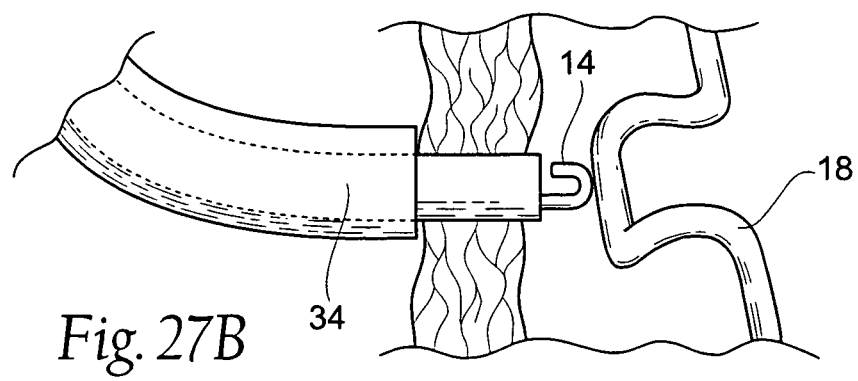
Figure 27C:
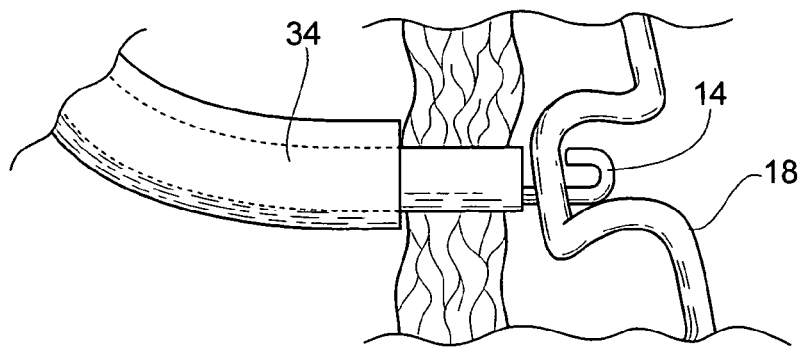

Once the implant delivery catheter 34 has located the targeted anchoring site (see FIG. 27A), the implant delivery catheter 34 is manipulated by imagining, magnetic guidance catheter or other means described in the present invention or in standard interventional or surgical practice, to puncture atrial tissue at the anchoring site into the great coronary vein. The posterior anchoring region 14 of the implant 10 is advanced from the implant delivery catheter 34 into the great cardiac vein (as FIG. 27B shows) to attach to the posterior anchor 18 that resides there, as illustrated in this case with a hooking attachment locking mechanism (as FIG. 27C shows). Alternatively, the anchoring region 14 can include a grasper that grasps through tissue and into a strut of the posterior anchor 18 inside the great cardiac vein to gain attachment.

Figure 28:
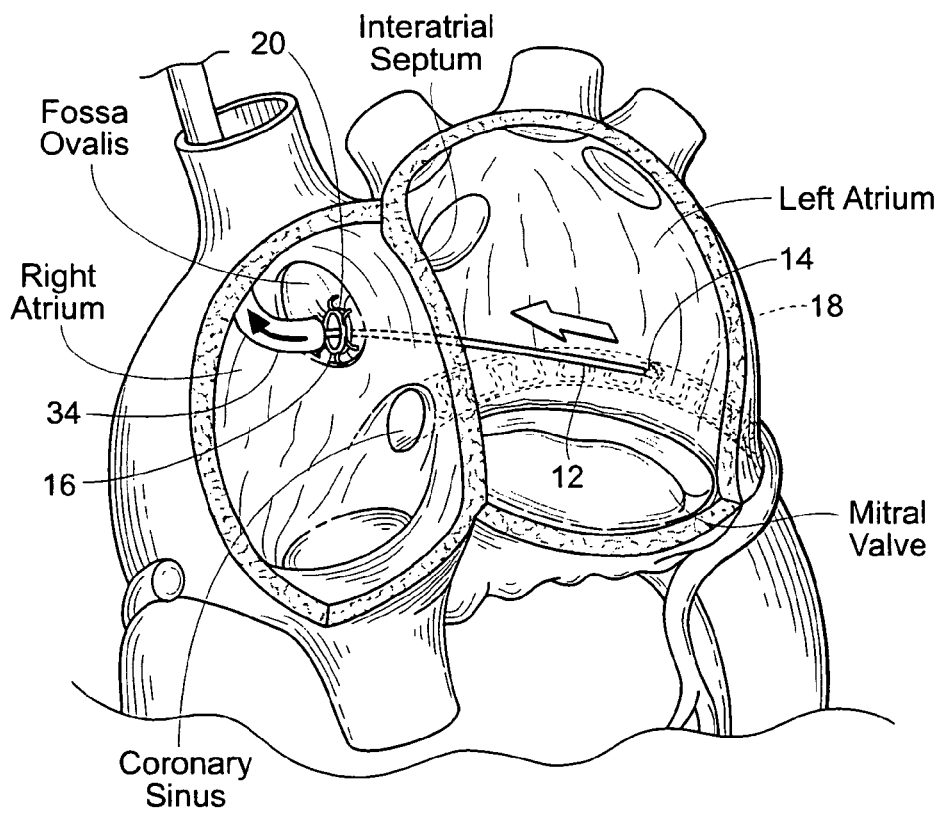

As FIG. 28 shows, once attachment between the posterior anchoring region 14 and the posterior anchor 18 is made, the implant delivery catheter 34 is drawn out of the great cardiac vein and anteriorly across the left atrium. The spanning region or bridging element 12 of the implant 10 is thereby deployed from the catheter 34 within the left atrium. In this way, the anterior anchoring region 16 is lead back through the septum and into the right atrium.

Figure 29:
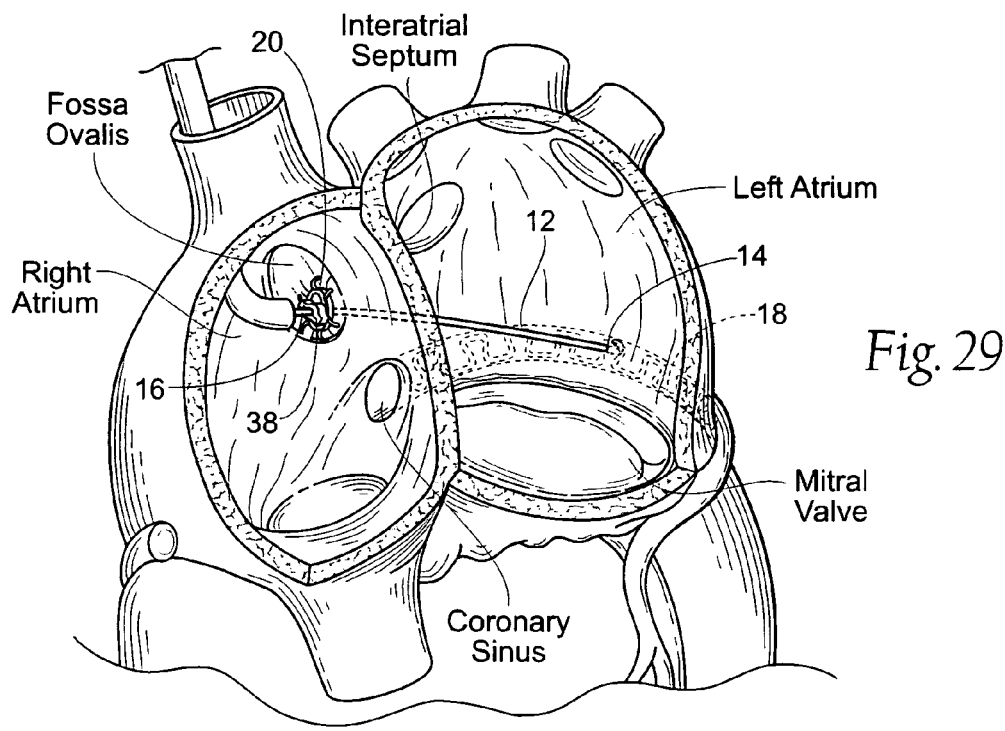

As FIG. 29 shows, the implant delivery catheter 34 can exert a pulling force on the spanning element or bridging element 12 as it slides through the already attached anterior anchoring region 16 from within the right atrium, to place the spanning region or bridging element 12 in a desired amount of tension. Alternatively, anterior anchoring region 16 can be released from the implant delivery catheter 34 and a suitable grasping instrument (for example, a 7 French grasper) can be deployed in the right atrium to take hold of the anchoring region 16 in the right atrium to place the spanning region 12 in a desired amount of tension, while the anterior anchoring region 16 is slid forward by the guiding catheter to achieve the proper tensioning. Various other surgical techniques and manipulations can be employed to place the spanning element 12 into tension. For example, the anterior anchor 16 can include a cinch release mechanism, which can be snipped with a cutting tool and another anchor threaded over the proximal wire component of the bridging or spanning element 12. The latter is snipped when adjustments have been finalized.

Regardless of the surgical manipulation and/or instrumentation used, pulling inwardly toward the left atrium on the anterior anchoring region 16 (either from within the right atrium by means of the implant delivery catheter 34 or a separate gripping tool) exerts a pulling force on posterior atrial tissue in the region where the posterior anchoring region 14 is attached to the posterior anchor 18. The pulling force draws the posterior atrial tissue inwardly toward the anterior atrial tissue of the left atrium. The existence of the elongated posterior anchor 18 serves to consolidate the length of the great cardiac vein, thereby distributing the pulling force laterally and medially. The pulling force can serve to shorten the annulus along its minor axis. The presence of the anchor 18 within the great cardiac vein consolidates the length of the great cardiac vein into a unitary physical structure, which, when pulled upon at least at one point, serves to compress the whole posterior annulus.

The physician can elect to monitor the incidence of mitral regurgitation by various conventional means, e.g., by contrast ventriculography or by echocardiographic Doppler assessment, as tension is progressively applied to the implant 12. If the physician chooses this approach, the physician can dynamically adjust tension on the implant 12 to achieve a desired diminution or elimination of the incidence or mitral regurgitation.

Figure 30:
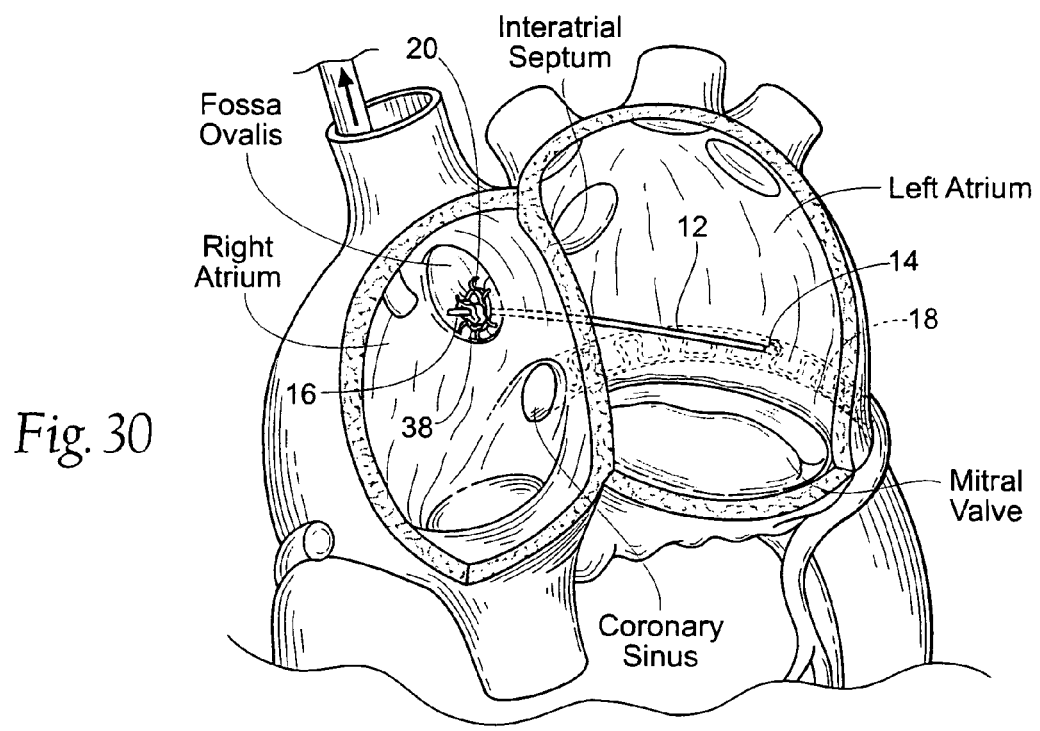

As FIG. 29 shows, once the implant 12 is satisfactorily positioned and/or the desired therapeutic result is achieved, the physician introduces a tool 36 that crimps a clip 38 or a functionally equivalent mechanism to the anterior anchoring region 16, to hold fast the anterior anchoring region 16 to the anchor button 20. Alternatively, the anterior anchoring region 16 can be threaded, and a nut delivered and threaded to the region 16 to retain the anterior anchoring element 16 in the desired degree of tension. As FIG. 30 shows, the anterior anchoring region 16 is cut next to clip 38 (or nut), ending the installation, and the intravascular tool or tools are withdrawn.

The projection of the anterior anchoring region 16 into the right atrium facilitates repositioning, retensioning, and/or retrieval of the implant 12 from the right atrium, if necessary or desired.

II. Implant Systems for Achieving Mitral Annulus Unloading

A. System Overview

The trans-septal embodiments just described with straight or linear bridging elements apply a main force vector that is directed essentially across the left atrium (i.e., at about a fifteen to less than forty-five degree vector above the horizontal) from a posterior region above the mitral valve annulus to an anterior septal tissue region, which is also above the mitral valve annulus. Use of the implant 10 or implant system 22 for this purpose can provide significant amelioration of mitral regurgitation.

Figure 31:
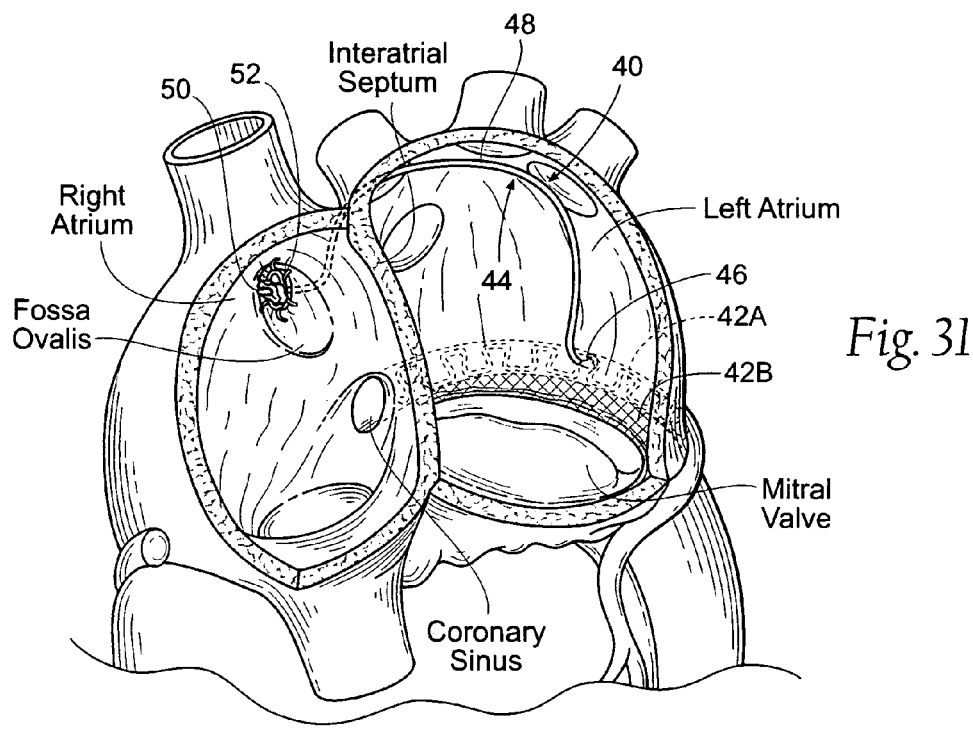
FIG. 31 is an anatomic anterior perspective view of the left and right atriums, with portions broken away and in section to show the presence of an implant system that includes an inter-atrial bridging element that spans the mitral valve annulus, with a posterior region anchored to a tissue consolidating structure in the great cardiac vein, an anterior region anchored high on the interatrial septum, and showing the great cardiac vein conjoined to the left ventricle by bonding means, the inter-atrial bridging element extending in an upwardly curved or domed path generally from a lateral region of the annulus to provide a force vector that includes an upward lifting component and an inward pulling component.

FIG. 31 shows an implant system 40 for treating mitral regurgitation that applies, either alone or in conjunction with horizontal force vectors, a superior or upward lifting force vector(i.e., at a vector greater than about forty-five degrees above the horizontal) upon tissue in the region of the mitral valve annulus. The upward lifting force releases or dissipates tension on the mitral valve annulus from the posterior mitral annulus of the left heart into the implant and brace system of the right heart. It also imposes a more direct vertical force vector component upon atrial tissue between the great cardiac vein and the left ventricle so that the application of horizontal force vectors more directly leads to a desired compressive effect upon the annulus. By applying a vertical force to atrial tissue between the great cardiac vein and the ventricle, less horizontal inward movement of the great cardiac vein is required before a directly compressive effect is applied to the annulus.

Tension on the mitral valve annulus can arise when the left ventricle and annulus become dilated. The magnitude of the tension on the annulus can be significant in situations involving functional mitral regurgitation, particularly functional mitral regurgitation of at least Grade 2+. When the annulus is under tension, the mitral chordae become tense, pulling the coaptation points down and away from each other. Also the annulus-to-leaflet junction becomes taut. An analogy is midline poles (the annulus) holding up a bi-leaf tent (the leaflets), with ropes and stakes (the chordae) holding the tent leaves tautly (the taut leaflets) to the ground (the papillary muscles). If there is insufficient leaflet tissue to coapt in systole, functional mitral regurgitation is the result. This is believed to be the result of the tension that dilation places on the annulus, working in synchrony with the pulling away of the walls of the ventricle.

The implant system 40 imposes a lifting force vector on the annulus (a ventricular structure) by pulling upward on an atrial structure. To achieve this outcome, the system 40 includes a tissue consolidating component 42A, which consolidates the great cardiac vein into a unified physical structure along its length. The system 490 also includes bonding means 42B for conjoining or bonding the great cardiac vein to the ventricle in the region between the great cardiac vein and the ventricle. In this way, as the system 40 pulls upward on a consolidated great cardiac vein (an atrial structure), a lifting force vector is transferred by the conjoined great vein-ventricle tissue region upon the ventricle.

More particularly, the implant system 40 shown in FIG. 31 comprises a tissue-consolidating component 42A. The tissue-consolidating component 42A consolidates the great cardiac vein into a unified physical structure along its length, so that a lifting force applied at one or more points along the length of the great cardiac vein serves to lift the entire great cardiac vein along its length. In the embodiment shown in FIG. 31, the tissue-consolidating component 42A resides, in most part, in the great cardiac vein. It can be sized and configured the same way as the posterior anchor 18 previously described. The tissue-consolidating component 42 can also be introduced and stabilized in the great cardiac vein in the same fashion as already described.

As shown in FIG. 31, the tissue-consolidating component 42A is desirably ring-like, extending from the great cardiac vein to the coronary sinus os adjacent the majority of the length of the posterior mitral annulus within the great cardiac vein. As such, the tissue-consolidating component 42A is located some 5 mm to 20 mm above the ventricular muscle. The tissue consolidating component 42A desirably incorporates radio-opaque features to facilitate fluoroscopic visualization.

The bonding means 42B conjoins or bonds the great cardiac vein to the ventricle in the region between the great cardiac vein and the ventricle. The means 42B bonds non-fibrous, thin atrial tissue at and below the great cardiac vein to the mitral valve annulus. The means 42B in effect bonds the component 42A that consolidates the great cardiac vein to the left ventricular muscle base proximate to the posterior mitral annulus, so that lifting and horizontal forces applied to the component 42 are directly transferred to lifting and/or compression of the annulus itself. The means 42B also diminishes the possibility of a Type 1 left ventricular rupture between the great cardiac vein and the top of the left ventricle as a result of the forces applied to the component 42 over time.

The means 42B for bonding of the great cardiac vein to the ventricle can take various forms. Mechanical means, such as staples can be attached between the component 42A and tissue in the left ventricle. Drugs, and/or irritative agents, and/or heat (e.g., radiofrequency heating), and/or chemical agents can be applied to tissue in the region. Alternatively, or in combination, tissue at or near the great cardiac vein can be subject to fibrosis to reinforce the tissue and elevate the pull-through threshold of the component 42A. Fibrosis can be accomplished by the use of polyester coatings, drugs, irritative agent elutions, or combinations thereof. Fibrosis can also be achieved by the application of heat.

Figure 33A:
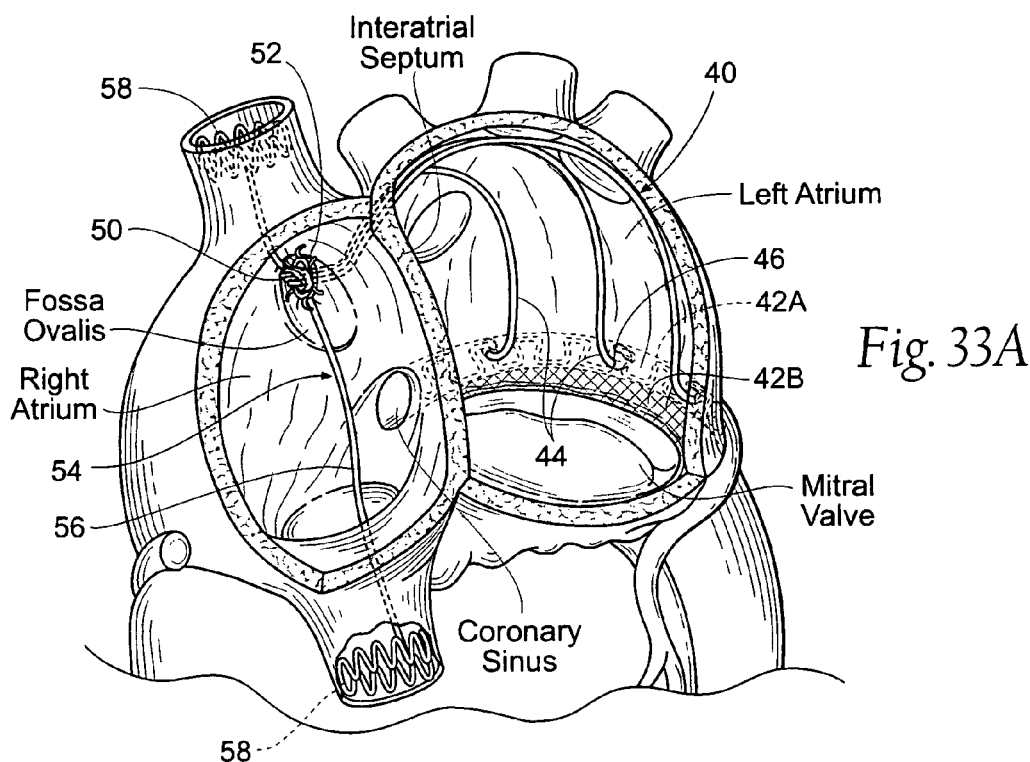
FIG. 33A is an anatomic anterior perspective view of the left and right atriums, with portions broken away and in section to show the presence of an implant system of the type shown in FIG. 32, with the anterior regions of the three implants anchored high on the interatrial septum, as well as in the superior vena cava and the inferior vena cava.
Figure 33B:
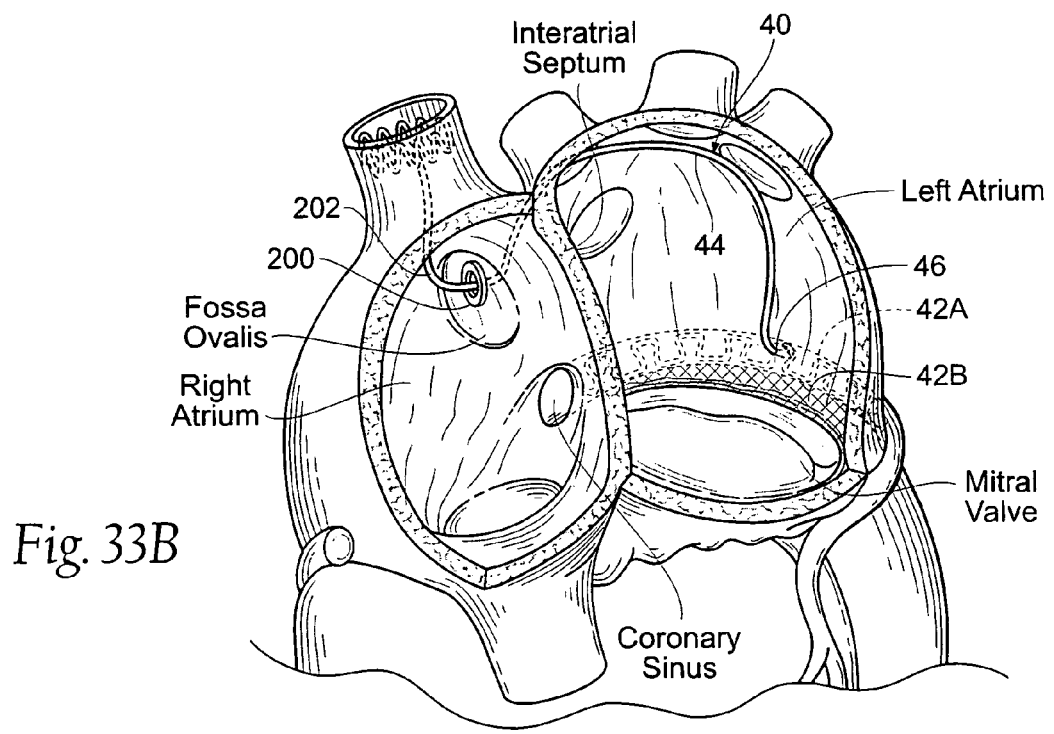
FIG. 33B is an anatomic anterior perspective view of the left and right atriums, with portions broken away and in section to show the presence of an implant system of the type shown in FIG. 31, with the anterior region of the implant extending through pass-through structure in the interatrial septum (without anchoring) for anchoring in the superior vena cava.
Figure 33C:
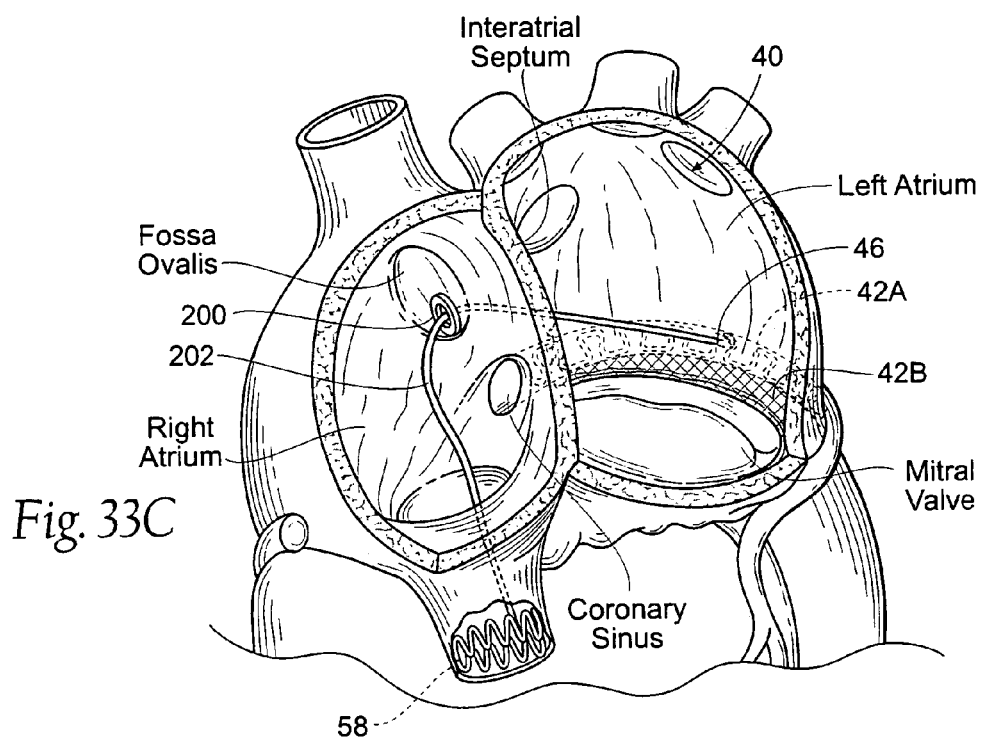
FIG. 33C is an anatomic anterior perspective view of the left and right atriums, with portions broken away and in section to show the presence of an implant system of the type shown in FIG. 31, except that the inter-atrial bridging element is generally straight, with the anterior region of the implant extending through pass-through structure in the interatrial septum (without anchoring) for anchoring in the inferior vena cava.
Figure 33D:
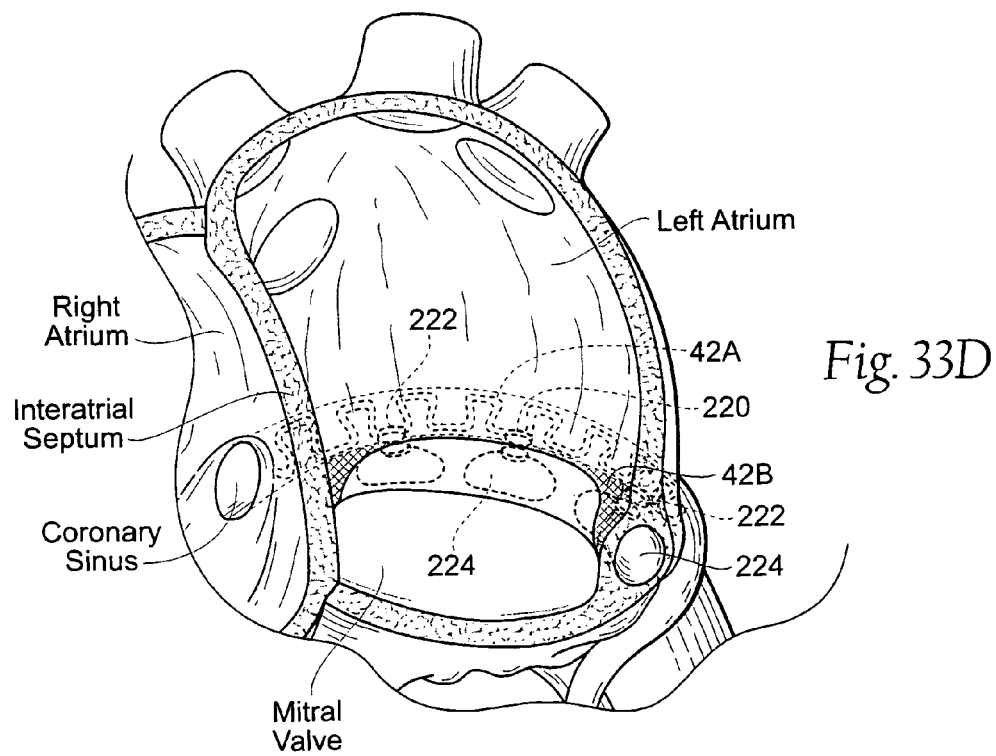
FIG. 33D is an anatomic anterior perspective view of the left atrium, with portions broken away and in section to show the presence of an array of magnetic and/or ferromagnetic elements that conjoin the great cardiac vein to the ventricle.

As shown in FIG. 33D, alternatively, or in combination with the above, the means 42B can comprise an array of magnets 220 carried by the tissue-consolidating component 42A and an array of magnets or soft ferromagnetic elements 222 that are surgically placed beneath the posterior annulus. The polarity of the magnets 220 is selected to magnetically attract the magnetic or soft ferromagnetic elements 222. Of course, if the elements 222 were magnets, soft ferromagnetic materials could be used within the great cardiac vein in lieu of the magnets 220.

In the illustrated embodiment, the elements 222 are carried for implantation by expandable or inflatable bodies 224, e.g., balloons. The bodies 224 can be individually placed by deployment of a catheter through the aortic valve into the left ventricle, into spaced apart locations under the posterior leaflet. Once implanted, the bodies 244 can be expanded or inflated to stabilize the position of the elements 222, e.g., by injection of saline. The magnetically attraction between the magnets 220 and elements 222 draws the two tissue region together, thereby bonding the great cardiac vein to the posterior annulus.

As shown in FIG. 31, the system 40 also comprises one or more lifting components 44. The lifting component 44 has a posterior anchoring region 46 within the left atrium that couples to the tissue-consolidating component 42A residing within the great cardiac vein. Desirably, at least one lifting component 44 has a posterior anchoring region 46 coupled to the tissue-consolidating element 42A superior to and in alignment with the approximate mid-point of the mitral valve annulus, as FIG. 31 shows. As FIG. 32 shows, other lifting elements 44 can be deployed on medial and/or lateral sides of the posterior annulus, at or near one or both trigones.

Figure 32:
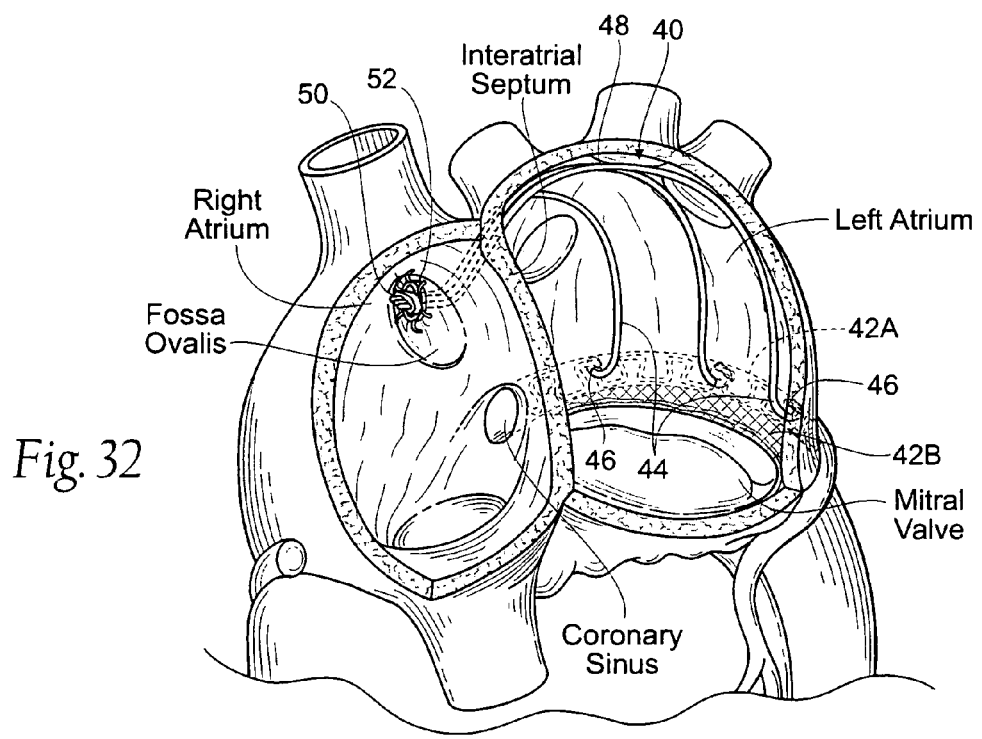
FIG. 32 is an anatomic anterior perspective view of the left and right atriums, with portions broken away and in section to show the presence of an implant system that includes two inter-atrial bridging elements of the type shown in FIG. 31 in association with a tissue consolidating element in the great cardiac vein and bonding means that conjoins the great cardiac vein to the ventricle.

As FIGS. 31 and 32 show, at least one of the lifting components 44 has a spanning region or bridging element 48 that is preformed or otherwise configured to extend high within the left atrium, upward from its anchoring point with the tissue-consolidating component 42A, and toward the dome of the left atrium.

The lifting component 44 also includes an anterior anchoring region 50 that passes out of the left atrium and into the right atrium through fibrous tissue of the high septum. In FIGS. 31 and 32, the anterior anchoring region 50 is shown anchored at or near the superior rim of the fossa ovalis. As will be described in greater detail later (and as is shown in FIGS. 33B and 33C), the anterior region of the lifting component 44 can be anchored to or otherwise tethered within the SVC or IVC, and not anchored to the septum itself. In this arrangement (see FIG. 33B), the lifting component 44 with the high atrial bridging element 48 can pass through the septum high in the fossa ovalis, without anchoring to septal tissue, and be anchored or tethered instead to a stent in the SVC. This arrangement is believed to maximize the effect of the lifting vector. Alternatively (see FIG. 33C), the lifting component 44 (desirably without a high atrial bridging element 48) can pass through the septum low in the fossa ovalis, without anchoring to septal tissue, and be anchored or tethered instead to a stent in the IVC.

The lifting component 44 can be formed by bending, shaping, joining, machining, molding, or extrusion of a metallic or polymer wire form structure, which can have flexible or rigid, or inelastic or elastic mechanical properties. The lifting component 44 can take various shapes and have various cross-sectional geometries. The lifting component can have, e.g., a generally curvilinear (i.e., round or oval) cross-section, or a generally rectilinear cross section (i.e., square or rectangular), or combinations thereof.

Desirably, the lifting component 44 is "elastic." The lifting component 44 is sized and configured to possess a normal, unloaded, shape or condition, in which the component is not in compression or tension. The material of the lifting component 44 is selected to possess a desired spring constant. The spring constant imparts to the component 44 the ability to be elastically stretched and placed in tension in response to external pulling applied at the anterior anchoring region 50 when the posterior anchoring region 46 is coupled to the tissue consolidating component 42A. When in tension, the lifting component 44 applies an upward force (e.g., with a force vector of great than about 45° above horizontal) upon the tissue-consolidating component 42A.

The system 40 further comprises an anchor 52 sized and configured to be coupled to the anterior anchoring region 50 of the lifting component 44 in the right heart. The anchor 52 holds the lifting component 44 in tension against the septum in the right atrium. In an alternative embodiment, stents or equivalent non-obstructing anchors in the IVC or SVC can serve as anchoring sites for the lifting component or components 44.

The lifting component and anchoring component desirably incorporates radio-opaque features to facilitate fluoroscopic visualization.

As FIG. 32 shows, the system 40 may include more than one lifting component 44. Multiple lifting components 44 may be coupled at spaced locations along the consolidating component 42A, for example, three lifting components 44 coupled at or near the mid posterior annulus and the lateral and medial trigones. The anterior anchoring regions 50 of the lifting components 44 may be passed through a single opening at or near the superior rim of the fossa ovalis in the high interatrial septum into the right atrium, and there joined and retained by a single anchor 32.

The arched lifting components 44, which elevate a consolidated great cardiac vein vertically, while bringing it horizontally inward toward the septum, provide mural support to the wall of the left atrial chamber.

The components of the system 40, when assembled in the manner shown in FIGS. 31 to 33, unload tension from the mitral annulus in late diastole and early systole dynamically through dissipation of some of the wall tension that tends to expand the annulus. The great cardiac vein, reinforced and consolidated by the consolidating component 42, becomes the lever upon which the spring-like lifting component 44 or components act to dynamically unload the base of the left ventricle by dissipating ventricular muscle wall tension and relaying it through the now-consolidated AV groove.

As the ventricle starts to fill with blood, the spring-like lifting component 44 or components become maximally loaded at end-diastole and in early systole, when the mitral valve area is the least and functional mitral regurgitation is most likely to occur. The spring energy unloads the ventricular muscular wall tension at end-diastole and early systole, and the annulus is relieved of tension (at least partially) enough to release or dissipate tension from tented mitral leaflets, thereby allowing improved re-approximation of the mitral leaflets especially in late diastole and early systole to allow closure.

The system 40 may also, as a primary or secondary effect, result in re-shaping the annulus.

Figure 34:
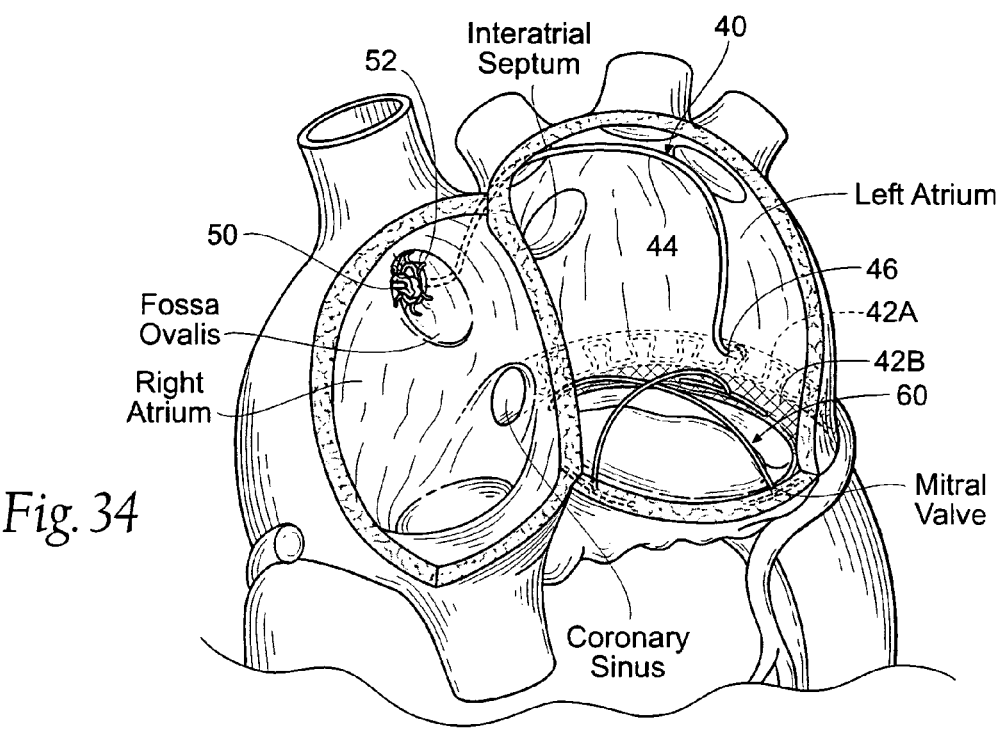
FIG. 34 is an anatomic anterior perspective view of the left and right atriums, with portions broken away and in section to show the presence of an implant system of the type shown in FIG. 31, used in combination with other devices that are implanted adjacent the mitral valve annulus.

As FIG. 34 shows, the system 40 can include auxiliary implant components 60 that extend either across the minor axis of the annulus to shorten the minor axis, or across the major axis of the annulus to shorten or lengthen the major axis, or both minor and major axes can be treated simultaneously. Such implant components 60 can be sized and shaped so that, in use, they apply, in conjunction with the unloading force of the system 40, one or more direct mechanical forces along the minor axis, major axis, or both axes of the annulus, to reshape the annulus. The lifting forces imposed by the system 40 lessen the horizontal leading length of atrial tissue between the great cardiac vein and the ventricle, which must be moved in order to achieve any compressive effect on the posterior annulus imposed by forces applied to an anchor in the great cardiac vein. Thus, the posterior-to-anterior force vectors and/or the medial-to-lateral force vectors imposed by the auxiliary component or components 60 can work in tandem to achieve the desired result. The remodeling effects of the auxiliary component or components 60 can thereby be magnified in the presence of the annulus lifting forces imposed by the system 40.

The auxiliary implant components 60 can be made—e.g., by bending, shaping, joining, machining, molding, or extrusion—from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization. The auxiliary implant components desirable include struts that engage supra-annular tissue.

Further details of implants that can be used as auxiliary implant components 60 are shown in co-pending U.S. patent application Ser. No. 10/677,104, filed Oct. 1, 2003, and entitled "Devices, Systems, and Methods for Reshaping a Heart Valve Annulus," which is incorporated herein by reference.

B. Implantation

The implant systems 40 as just described lend themselves to implantation in a left and right heart in various ways. The systems can be implanted, e.g., in an open heart surgical procedure. Alternatively, the systems can be implanted using catheter-based technology via a peripheral venous access site, such as in the femoral, jugular, subclavian vein or femoral artery, under image guidance. FIGS. 24 to 30 show a representative embodiment of a percutaneous, catheter-based procedure that, under image guidance, can implant the system 40.

Alternatively, the systems 40 can be implanted using thoracoscopic means through the chest, or by means of other surgical access through the right atrium, also under image guidance. Image guidance includes but is not limited to fluoroscopy, ultrasound, magnetic resonance, computed tomography, or combinations thereof.

It is believed that the implant system 40 as described can be sized and configured to allow leaflets to coapt in the face of functional mitral regurgitation above Grade 1+, including up to Grade 4+, which could be ameliorated at least to some significant extent. The system provides rapid deployment, facile endovascular delivery, and full intra-atrial retrievability. The system also provides strong fluoroscopic landmarks.

III. Right Heart Bracing

As FIG. 33A shows, any intra-atrial system with a trans-septal component deployed within the left atrium—e.g., the systems 40 shown in FIGS. 31 to 32 or the implants 10 shown in FIGS. 10 to 19—can also include right heart components 54 that act as braces to stabilize the septal anchor 20 or 52 relative to the tissue-consolidating component 18 or 42. As FIGS. 33B and 33C show, any intra-atrial system with a trans-septal component deployed within the left atrium—e.g., the systems 40 shown in FIGS. 31 to 32 or the implants 10 shown in FIGS. 10 to 19—can also include right heart components 54 placed within or tethered to the SVC or IVC, which anchor the intra-atrial components relative to the tissue consolidating component.

A. Right Atrial Septal Brace

In embodiment shown in FIG. 33A, the right heart component 54 includes a septum brace bar 56 that is coupled to the septal anchor 52. As illustrated, the brace bar 56 desirably extends superiorly and inferiorly along the septum from the anchor 52, to distribute forces uniformly along the septum. A brace bar 56 of the type shown in FIG. 33A can also be coupled in the same fashion to the anchor 20, when used in combination with the implant 10 shown in FIG. 10.

As FIG. 33A also shows, the right heart components 54 may also include stents 58 placed either in the inferior vena cava (IVC), superior vena cava (SVC), or coronary sinus (CS), or the right atrium in general, which are coupled to the brace bar 56. The right heart stents 58 serve as braces to further disperse and absorb forces from the lifting component into the right heart.

B. Vena Caval Anchoring

As FIGS. 33B and 33C show, a given intra-atrial bridging component (e.g., implant 10 in FIG. 10 or component 44 in FIG. 31) can be coupled or tethered directly to anchors or stents 58 deployed in either the SVC or IVC. In this arrangement, the intra-atrial bridging component is not anchored to the septum, but rather can pass through the septum (e.g., at the fossa ovalis) directly to the anchoring stent 58. A washer 200 may be provided on the septum that permits the bridging component to pass through the septum without tearing, but does not anchor the component. Instead, an element 202, e.g., a cable or memory shaped alloy or tether 202, couples the bridging component to the stent 58, which serves to anchor the bridging component.

In the embodiment shown in FIG. 33B, the washer 200 is located high on the fossa ovalis, and the element 202 is coupled to a stent 58 in the SVC. It is believed that this arrangement maximizes the magnitude of the upward lifting (vertical) vector generated by the bridging component BC on the tissue-consolidating component 42 in the great cardiac vein.

In the embodiment shown in FIG. 33C, the washer 200 is located low on the fossa ovalis, and the element 202 is coupled to a stent 58 in the IVC. It is believed that this arrangement maximizes the magnitude of the horizontal vector generated by the bridging component BC on the tissue-consolidating component 42 in the great cardiac vein.

C. Implantation

The right heart components 54 described above lend themselves to implantation in any of the manners previously described.

In a representative catheter-based embodiment, the tissue-consolidating component 42 (which can comprise, e.g., a rigid, malleable, radiopague-marked stent dilated to 10 mm to 25 mm in diameter) can be placed by a catheter into the great cardiac vein, as before described. If the bracing stent 58 is intended to rest in the IVC, a femoral vein into the IVC route can be used. If the bracing stent 58 is intended to rest in the SVC, then a jugular vein into the SVC route is selected.

A guide sheath is then placed through a femoral vein-IVC-fossa ovalis route across the left atrium to the tissue-consolidating component 42. The element 202 is passed through the guide sheath. The element 202 carries at its distal end a grasper (which can be sized, e.g., 7 French). The grasper grasps onto a strut of the tissue consolidating stent 42 and locks that grasp. The element 202 is then drawn across the left atrium, through the fossa ovalis. Tension is applied from within the right atrium to pull the tissue-consolidating stent 42 up and in inside the left atrium. The tension is set to moderate or eliminate the functional MR as much as possible.

The caval stent 58 (e.g., measuring 5 cm to 10 cm long, and 3 cm to 7 cm diameter) is threaded over the element 202 into the vena cava where catheter access for the element 202 was achieved. In the IVC, for example, the stent 58 gets placed just above the liver and just below the right atrium. A lock device is threaded over the element 202 from its proximal end up to the caval stent 58. The element 202 is then cut below the lock nut and the element 202 below the nut is removed. The stent 58 serves to hold and lock the element 202 in its vertical position.

It is believed that providing the option of using either the atrial septum, and/or the IVC, and/or the SVC as potential anchoring sites in the manners just described, makes it possible to flexibly adapt a given implant system to the local anatomy encountered, as well as to optimally guide and distribute the direction and magnitude of the force vectors sought to be applied by the intra-atrial bridging component or components.

III. Circumferential Implant Systems

A. Circumferential Loop

1. Structure

Figure 35:
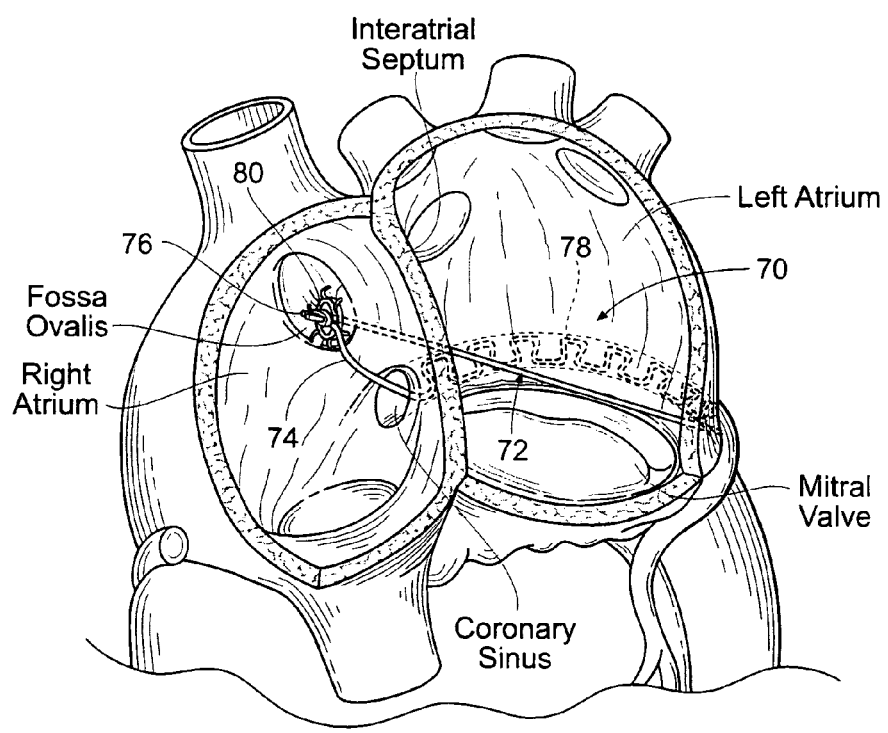
FIG. 35 is an anatomic anterior perspective view of the left and right atriums, with portions broken away and in section to show the presence of an implant system that forms a circumferential loop that applies force vectors to tissue in the region of the posterior mitral valve annulus.

FIG. 35 shows a loop implant system 70 for treating mitral regurgitation that applies, either alone or in conjunction with other force vectors, a circumferential force vector upon tissue in the region of the posterior mitral valve annulus. The inward radial force vector compresses the posterior annulus with a sphincter-like effect, as well as toward to septum, reducing dilation.

As shown in FIG. 35, the system 70 includes an elongated implant 72 having first and second anchoring regions 74 and 76, and an intermediate region 78 extending between them. In total length, the implant 72 is sized and configured to be deployed as a loop, which (i) extends from the first anchoring region 74 on the interatrial septum in the right atrium or in a vena cava, (ii) passes within the right atrium through the coronary sinus and, from there, the intermediate region 78 resides within the great cardiac vein parallel and superior to the posterior mitral annulus, (iii) exits the great cardiac vein through a sidewall of a stent or midrange of a T-shaped tubular device, an end of a stent or tubular anchor device located inside the great coronary vein, and then through the adjacent inner wall of atrial tissue at or near the region of the lateral trigone, (iv) from there, extends in a posterior-to-anterior direction across the left atrium, through the interatrial septum into the right atrium, and (v) allows the second anchoring region 76 to be anchored in the right atrium or in a vena cava coincident with or near the first anchoring region 74. One or more anchors 80 hold the loop implant 72 in tension.

As shown in FIG. 35, the anchoring site for the anchor 80 is shown to be superior to the plane of the anterior mitral valve annulus. More particularly, the anchoring site for the anchor 80 is within the fossa ovalis. This is because the fossa ovalis presents a fibrous tissue region that can be accessed and fastened to with relative technical ease, given conventional interventional radiological and surgical skills and techniques. It should be appreciated other more inferior or more superior sites can be used as trans-septal points of passage to optimize bridging element vectors in the septum, taking into account the same technical and surgical considerations.

The loop implant 70 serves to apply a direct mechanical force that pulls radially inward upon the posterior annulus. The direct mechanical force can serve to shorten the minor axis of the annulus. In doing so, the implant 70 can also reactively reshape the annulus along its major axis and/or reactively reshape other surrounding anatomic structures. It should be appreciated, however, the presence of the implant 70 can serve to stabilize tissue adjacent the heart valve annulus, especially at different and important times in the cardiac cycle when valve coaptation should be improved (e.g., late diastole and early systole), without affecting the length of the minor or major axes. The mechanical force applied by the implant 70 to the tissues attached to the annulus can restore to the heart valve annulus and leaflets a more normal anatomic shape and tension, conducive to coaptation of the leaflets during ventricular systole. The implant 70 can thus reduce the incidence of mitral regurgitation.

Due to the superior location of the anchor 80 in the septum in the illustrated embodiment, the mechanical force of the loop implant 70 also pulls upward (i.e., with a vertical force vector) on the posterior annulus. This vertical vector is further enhanced when anchorage originates in the superior vena cava and a more vertical pull is exerted on the bridging element or bridge from this vantage than can be from a septal anchor. This vertical force vector can also serve to unload tension on the annulus, as well as to lessen the horizontal leading length of atrial tissue between the GCV and the ventricle, which must be moved by an anchor in the GCV in order to achieve any compressive effect on the posterior annulus, with the beneficial effects previously described. In situations where the SVC orifice is high enough, the magnitude of the vertical vector can be enhanced if the right side bridging element is anchored to a stent in the SVC in the manner shown in FIG. 33B, instead of to the septal wall itself. The loop implant 70 can also be anchored to a stent in the IVC in the manner shown in FIG. 33C, where in select situations the inverse may apply to the case of the SVC application.

In its most basic form, the implant 70 is made from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization.

As shown in the illustrated embodiment, the portion of the intermediate region 78 that resides within the great cardiac vein can comprise a stent-like structure that is sized and configured to be introduced into the great cardiac vein through the coronary sinus os in the right atrium. In this form, the intermediate region 78 can comprise an expandable scaffold, which can take the form of a self-expanding stent, or a malleable structure that is expanded by means of an interior force, e.g., a balloon. The intermediate region 78 may be held in position within the vein by gripping the surrounding vessel wall, e.g., by barbs, tines, or the like. If desired, the intermediate region 78 may be further secured by suture, adhesive, or like material within the vein. The intermediate region 78 can incorporate roughened or porous surfaces and/or other materials (e.g., polyester fabric) to promote tissue in-growth.

The anchoring regions 74 and 76 can comprise wire-form structures formed by bending, shaping, joining, machining, molding, or extrusion of a metallic or polymer wire form structure to the intermediate region 78. Desirably, the material of the implant 70 is selected to impart elastic mechanical properties.

2. Implantation

The loop implant 70, like the implant or implant systems already described, lends itself to implantation in a heart valve annulus in a beating heart or an open heart surgical procedure, or by catheter-based technology via a peripheral venous access site under image guidance, or by closed chest thoracoscopic means through the chest, or by means of other open chest surgical access through the right atrium under image guidance.

Figure 36:
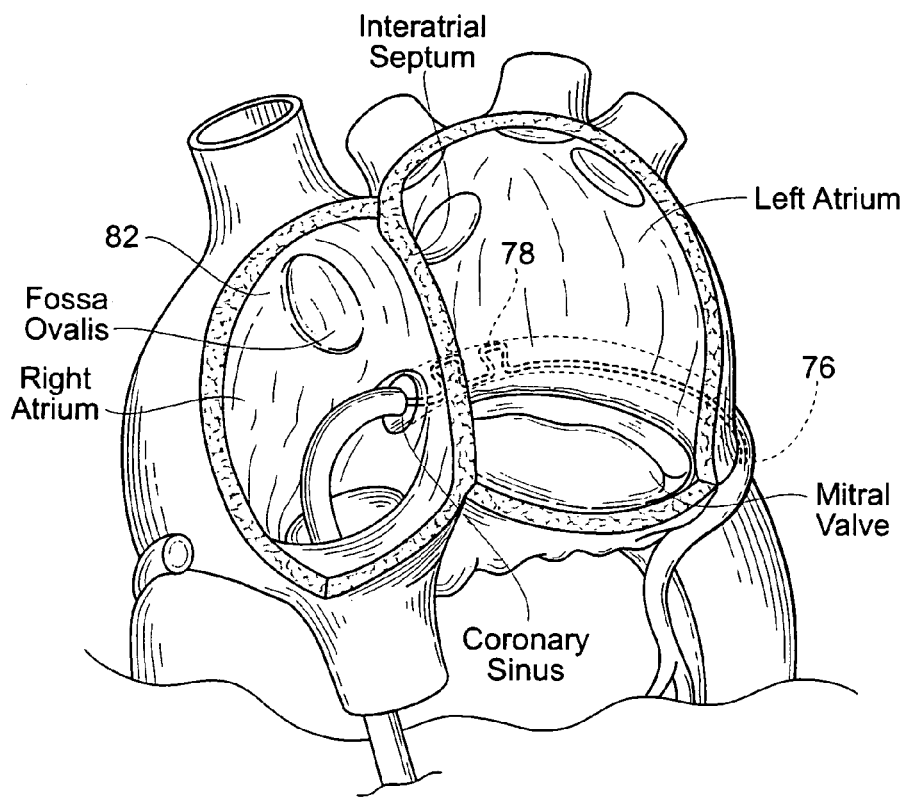
FIGS. 36 to 39 are anatomic views depicting representative catheter-based devices and steps for implanting an implant system of the type shown in FIG. 35.

For example, if a percutaneous, catheter-based procedure is used under image guidance, percutaneous vascular access can be achieved by conventional methods into the femoral or jugular or subclavian vein to deploy a first catheter 82 into the right atrium. As shown in FIG. 36, the first catheter 82 advances the implant 70, anchoring region 76 first, through the coronary sinus os in the right atrium and into the great cardiac vein. The anchoring region 76 and intermediate region 78 are advanced into the great cardiac vein, such that the anchoring region 76 is located at or near the lateral trigone. FIG. 36 shows access through the femoral-IVC route for purposes of illustration.

Figure 37:
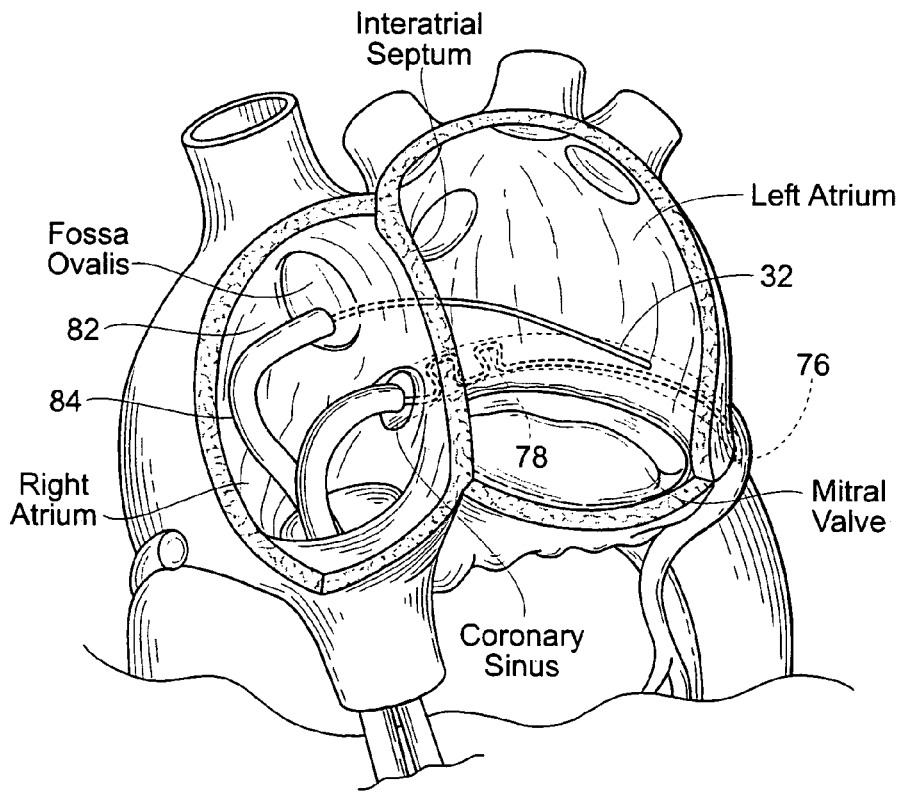

As FIG. 37 shows, a second catheter 84 is steered through the vasculature (also via the IVC) into the right atrium. The second catheter 84 carries a distal needle (not shown), which is deployed to pierce the septum between the right and left atrium (e.g., at the fossa ovalis). Once access between the right and left atriums is opened, a guide wire 32 is advanced trans-septally through the needle catheter 84 into the left atrium.

Figure 38:
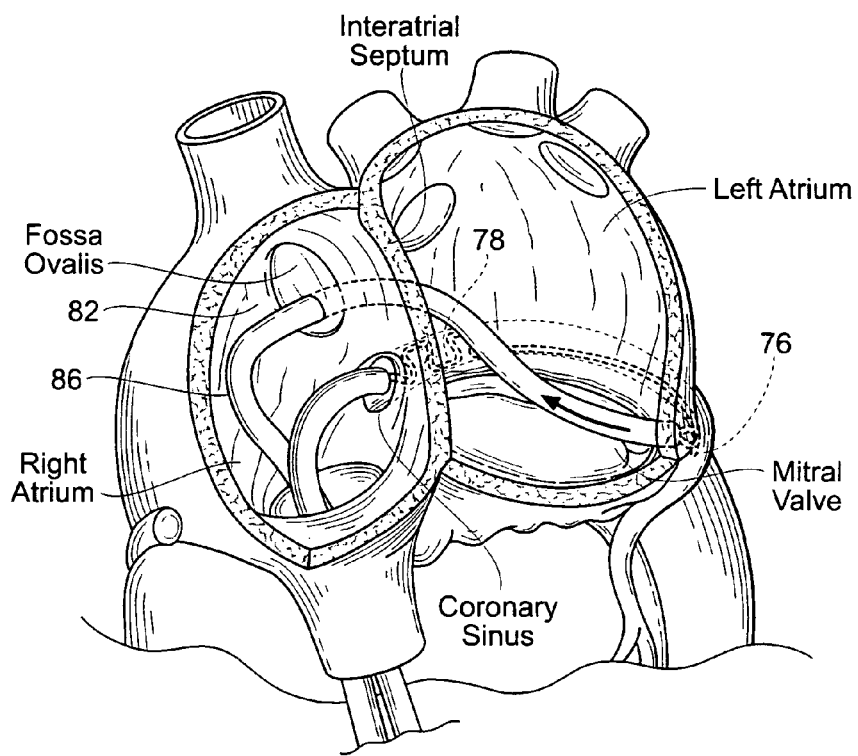
Figure 39:
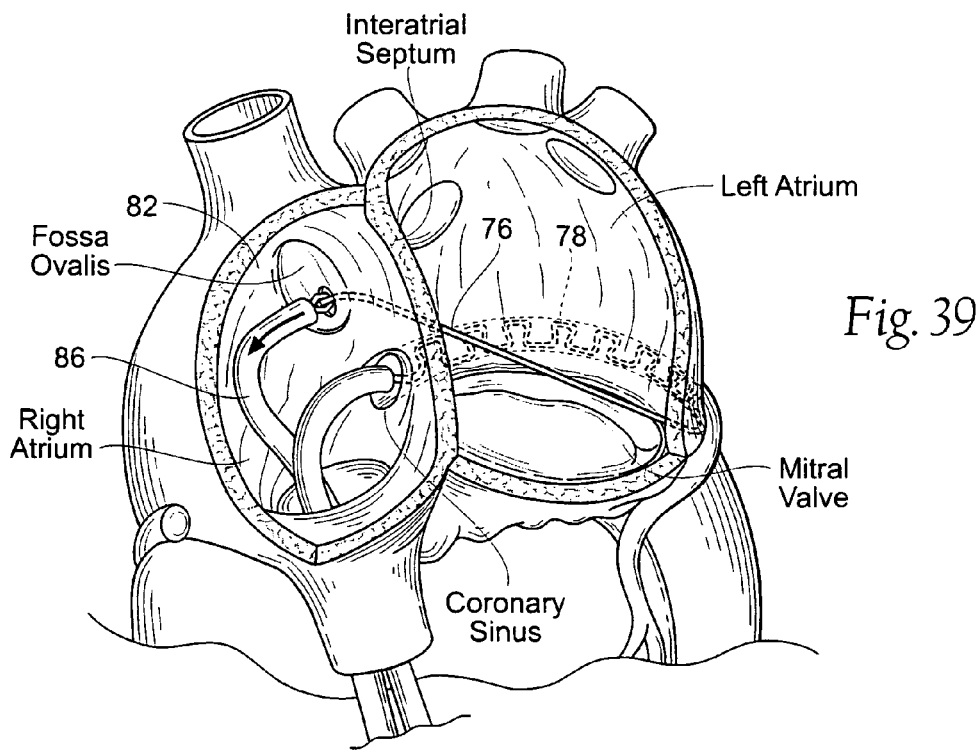

The second catheter 84 is withdrawn (see FIG. 38), and, under image guidance, a third catheter 86 is advanced over the guide wire 32 trans-septally through the fossa ovalis puncture, and into the left atrium. Under image guidance, the third catheter 86 is directed to the site where the anchoring region 76 resides within the great cardiac vein. As before described, the catheter 86 can include an on-board distal steering mechanism or a magnetic tracking system to locate the targeted site. The third catheter 86 is manipulated to puncture atrial tissue at the targeted site, grip the anchoring region 76, and attach a bridging anchoring element 76 to or draw the anchoring region 76 out of the great cardiac vein and anteriorly across the left atrium (as FIG. 38 shows). The remaining portion of the intermediate region 78 is deployed from the first catheter 82 into the great cardiac vein, as the third catheter 86 leads the anchoring region 76 back through the septum and into the right atrium (as FIG. 39 shows).

The first catheter 82 and the third catheter 86 are manipulated within the right atrium to pull tension on the implant 70, until a lessening or elimination of the incidence of mitral regurgitation is confirmed by monitoring. Once the desired therapeutic result is achieved, the anchor 80 is applied to both anchoring regions 74 and 76, e.g., by one of the catheters 82 or 86 or by a separate intravascular crimping tool or a lock that is advanced from the outside over the wire to engage the brace. This retains the loop implant 70 in the desired degree of tension. The anchoring region 74 is cut next to anchor 80, ending the installation, and the intravascular tool or tools are withdrawn, leaving the implant 70 in the condition shown in FIG. 35.

B. Loop Systems

In an alternative embodiment (see FIG. 40), a loop implant system 90 includes a preformed shaped, cannulated structure 92 that is sized and configured to reside within the great cardiac vein. The structure 92 includes an interior lumen 94. The structure 92 is preformed to impart a shape-altering force upon tissue in the region of the great cardiac vein to counteract dilation of the annulus. The structure 92 can comprise an expandable stent-like structure or a preformed tubular structure.

The implant system 90 also includes a tension element 96. The tension element 96 has anchoring end regions 98 and 100 and an intermediate region 102. The tension element 96 can comprise a wire-form structure formed by bending, shaping, joining, machining, molding, or extrusion of a metallic or polymer wire form structure. Desirably, the material of the element 96 is selected to impart elastic mechanical properties.

Figure 40:
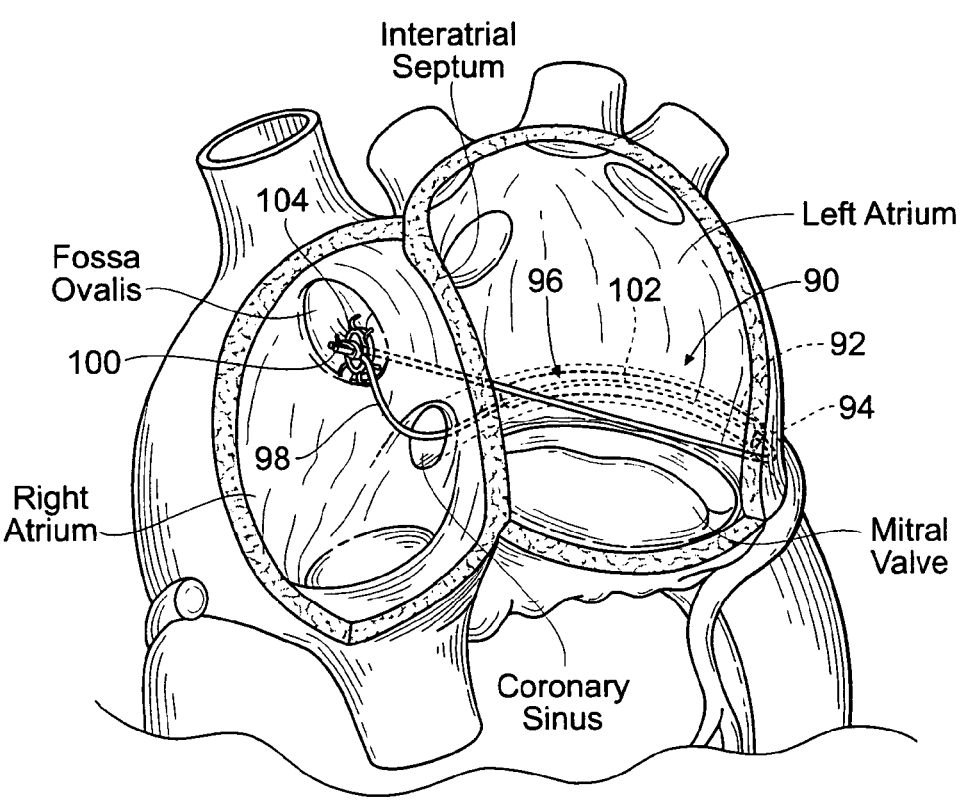
FIG. 40 is an anatomic anterior perspective view of the left and right atriums, with portions broken away and in section to show the presence of an alternative embodiment of an implant system that forms a circumferential loop that applies force vectors to tissue in the region of the posterior mitral valve annulus.

In use, as FIG. 40 shows, the end regions 98 and 100 are anchored to the interatrial septum by one or more anchors 104. In the illustrated embodiment, anchors 104 are affixed to the septum in the right and left heart.

Held in tension by the anchors 100, the intermediate region 102 of the element 96 extends within the right atrium from the end region 98, into the great cardiac vein through the coronary sinus, passes through the lumen 94 of the shaped structure 92 within the great cardiac vein, exits the great cardiac vein at or near the lateral trigone (or at any point thought to best achieve a maximal effect on the annulus to ameliorate functional mitral regurgitation—i.e., at or near the mid point of the posterior mitral annulus), and, from there, spans in a posterior-to-anterior path across the left atrium to the anchoring element 100.

Like the loop implant 70 shown in FIG. 35, the loop implant system 90 shown in FIG. 40 serves to apply a direct mechanical force that pulls radially inward upon the posterior annulus. The memory of the preshaped structure 92 amplifies the inward radial vector of the direct mechanical force adjacent the posterior annulus. As explained in connection with the implant 70, the force exerted by the implant system 90 can serve to restore the heart valve annulus and leaflets a more normal anatomic shape and tension, conducive to coaptation of the leaflets during ventricular systole.

As previously explained in connection with the implant 70, the anchors 104 can be placed relatively high in the septum (e.g., at the fossa ovalis) to apply a mechanical force that also pulls upward (i.e., with a vertical force vector) on the posterior annulus. This vertical force vector can also serve to unload tension on the annulus, as well as to lessen the horizontal leading length of atrial tissue between the great cardiac vein and the ventricle, which must be moved by an anchor in the great cardiac vein into order to achieve a compressive effect on the posterior annulus. Alternatively, the implant can be anchored directly either to the SVC (in the manner shown in FIG. 33B) or to the IVC (in the manner shown in FIG. 33C).

Similar tools and techniques as previously described can be used to implant the system 90 shown in FIG. 40 using percutaneous, catheter-based procedures.

IV. Right Heart Implant Systems

A. Elastic Right Heart Implant

Figure 41:
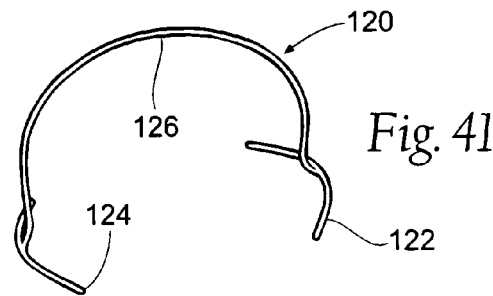
FIG. 41 is a perspective view of an elastic right heart implant that can, when implanted in the right atrium, affect the shape and/or function of a mitral valve annulus in the left atrium.
Figure 42:
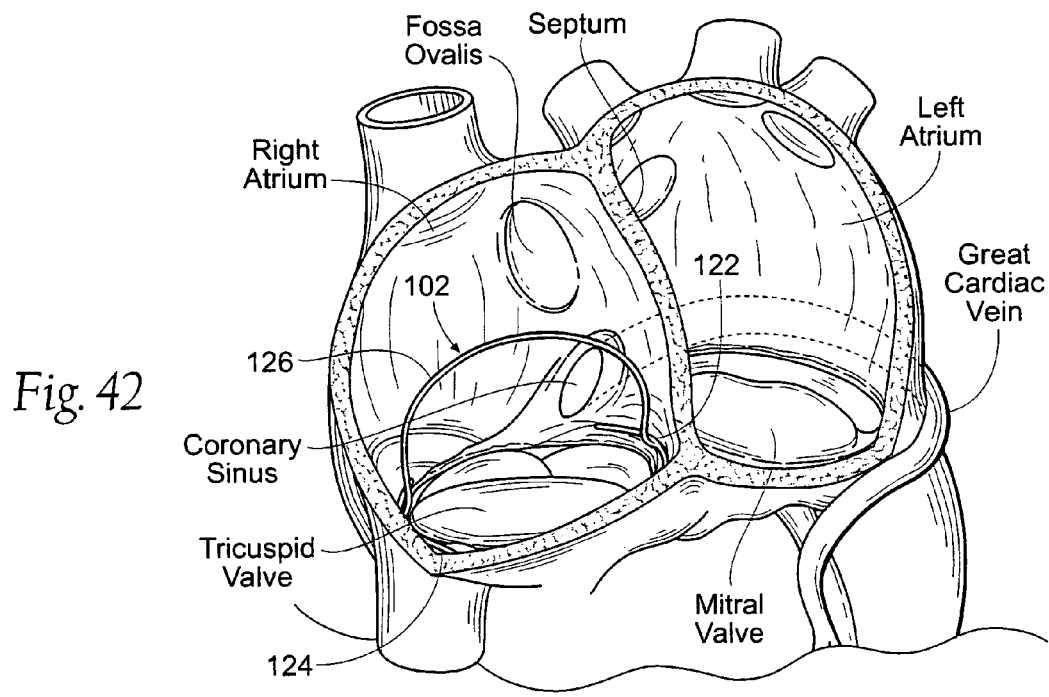
FIG. 42 is an anatomic anterior perspective view of the left and right atriums, with portions broken away and in section to show the presence of the right heart implant shown in FIG. 41.
Figure 43:
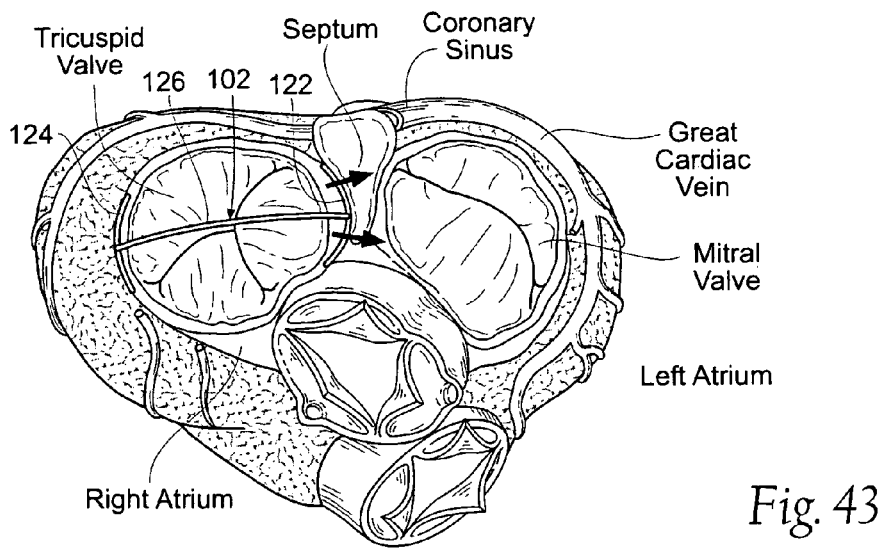
FIG. 43 is an anatomic superior perspective view of the left and right atriums, with portions broken away and in section to show the presence of the right heart implant shown in FIG. 41.

FIG. 41 shows an elastic right heart implant 120 sized and configured to rest in compression in the right atrium (see FIG. 42) to affect the shape and/or function of a mitral valve annulus in the left atrium (see FIG. 43).

In terms of structure, the right heart implant 120 can be of the type described in copending U.S. patent application Ser. No. 10/677,104, filed Oct. 1, 2003, and entitled "Devices, Systems, and Methods for Reshaping a Heart Valve Annulus," which is incorporated herein by reference—except that, in use, the implant 120 is intended, in use, to be implanted in the right heart and not the left heart, as disclosed in the referenced application.

As described in the above-identified application, the implant 120 is desirably made—e.g., by bending, shaping, joining, machining, molding, or extrusion—from a biocompatible, super-elastic metallic material. As shown in FIG. 41, the right heart implant 120 includes a pair of struts 122 and 124 joined by an intermediate rail 126.

As FIGS. 42 and 43 show, the strut 122 is sized and configured to rest in tissue in, at, or near the septum in the right atrium at a location that is generally in opposition to a portion of the anterior annulus of the mitral valve in the left atrium (with the aorta in between). The other strut 124 is sized and configured to rest in tissue in, at, or near a right atrial wall which generally faces the location of the septal strut 122.

The superelastic material of the right heart implant 120 is selected to possess a desired spring constant. The spring constant imparts to the rail 126 the ability to be elastically compressed into an elastically loaded condition, when resting in engagement with tissue as just described. When in its elastically loaded, compressed condition, the rail 126 exerts opposing forces to the tissues through the struts 122 and 124.

The struts 122 and 124 can engage tissue in a stable fashion in various ways. The struts 122 and 124 can rely upon compressive forces imparted by the mechanical, superelastic properties of the rail 126 to retain a stable position engaged in tissue. The struts 122 and 124 can, alternatively or in combination with compressive forces, include barbs or other fixation devices that penetrate or otherwise take purchase in tissue. Other types of tissue engaging mechanisms can be used, e.g., roughened surfaces or tissue in-growth promoting materials. Any fixation mechanism may, if desired, be combined with suture, an adhesive, or like material to further secure the right heart implant 120.

The compression force applied by the septal strut 122 applies a force on the septum in the direction of the left atrium (a shown by arrows in FIG. 43). The trans-septal force applied by the implant 120 may tend to displace tissue adjacent the anterior annulus of the mitral valve inwardly toward the posterior annulus (see FIG. 43). The trans-septal tissue displacement adjacent the anterior annulus may serve to shorten the minor axis of the mitral valve annulus (see FIG. 43). In doing so, the right heart implant 120 may also reactively reshape the mitral valve annulus along its major axis and/or reactively reshape other surrounding anatomic structures in the left heart. It should be appreciated, however, the presence of the right heart implant 120 may serve to stabilize tissue adjacent the mitral valve annulus, without affecting the length of its minor or major axes. The mechanical force applied by the right heart implant 120 across the septum may restore to the mitral valve annulus and leaflets a more normal anatomic shape and tension. The more normal anatomic shape and tension are conducive to coaptation of the leaflets during ventricular systole, which, in turn, reduces mitral regurgitation.

The right heart implant 120 can be elastically straightened and/or folded to fit within a catheter or sheath for deployment in a catheter-based procedure within the right atrium. Alternatively, the right heart implant 120 can be deployed during an open surgical or thoracoscopic procedure.

B. Plastically Deformable Right Heart Implant

Figure 44A:
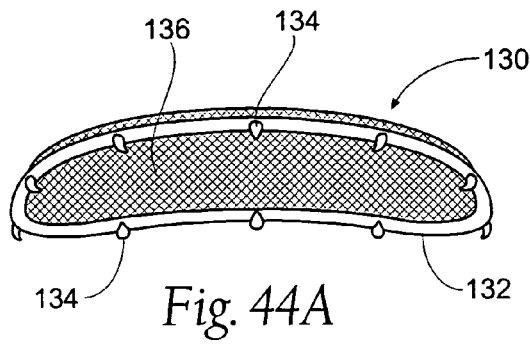
FIGS. 44A and 44B are, respectively, a top and side view of a plastically deformable right heart implant that can, when implanted in the right atrium, affect the shape and/or function of a mitral valve annulus in the left atrium.
Figure 44B:
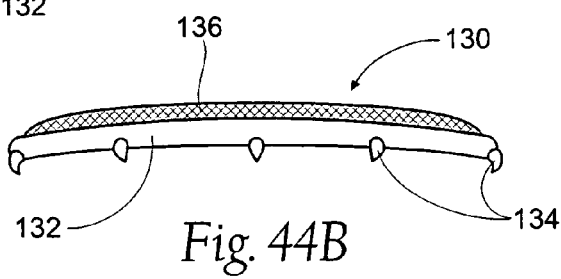
Figure 48:
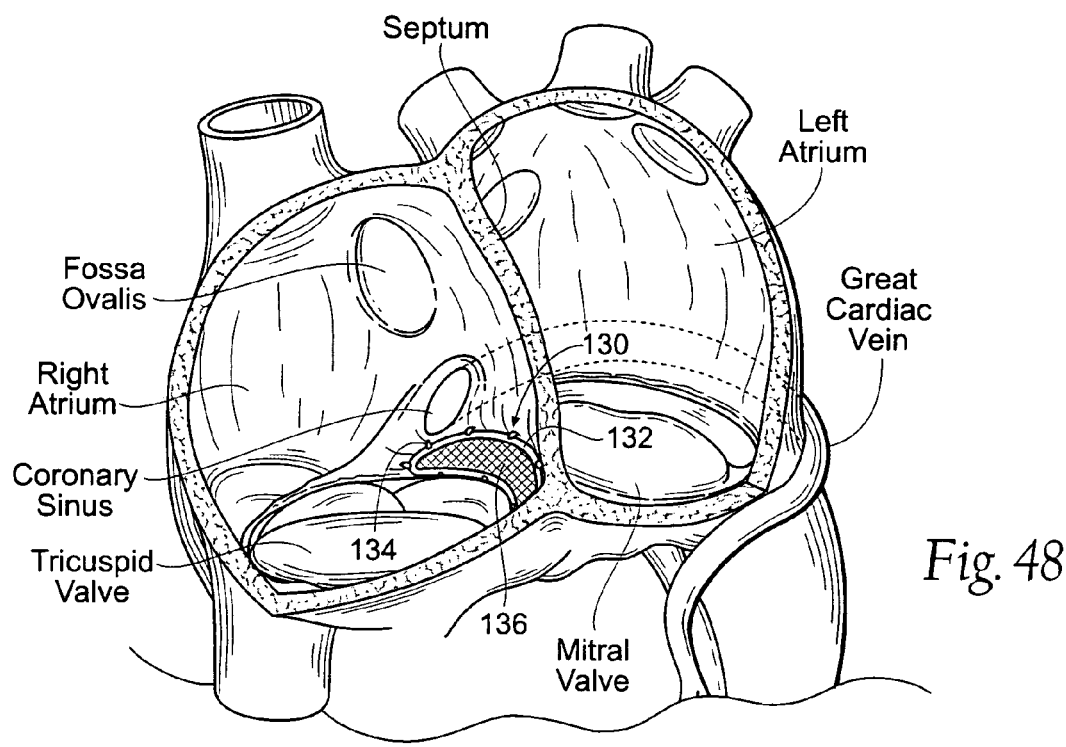
FIG. 48 is an anatomic anterior perspective view of the left and right atriums, with portions broken away and in section to show the presence of the right heart implant shown in FIGS. 44A and 44B, after being plastically deformed.
Figure 49:
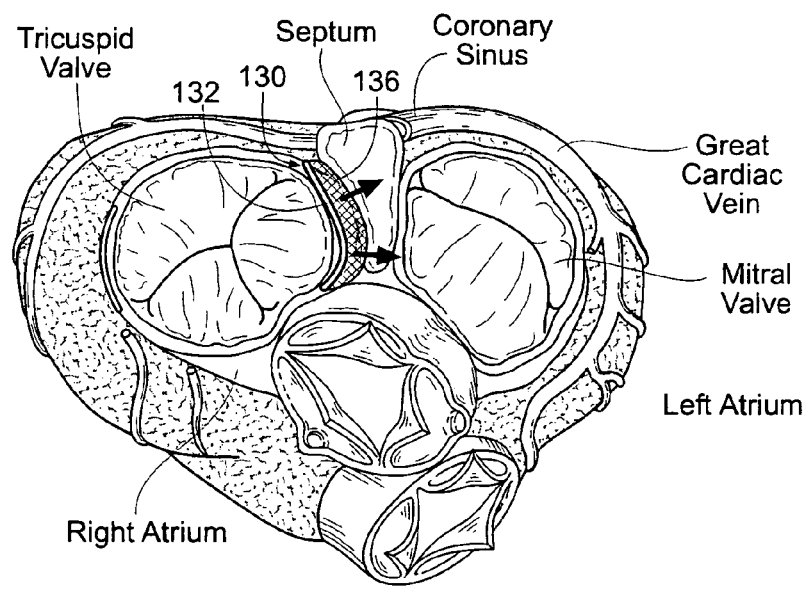
FIG. 49 is an anatomic superior perspective view of the left and right atriums, with portions broken away and in section to show the presence of the right heart implant shown in FIGS. 44A and 44B, after being plastically deformed.

FIGS. 44A and 44B show a representative embodiment of a plastically deformable implant 130 sized and configured to rest in an expanded condition in compression against the septum in the right atrium (see FIG. 48) to affect the shape and/or function of a mitral valve annulus in the left atrium (see FIG. 49).

As shown in FIGS. 44A and 44B, the implant 130 includes a frame 132, which is shown to be generally oval or elliptical in configuration. Other linear or curvilinear configurations can be used. The frame may be made, e.g., by bending, shaping, joining, machining, molding, or extrusion a biocompatible, metallic or polymeric material.

The frame 132 is sized and configured to rest in tissue in, at, or near the septum in the right atrium at a location that is generally in opposition to a portion of the anterior annulus of the mitral valve in the left atrium.

The implant 130 also includes an array of tissue fixation elements 134, which are attached to the periphery of the frame 132. In the illustrated embodiment, the fixation elements 134 comprise barbs that penetrate tissue, to secure the frame 132 to the targeted tissue region. Other types of tissue engaging mechanisms can be used, e.g., roughened surfaces or tissue in-growth promoting materials. Any fixation mechanism may, if desired, be combined with suture, an adhesive, or like material to further secure the frame 132 of the right heart implant 130.

Figure 45:
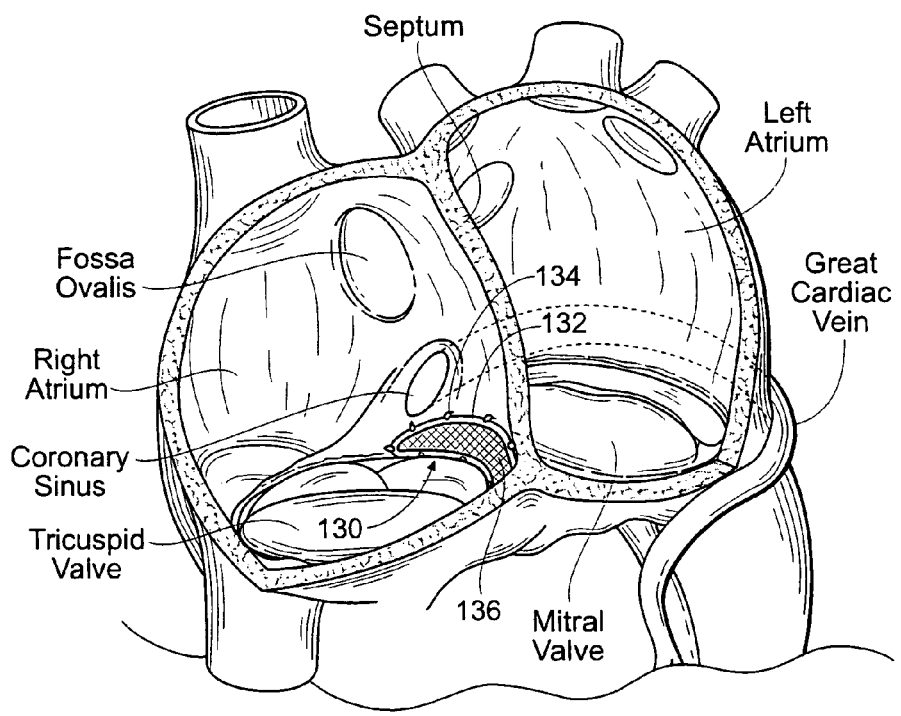
FIG. 45 is an anatomic anterior perspective view of the left and right atriums, with portions broken away and in section to show the presence of the right heart implant shown in FIGS. 44A and 44B, prior to being plastically deformed.
Figure 46:
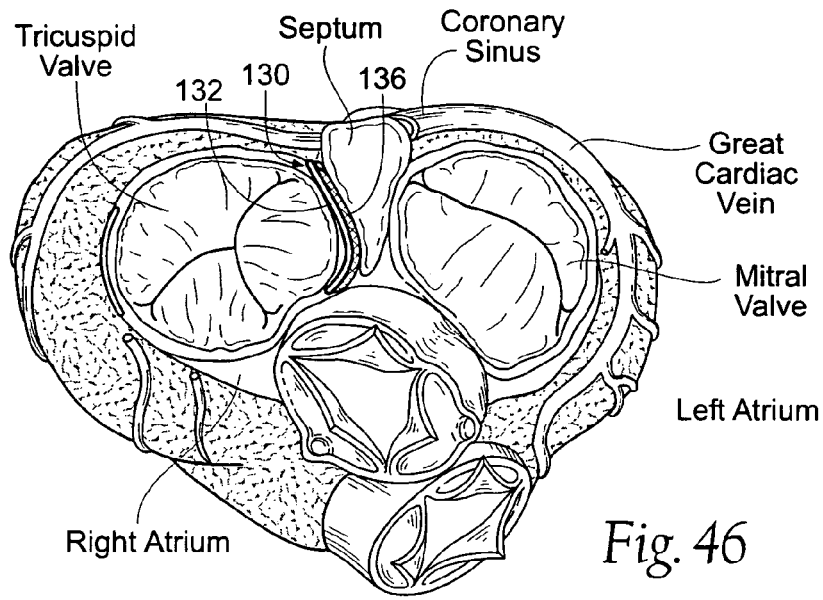
FIG. 46 is an anatomic superior perspective view of the left and right atriums, with portions broken away and in section to show the presence of the right heart implant shown in FIGS. 44A and 44B, prior to being plastically deformed.

A plastically deformable structure 136 is mounted to the interior of the frame 132. In the illustrated embodiment, the structure 136 takes the form of a woven or mesh-like web, which can be made of a metallic or polymeric material. The structure 136 is attached to the frame 130 in a normally unstretched condition. In is in this condition that the implant 130 is affixed to the targeted tissue region on the septum (see FIGS. 45 and 46). The right heart implant 130 can be elastically straightened and/or folded to fit within a catheter or sheath for deployment in a catheter-based procedure within the right atrium. Alternatively, the right heart implant 130 can be deployed during an open surgical or thoracoscopic procedure.

Figure 47:
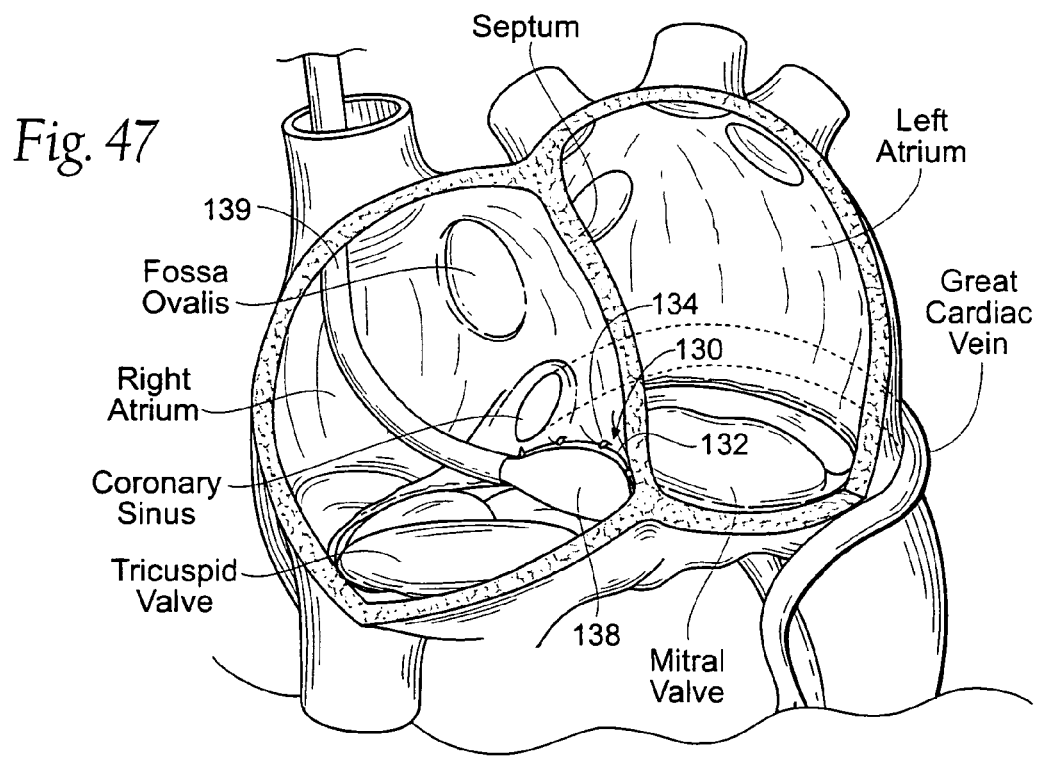
FIG. 47 is an anatomic anterior perspective view of the left and right atriums, with portions broken away and in section to show a catheter-based tool that plastically deforms the implant shown in FIGS. 44A and 44B.

The plastically deformable nature of the structure 136 makes possible its expansion and shaping in situ against the septum within the right atrium. As FIG. 47 shows, an inflatable body 138 (e.g., balloon) can be used to expand and shape the structure 136, as can a suitable mechanical device (e.g., a scissor-jack). The body 138 can be carried by a catheter 139 for deployment in a catheter-based procedure within the right atrium. Alternatively, the body 138 can be deployed during an open surgical or thoracoscopic procedure.

During expansion and shaping, the structure 136 is stretched into an outwardly bowed or concave configuration within the frame 130. The stretched structure 132 projects against the septum (see FIGS. 48 and 49), applying a compression force across the septum. The compression force applied by the plastically deformed structure 136 is translated from the right heart side of the septum, across the septum, and to the anterior annulus of the mitral valve on the left heart side of the septum, where it may tend to displace tissue adjacent the anterior annulus of the mitral valve inwardly toward the posterior annulus (see FIGS. 48 and 49). As before explained, the trans-septal tissue displacement adjacent the anterior annulus may serve to shorten the minor axis of the mitral valve annulus (see FIG. 49). In doing so, the right heart implant 130 may also reactively reshape the mitral valve annulus along its major axis and/or reactively reshape other surrounding anatomic structures in the left heart. It should be appreciated, however, the presence of the right heart implant 130 may serve to stabilize tissue adjacent the mitral valve annulus, without affecting the length of its minor or major axes. The mechanical force applied by the right heart implant 130 across the septum may restore to the mitral valve annulus and leaflets a more normal anatomic shape and tension. The more normal anatomic shape and tension are conducive to coaptation of the leaflets during ventricular systole, which, in turn, reduces mitral regurgitation.

The plastically deformable implant 130 shown in FIGS. 44A and 44B may also be used in association with a a loop implant system 90 shown in FIG. 40. In this arrangement, the loop implant system 90 would include a linking member coupling the anchor 100 in the fossa ovalis to the plastically deformable implant 130 deployed in the right atrium in the position shown in FIG. 45. The plastically deformable implant 130 and linking member would serve as a stabilizing element for the anchor 100 and thus for the entire the loop implant system 90.

C. Right Heart Anchored Great Cardiac Vein Implant

Figure 50:
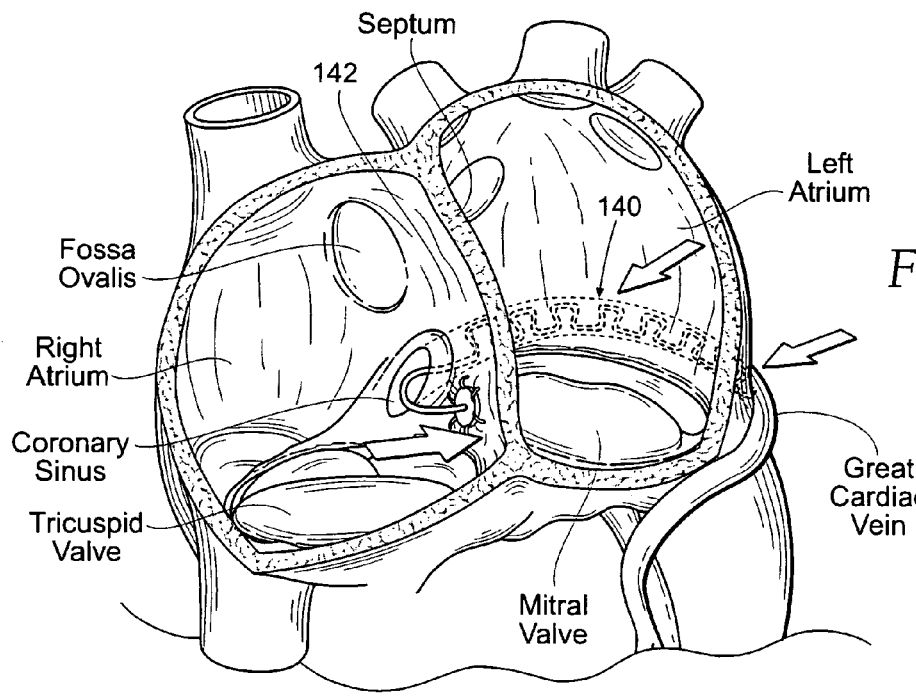
FIG. 50 is an anatomic anterior perspective view of the left and right atriums, with portions broken away and in section to show the presence of an implant deployed in the great cardiac vein and anchored to the septum in the right atrium.

In preceding embodiments (see, e.g., FIG. 10 or FIG. 31), various implants 18 and 42 have been placed within the great cardiac vein, to serve as an attachment point for other intra-atrial components, which are placed in tension in the left atrium. As FIG. 50 shows, a given implant 140 can be placed into tension within the great cardiac vein, and the tension can be retained by an anchor 142 affixed to the septum within the right atrium. The tension tends to pull a radially shaped and rigid anchor 140 along with the posterior annulus in a radially inward direction. The great cardiac vein implant 140, placed into tension and anchored in the right atrium, can be used alone, or in combination with other components deployed within the left atrium. The implant 140 can comprise a stent-like structure (as shown) or a pre-formed rod (e.g., c-shaped) placed in the great coronary vein.

Figure 51:
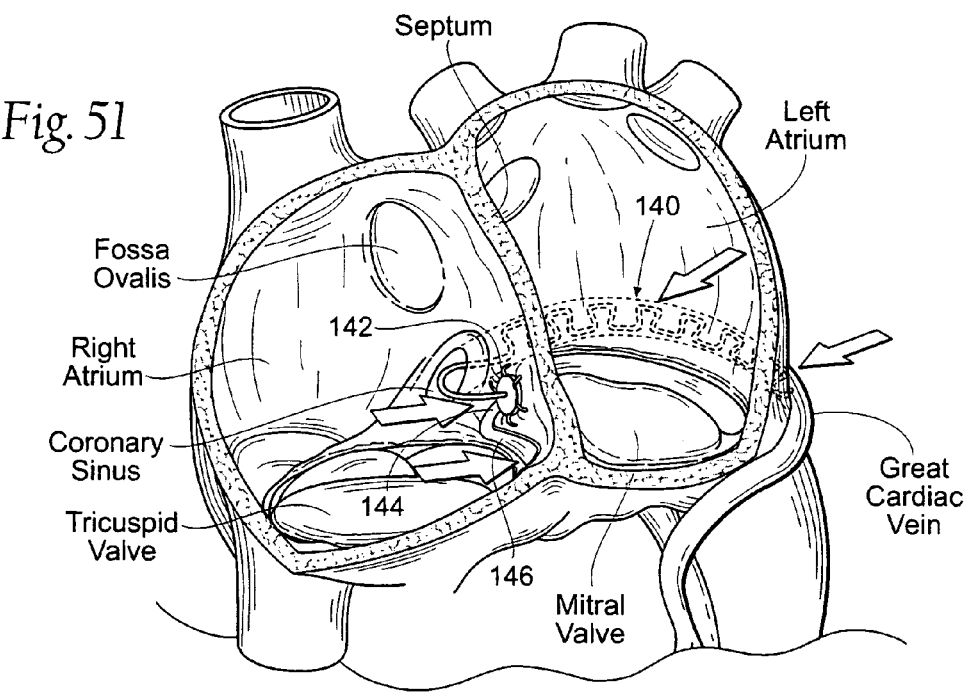
FIG. 51 is an anatomic anterior perspective view of the left and right atriums, with portions broken away and in section to show the presence of the implant shown in FIG. 50, with an appendage that compresses tissue in, at or near the septum in opposition to a portion of the anterior mitral valve annulus in the left atrium.

As FIG. 51 shows, the great cardiac vein implant 140, placed into tension and anchored in the right atrium, can also be used in combination with one or more components deployed within the right atrium. In the illustrated embodiment, an appendage 144 coupled to the anchor 142 extends from the anchor 142 in a superior to inferior direction. The appendage 144 includes a projection 146 that is sized and configured to rest in compression against tissue in, at, or near the septum in the right atrium at a location that is generally in opposition to a portion of the anterior annulus of the mitral valve in the left atrium. The compression force applied by the projection 146 is translated from the right heart side of the septum in relative position within the heart in total, septially across the septum in relation to the anterior annulus of the mitral valve on the left heart side of the septum, where it tends to orient vectors of the implant along the anterior annulus of the mitral valve inwardly toward the posterior annulus, as FIG. 51 shows. It thus has the equivalent therapeutic effect upon the mitral valve annulus imparted by the right heart implants 120 and 130 previously described, working in combination with the tension force applied by the right heart-anchored great cardiac vein implant 140.

Figure 52:
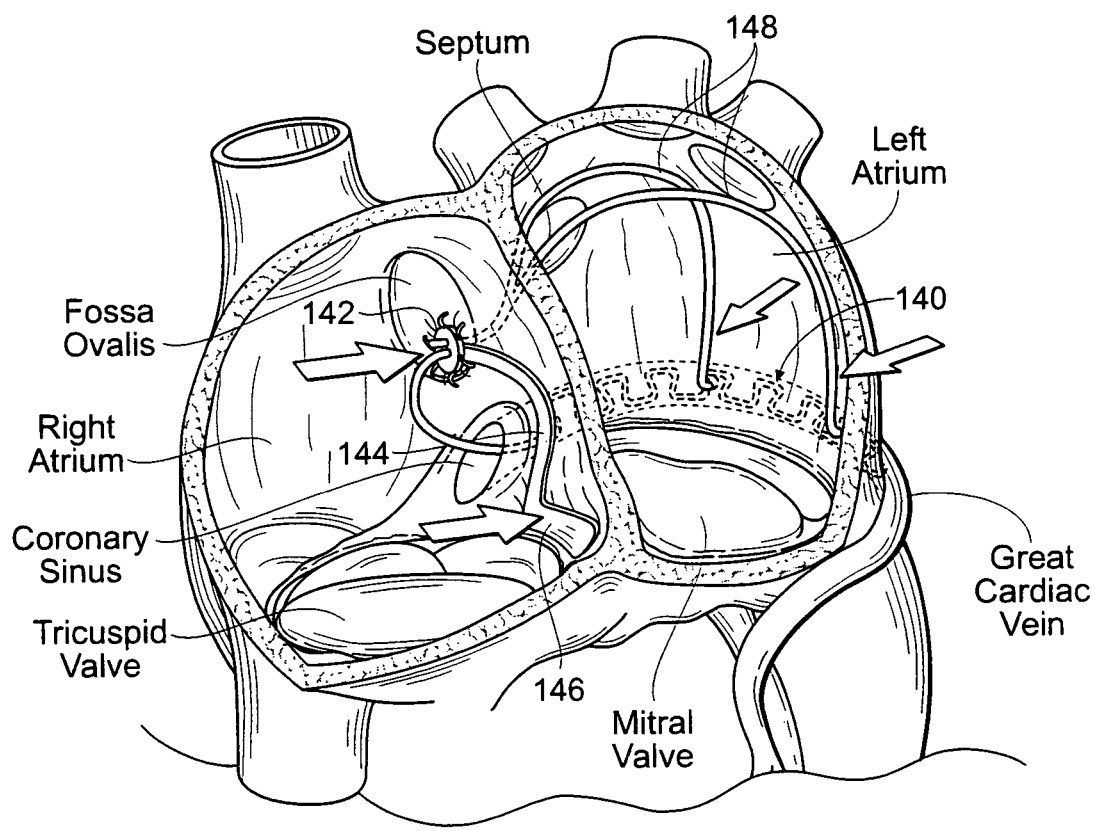
FIG. 52 is an anatomic anterior perspective view of the left and right atriums, with portions broken away and in section to show the presence of an implant system that includes two inter-atrial bridging elements with posterior regions anchored in the great cardiac vein and an anterior region anchored high on the interatrial septum, and further including an appendage that compresses tissue in, at or near the septum in opposition to a portion of the anterior mitral valve annulus in the left atrium.

As FIG. 52 shows, the great cardiac vein implant 140, placed into tension and anchored in the right atrium, and further augmented by the appendage 144 with its projection 146, can be used in combination with one or more other components 148 deployed within the left atrium. As FIG. 52 shows, the other components 148 can themselves comprise trans-septal components that are anchored to the great cardiac vein implant 140, as well as the septum, joined by a common anchor 142. In this arrangement, the components 148 apply horizontal pulling and/or vertical lifting forces upon the posterior mitral valve annulus in manner previously described, working in combination with the tension force applied by the right heart-anchored great cardiac vein implant 140, as well as the compression force applied by the projection 146.

It should by now be apparent that the features and concepts disclosed herein can be used, alone or in combination, to create implants or systems of implants that apply a selected force vector or a selected combination of force vectors, which allow mitral valve leaflets to better coapt. The features and concepts make possible rapid deployment, facile endovascular delivery, and full intra-atrial retrievability. The features and concepts also make use of strong fluoroscopic landmarks.

While the new devices and methods have been more specifically described in the context of the treatment of a mitral heart valve, it should be understood that other heart valve types can be treated in the same or equivalent fashion. By way of example, and not by limitation, the present systems and methods could be used to prevent or reduce retrograde flow in any heart valve annulus, including the tricuspid valve, the pulmonary valve, or the aortic valve. In addition, other embodiments and uses of the invention will be apparent to those skilled in the art from consideration of the specification and practice of the invention disclosed herein. The specification and examples should be considered exemplary and merely descriptive of key technical; features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

What is claimed is:

1. A method for treating a mitral heart valve comprising
identifying for treatment within a left atrium inside a heart a mitral valve having an annulus, the annulus including a minor axis having a native length, the left atrium also including a great cardiac vein that courses parallel to a posterior region of the annulus above the annulus, the left atrium being separated from a right atrium by an interatrial septum,
providing an implant including a bridging implant member having a posterior implant region and an anterior implant region the implant further including a posterior implant member in the form of an anchor structure configured to be positioned in a generally perpendicular relationship with the bridging implant member and joined to the posterior implant region, and said anterior implant region joined to the bridging implant an anterior implant member defined as an anchor button; wherein the bridging implant member is defined as a wire form structure
deploying the implant including
positioning the bridging implant member to span the left atrium above the annulus generally in a posterior-to-anterior direction,
positioning the anchor button entirely within the great cardiac vein with the posterior implant region extending into the heart through an atrial wall in the left atrium above a posterior region of the annulus, and
positioning the anchor button entirely inside the heart and solely within the right atrium with the anterior implant region extending through the interatrial septum above an anterior region of the annulus,
anchoring the posterior implant region solely to tissue inside the heart and into the great cardiac vein above the posterior region of the annulus while pulling on the anterior implant region from within the right atrium to place said wire form structure in tension within the left atrium and exert a pulling force on tissue at or near the posterior region of the annulus to draw the posterior region of the annulus inwardly toward an anterior region of the annulus and thereby shorten the annulus along the minor axis, and
anchoring the anterior implant region solely to tissue inside the heart and into the right atrium above the anterior region of the annulus to hold the tension on said wire form structure.

2. A method according to claim 1
wherein the implant comprises a suture material.

3. A method according to claim 1
wherein said anchor structure comprises a cross bar that anchors the posterior implant region solely to tissue inside the heart within the great cardiac vein.

4. A method according to claim 1
wherein said anchor structure comprises, at least in part, a radiopaque material.

5. A method according to claim 1
wherein deploying the implant includes establishing an intravascular path that extends from the right atrium through the interatrial septum into the left atrium, and wherein the implant is deployed, at least in part, through the intravascular path.

6. A method according to claim 5
wherein establishing an intravascular path includes forming a passage through the interatrial septum in or near a fossa ovalis.

7. A method according to claim 1
wherein said anchor structure comprises an expandable scaffold which, prior to deploying, is separate from the posterior implant region,
said expandable scaffold connected to posterior implant region after deploying.

8. A method according to claim 1
wherein said anchor structure is defined as a T-shaped anchor integrally joined to the posterior implant region.

* * * * *